United States Patent [19]
Zurflüh et al.

[11] Patent Number: 5,977,182
[45] Date of Patent: Nov. 2, 1999

[54] O-BENZYL OXIME ETHER DERIVATIVES AND THEIR USE AS PESTICIDES

[75] Inventors: René Zurflüh, Basel; Hugo Ziegler, Witterswil, both of Switzerland; Stephan Trah, Freiburg, Germany

[73] Assignee: Novartis Finance Corporation, New York, N.Y.

[21] Appl. No.: 08/836,176

[22] PCT Filed: Nov. 6, 1995

[86] PCT No.: PCT/EP95/04357

§ 371 Date: May 1, 1997

§ 102(e) Date: May 1, 1997

[87] PCT Pub. No.: WO96/16026

PCT Pub. Date: May 30, 1996

[30] Foreign Application Priority Data

Nov. 17, 1994 [CH] Switzerland ............... 3467/94

[51] Int. Cl.$^6$ ............ A01N 33/24; A01N 43/40
[52] U.S. Cl. .......... 514/640; 514/339; 514/417; 544/106; 544/182; 544/189; 546/189; 546/345; 548/475; 504/312
[58] Field of Search ............. 514/339, 417, 514/640; 544/106, 182; 546/189, 345; 548/475; 504/312

[56] References Cited

U.S. PATENT DOCUMENTS 5,756,426  5/1998  Ziegler et al. ............. 504/312

FOREIGN PATENT DOCUMENTS

WO 95/18789  7/1995  WIPO.
WO 95/21153  8/1995  WIPO.

Primary Examiner—Gary Geist
Assistant Examiner—Taylor Victor Oh
Attorney, Agent, or Firm—Gabriel Lopez

[57] ABSTRACT

Compounds of formula (I), wherein Y is hydrogen, $C_1$–$C_4$alkyl, $C_1$–$C_4$alkoxy, OH, CN, $NO_2$, $Si(CH_3)_3$, $CF_3$ or halogen, and T is a group (a) or (b), and wherein the remaining substituents have the following definitions: X is O, S or $NR_{13}$; A is O or $NR_4$; $R_1$ is hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano; $R_2$ is hydrogen, $C_1$–$C_6$alkyl, $C_3$–$C_6$cycloalkyl, cyano unsubstituted or substituted $C_1$–$C_6$alkoxycarbonyl, unsubstituted or substituted di($C_1$–$C_6$alkyl)aminocarbonyl, unsubstituted or substituted $C_1$–$C_6$alkyl-$S(O)_q$, unsubstituted or substituted aryl-$S(O)_q$, unsubstituted or substituted heteroaryl, unsubstituted or substituted heterocyclyl, unsubstituted or substituted heterocyclylcarbonyl or unsubstituted or substituted phenyl; and $R_3$ is hydrogen, unsubstituted or substituted alkyl, unsubstituted or substituted $C_3$–$C_6$cycloalkyl, unsubstituted or substituted phenyl or unsubstituted or substituted pyridyl; and wherein the remaining substituents are as defined herein, are pesticidal active ingredients. They can be used in pest control, especially as microbicides, insecticides and acaricides in agriculture, in horticulture and in the hygiene sector.

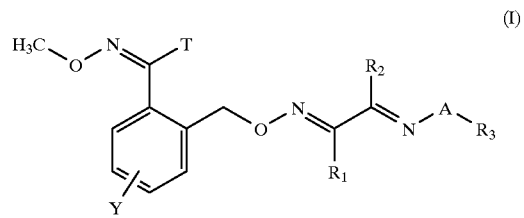

(I)

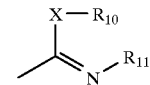

(a)

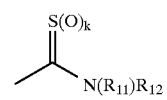

(b)

30 Claims, No Drawings

O-BENZYL OXIME ETHER DERIVATIVES AND THEIR USE AS PESTICIDES

The invention relates to novel pesticidally active compounds of formula I

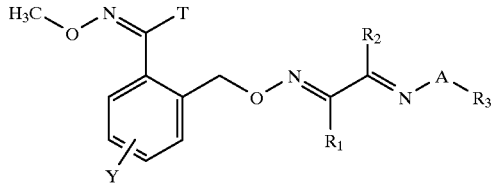

and to their possible isomers and isomeric mixtures, wherein
Y is hydrogen, $C_1$–$C_4$alkyl, $C_1$–$C_4$alkoxy, OH, CN, $NO_2$, $Si(CH_3)_3$, $CF_3$ or halogen,
T is a group a)

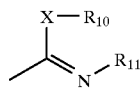

or b)

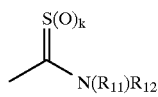

and the remaining substituents are defined as follows:
X is O, S or $NR_{13}$;
A is O or $NR_4$;
$R_1$ is hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano;
$R_2$ is hydrogen, $C_1$–$C_6$alkyl, $C_3$–$C_6$cycloalkyl, cyano, unsubstituted or substituted $C_1$–$C_6$alkoxycarbonyl, unsubstituted or substituted di($C_1$–$C_6$alkyl) aminocarbonyl, unsubstituted or substituted $C_1$–$C_6$alkyl-S(O)$_q$, unsubstituted or substituted aryl-S(O)$_q$, unsubstituted or substituted heteroaryl, unsubstituted or substituted heterocyclyl or unsubstituted or substituted heterocyclylcarbonyl; a group

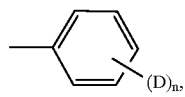

a group

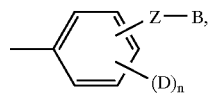

or thienyl;
D is identical or different and is selected from halogen, $C_1$–$C_4$alkyl, $C_1$–$C_4$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, cyano and nitro;

n is 0, 1, 2, 3 or 4;
Z is —O—, —O-($C_1$–$C_4$alkyl)-, -($C_1$–$C_4$alkyl)-O—, —S(O)$_m$—, -($C_1$–$C_4$alkyl)-S(O)$_m$— or —S(O)$_m$-($C_1$–$C_4$alkyl)-,
m is 0, 1 or 2,
B is $C_1$–$C_6$alkyl, halo-$C_1$–$C_6$alkyl, $C_3$–$C_6$cycloalkyl; $C_2$–$C_6$alkenyl or $C_2$–$C_4$alkynyl-$C_1$–$C_2$alkyl each of which is unsubstituted or substituted by from 1 to 3 halogen atoms; aryl, heteroaryl or heterocyclyl, all three of which are unsubstituted or substituted by from one to five identical or different substituents selected from $C_1$–$C_6$alkyl, halo-$C_1$–$C_6$alkyl, halogen, $C_1$–$C_6$alkoxy and halo-$C_1$–$C_6$alkoxy, or is a group

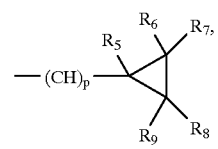

or trimethylsilyl;
$R_5$, $R_6$, $R_7$, $R_8$ and $R_9$ are each independently of the others hydrogen, $C_1$–$C_4$alkyl or halogen and
is 0, 1, 2 or 3;
q is 1 or 2;
$R_3$ is hydrogen, $C_1$–$C_6$alkyl, $C_1$–$C_6$haloalkyl having from 1 to 5 halogen atoms, $C_1$–$C_4$alkoxy-$C_1$–$C_2$alkyl, $C_2$–$C_4$alkenyl-$C_1$–$C_2$alkyl that is unsubstituted or substituted by from 1 to 3 halogen atoms, $C_2$–$C_4$alkynyl-$C_1$–$C_2$alkyl, $C_3$–$C_6$cycloalkyl that is unsubstituted or substituted by from 1 to 4 halogen atoms, $C_3$–$C_6$cycloalkyl-$C_1$–$C_4$alkyl that is unsubstituted or substituted by from 1 to 4 halogen atoms, cyano-$C_1$–$C_4$alkyl; $C_1$–$C_4$alkoxycarbonyl-$C_1$–$C_2$alkyl, $C_1$–$C_4$alkoxycarbamoyl-$C_1$–$C_2$alkyl, phenyl-$C_1$–$C_3$alkyl that is unsubstituted or substituted by halogen, $C_1$–$C_3$alkyl, $C_1$–$C_4$alkoxy, $C_1$–$C_4$haloalkyl, cyano, nitro or by $C_1$–$C_4$alkylenedioxy, it being possible for the phenyl group to be mono- to tri-substituted by identical or different substituents; phenyl that is unsubstituted or substituted by one or two substituents selected independently of one another from $C_1$–$C_4$alkyl, $C_1$–$C_4$alkoxy, halogen, $C_1$–$C_2$haloalkyl having from 1 to 3 halogen atoms, nitro and cyano, or pyridyl that is unsubstituted or substituted by one or two substituents selected independently of one another from $C_1$–$C_4$alkyl, $C_1$–$C_4$alkoxy, halogen, $C_1$–$C_2$haloalkyl having from 1 to 3 halogen atoms, nitro and cyano;
$R_4$ is $C_1$–$C_4$alkyl or phenyl, or
$R_3$ and $R_4$, together with the nitrogen atom to which they are bonded, form an unsubstituted or $C_1$–$C_4$alkyl-substituted, saturated or unsaturated 5- to 7-membered ring which may contain from 1 to 3 additional hetero atoms selected from N, O and S;
$R_{10}$ is hydrogen, $C_1$–$C_4$alkyl, $C_2$–$C_4$alkenyl, $C_2$–$C_4$alkynyl, $C_3$–$C_6$cycloalkyl, phenyl that is unsubstituted or substituted by a maximum of three substituents selected from halogen, $C_1$–$C_4$alkyl, $C_1$–$C_4$alkoxy and $C_1$–$C_4$alkylthio, or benzyl that is unsubstituted or substituted in the same manner in the aromatic nucleus by a maximum of three substituents; cyclopropylmethyl, $C_1$–$C_4$haloalkyl, $C_2$–$C_4$haloalkenyl, $C_2$–$C_5$-alkoxyalkyl, cyanomethyl, CO—$R_{14}$, OH, $NH_2$, $C_1$–$C_6$alkylamine, $C_1$–$C_4$haloalkylamine or $C_1$–$C_4$alkoxycarbonyl-$C_1$–$C_2$alkyl;

$R_{11}$ is hydrogen, $C_1$–$C_4$alkyl, $C_2$–$C_4$alkenyl, $C_2$–$C_4$alkynyl, $C_3$–$C_6$cycloalkyl, $C(O)R_4$, OH, $NH_2$, $C_1$–$C_4$alkoxy, $C_2$–$C_4$alkenyloxy, $C_2$–$C_4$alkynyloxy, $C_1$–$C_4$alkylamine or $C_1$–$C_4$haloalkylamine;

$R_{12}$ is hydrogen, $C_1$–$C_4$alkyl or $C_2$–$C_4$alkenyl; or $R_{11}$ and $R_{12}$, together with the nitrogen atom to which they are bonded, form an unsubstituted or $C_1$–$C_4$alkyl-substituted, saturated or unsaturated 5- to 7-membered ring which may contain from 1 to 3 additional hetero atoms selected from N, O and S;

k is 0 or 1;

$R_{13}$ is hydrogen, $C_1$–$C_4$alkyl, $C_2$–$C_4$alkenyl or $C_2$–$C_4$alkynyl;

$R_{14}$ is hydrogen, $C_1$–$C_4$alkyl, $C_1$–$C_4$haloalkyl, $C_1$–$C_4$alkoxy, $C_3$–$C_6$cycloalkyl, $C_1$–$C_4$-alkoxycarbonyl, or phenyl that is unsubstituted or substituted by a maximum of three substituents selected from halogen, $C_1$–$C_4$alkyl and $C_1$–$C_4$alkoxy.

The compounds according to the invention have fungicidal, acaricidal and insecticidal properties and are suitable as active ingredients for use in agriculture, in horticulture and in the hygiene sector.

The invention relates further to a process for the preparation of the compounds according to the invention, to fungicidal, acaricidal and insectidal compositions that comprise such compounds as active ingredients, and to the use of such compounds and compositions in the control of phytopathogenic fungi, Acarina and insects and in the prevention of attack by such organisms.

When asymmetric carbon atoms are present in the compounds of formula I, then the compounds occur in optically active form. Simply on the basis of the presence of the aliphatic oximino and hydrazono double bonds, the compounds will in any case occur in the [E]- and/or [Z]-forms. Atropisomerism may also occur. Formula I is intended to include all those possible isomeric forms, as well as mixtures thereof, for example racemic mixtures and any [E/Z] mixtures.

The general terms used hereinbefore and hereinafter have the meanings given below, unless otherwise defined.

Halogen is fluorine, chlorine, bromine or iodine, especially fluorine, chlorine or bromine, more especially fluorine or chlorine.

Alkyl is either straight-chained, for example methyl, ethyl, n-propyl, n-butyl, n-hexyl, n-octyl, n-decyl, n-dodecyl, n-hexadecyl or n-octadecyl, or branched, for example isopropyl, isobutyl, sec-butyl, tert-butyl, isopentyl, neopentyl or isohexyl.

Alkenyl is straight-chained or branched alkenyl, such as vinyl, 1-methylvinyl, allyl, 1-butenyl or isopropenyl, especially allyl.

Alkynyl is, for example, ethynyl, 1-propynyl or 1-butynyl, especially propargyl.

Cycloalkyl is to be understood as being cyclopropyl, cyclobutyl, cyclopentyl or cyclohexyl.

Halo-substituted groups, such as haloalkyl and haloalkoxy, may be partially or completely halogenated by identical or different halogen substituents.

Straight-chained $C_1$–$C_4$alkylenedioxy is —O—$CH_2$—O—, —O—$CH_2CH_2$—O—, —O—$CH_2CH_2CH_2$—O— or —O—$CH_2CH_2CH_2CH_2$—O—.

Substituents of optionally substituted alkoxycarbonyl, dialkylaminocarbonyl and alkyl-$S(O)_q$— groups are from 1 to 3 identical or different substituents selected from halogen, cyano, methoxy, methylthio, cyclopropyl, alkenyl and alkynyl.

Substituents of optionally substituted aryl-$S(O)_q$—, heteroaryl and heterocyclyl groups are from 1 to 3 identical or different substituents selected from $C_1$–$C_4$alkyl, halogen, cyano, nitro, $C_1$–$C_4$alkoxy, $C_1$–$C_4$alkylthio, halo-$C_1$–$C_2$alkyl, halo-$C_1$–$C_2$alkoxy and $C_1$–$C_4$alkoxycarbonyl.

Aryl is phenyl or naphthyl, preferably phenyl.

The term heteroaryl includes furan, pyrrole, and aromatic 5-membered rings having two or three identical or different hetero atoms N, O or S and aromatic 6-membered rings having from one to three identical or different hetero atoms N, O or S, all of which may be benzo-fused, and the radical benzothienyl. Other individual examples that may be mentioned are pyridine, pyrimidine, pyrazine, thiazole, oxazole, isoxazole, isothiazole, triazine, quinoline, isoquinoline, pyridazine, pyrazole, imidazole, quinazoline, quinoxaline, benzimidazole, benzofuran, indole, isoindole and benzothiazole.

The term heterocyclyl denotes 5- to 7-membered rings containing from 1 to 3 identical or different hetero atoms N, O or S. Examples are $\Delta^2$-oxazoline, $\Delta^2$-thiazoline; 5,6-dihydro-4H-1,3-thiazine; 5,6-dihydro-4H-1,3-oxazine, and also pyrrolidine, piperidine, morpholine, 4-alkylpiperidine and azepine.

The 5- to 7-membered rings that are formed by $R_3$ and $R_4$ together with the nitrogen atom to which they are bonded include especially pyrrolidine, piperidine, morpholine, thiomorpholine, hexamethyleneimine, imidazole, pyrazole, pyrrole, 1,2,4-triazole, 1,2,3-triazole, tetrazole, isoxazole, oxazole, isoxazolidine, oxazolidine, thiazole, isothiazole, thiazoline, isothiazolidine and azepine.

Preference is given within the scope of the invention to
(1) compounds of formula I wherein
    Y is hydrogen;
(2) compounds of formula I wherein
    T is the group a);
    X is oxygen;
    $R_{10}$ is $C_1$–$C_2$alkyl;
    $R_{11}$ is hydrogen, $C_1$–$C_2$alkyl, OH or $C_1$–$C_2$alkoxy, especially those wherein $R_{10}$ is methyl and $R_{11}$ is hydrogen or methyl;
(3) compounds of formula I wherein
    T is the group a);
    X is sulfur;
    $R_{10}$ is methyl, ethyl, allyl, benzyl or cyclopropylmethyl; and
    $R_{11}$ is hydrogen or $C_1$–$C_2$alkyl;
(4) compounds of formula I wherein
    T is the group a);
    X is $NR_{13}$ and
    $R_{13}$ is hydrogen or $C_1$–$C_4$alkyl, while $R_{10}$ and $R_{11}$ are each independently of the other hydrogen, $C_1$–$C_4$alkyl, $C_1$–$C_6$alkylamine or $C_1$–$C_4$haloalkylamine;
Of the last-mentioned compounds, preference is given to those wherein
    $R_{13}$ is hydrogen,
    $R_{10}$ is $C_1$–$C_6$alkylamine or $C_1$–$C_4$haloalkylamine and
    $R_{11}$ is $C_1$–$C_2$alkyl;
(5) compounds of formula I wherein
    T is the group b) wherein
    $R_{11}$ is $C_1$–$C_2$alkyl and
    k is 0 or 1;

(6) compounds of formula I wherein
A is oxygen, $NCH_3$ or $N-C_6H_5$, especially oxygen or $NCH_3$, more especially oxygen;

(7) compounds of formula I wherein
$R_1$ is hydrogen, methyl, cyclopropyl, methylthio or cyano, especially methyl;

(8) compounds of formula I wherein
$R_2$ is $C_1-C_4$alkyl or cyclopropyl, especially methyl or cyclopropyl;

(9) compounds of formula I wherein
$R_2$ is cyano, unsubstituted or substituted $C_1-C_6$alkoxycarbonyl, unsubstituted or substituted di($C_1-C_6$alkylamine)carbonyl, unsubstituted or substituted heterocyclylcarbonyl, unsubstituted or substituted $C_1-C_6$alkyl-$S(O)_q$, unsubstituted or substituted aryl-$S(O)_q$, unsubstituted or substituted heteroaryl, unsubstituted or substituted heterocyclyl; especially unsubstituted or substituted $C_1-C_6$alkoxycarbonyl, unsubstituted or substituted heterocyclyl or unsubstituted or substituted heteroaryl; and wherein
q 1 or 2;

(10) compounds of formula I wherein
$R_2$ is a group

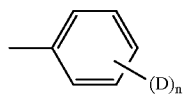

and
D is halogen, $C_1-C_4$alkyl, $C_1-C_4$alkoxy, $C_1-C_2$alkyl substituted by from 1 to 5 halogen atoms, $C_1-C_2$haloalkoxy, $C_3-C_6$alkenyloxy, $C_3-C_6$alkynyloxy, $C_1-C_4$alkylenedioxy, cyano, or nitro, or thienyl,
and D is especially fluorine, chlorine, bromine, $C_1-C_4$alkyl or $-CF_3$;

(11) compounds of formula I wherein $R_2$ is a group

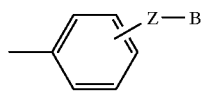

and
Z is $-O-$, $-O-(C_1-C_4$alkyl$)-$, $-(C_1-C_4$alkyl$)-O-$, $-S(O)_m-$, $-(C_1-C_4$alkyl$)-S(O)_m-$, $-S(O)_m-(C_1-C_4$alkyl$)-$,
especially $-O-$, $-CH_2-O-$ or $-O-CH_2-$ or $-S(O)_m-$,
very especially $-O-CH_2-$, and
m is 0, 1 or 2;

(12) compounds of formula I wherein
$R_2$ is a group

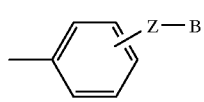

and
B is $C_1-C_4$alkyl, halo-$C_1-C_4$alkyl; $C_2-C_4$alkenyl or $C_2-C_4$alkynyl-$C_1-C_2$alkyl each of which is unsubstituted or substituted by from 1 to 3 halogen atoms; aryl or aryl that is substituted by one or two substituents selected independently of one another from $C_1-C_2$alkyl, halo-$C_1-C_2$alkyl, halogen, $C_1-C_2$alkoxy and halo-$C_1-C_2$alkoxy, or is a group

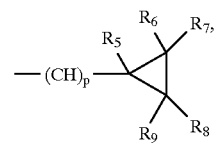

$R_5$, $R_6$, $R_7$, $R_8$ and $R_9$ are each independently of the others hydrogen, $C_1-C_2$alkyl or halogen and
p is 0, 1, 2 or 3; and
B is especially $C_1-C_2$alkyl, halo-$C_1-C_3$alkyl, allyl or propargyl that is unsubstituted or substituted by 1 or 2 halogen atoms or by 1 or 2 methyl groups, phenyl, phenyl substituted by a substituent selected from the group consisting of fluorine, chlorine, bromine and $CF_3$, or is a group

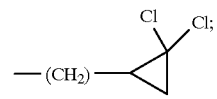

(13) compounds of formula I wherein
$R_2$ is a phenyl group substituted in the 4-position by $-Z-B$;

(14) compounds of formula I wherein
$R_3$ is hydrogen, $C_1-C_6$alkyl, $C_1-C_4$haloalkyl having from 1 to 3 halogen atoms, $C_1-C_2$alkoxy-$C_1-C_2$alkyl, $C_1-C_4$alkoxycarbonyl-$C_1-C_2$alkyl, propenyl that is unsubstituted or substituted by from 1 to 3 halogen atoms, propargyl, $C_3-C_6$cycloalkyl, cyclopropylmethyl that is unsubstituted or substituted by 1 or 2 halogen atoms, cyano-$C_1-C_2$alkyl, phenyl-$C_1-C_2$alkyl that is unsubstituted or substituted by halogen, methyl, methoxy or by halomethyl having from 1 to 3 halogen atoms, wherein the phenyl group may have one or two identical or different substituents; phenyl that is unsubstituted or substituted by one or two substituents selected independently of one another from halogen, methyl, methoxy, halomethyl having from 1 to 3 halogen atoms, cyano and nitro; or pyridyl that is unsubstituted or substituted by one or two substituents selected independently of one another from halogen, methyl, methoxy, halomethyl having from 1 to 3 halogen atoms, cyano and nitro; or $R_3$ and $R_4$, together with the nitrogen atom to which they are bonded, form an unsubstituted or $C_1-C_4$alkyl-substituted, saturated or unsaturated 5- to 7-membered ring which may contain from 1 to 3 additional hetero atoms selected from N, O and S; and, preferably,
$R_3$ is hydrogen, $C_1-C_6$alkyl, $C_1-C_4$haloalkyl having from 1 to 3 halogen atoms, $C_1-C_2$alkoxymethyl, prop-2-en-1-yl that is unsubstituted or substituted by from 1 to 3 halogen atoms, propargyl, $C_3-C_6$cycloalkyl, cyclopropylmethyl that is unsubstituted or substituted by 1 or 2 fluorine or chlorine atoms, cyano-$C_1-C_2$alkyl, phenyl-$C_1-C_2$alkyl that is unsubstituted or substituted by halogen, methyl, methoxy or by halomethyl having from 1 to 3 halogen atoms, wherein the phenyl group may be substituted by 1 or 2 identical or different substituents; phenyl that is unsubstituted or substituted by one or two substituents selected independently of one another from halogen, methyl, methoxy, halomethyl having from 1 to 3 halogen atoms, cyano and nitro; or pyridyl that is unsubstituted or substituted by 1 or 2 identical or different substituents selected independently of one another from halogen, methyl, methoxy, halomethyl having from 1 to 3 halogen atoms, cyano and nitro; or $R_3$ and $R_4$, together with the nitrogen atom to which they are bonded, form 1,2,4-triazolyl, 4-morpholinyl, 1-azepinyl, 1-piperidinyl or 1-pyrrolidinyl;

(15) a compound of formula I wherein
  $R_4$ is methyl or phenyl, especially methyl;
(16) a compound of formula I wherein
  $R_3$ is $C_1$–$C_6$alkyl, $C_1$–$C_6$haloalkyl having from 1 to 5 halogen atoms, or $C_3$–$C_6$cycloalkyl-$C_1$–$C_4$alkyl that is unsubstituted or substituted by from 1 to 4 halogen atoms;
(17) a compound of formula I wherein
  $R_2$ is methyl, cyano, cyclopropyl, unsubstituted or substituted $C_1$–$C_6$alkoxycarbonyl, unsubstituted or substituted heterocyclyl or unsubstituted or substituted heteroaryl and
  $R_3$ is $C_1$–$C_6$alkyl, $C_1$–$C_6$haloalkyl, or $C_3$–$C_6$cycloalkyl-$C_1$–$C_4$alkyl that is unsubstituted or substituted by from 1 to 4 halogen atoms; and
(18) a compound of formula I wherein the $CH_3ON{=}C$ double bond has the E-form.

The compounds of formula I can be prepared as follows:
(In the following formulae of Sections A) to I), unless otherwise indicated the radicals X, Y, T and $R_{10}$ to $R_{14}$ are as defined for formula I, and
Q is the group

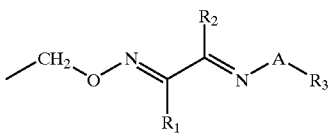

wherein $R_1$, $R_2$, $R_3$ and A are as defined for formula I.)

The imino ethers, iminothioethers and amidines of the general formula II

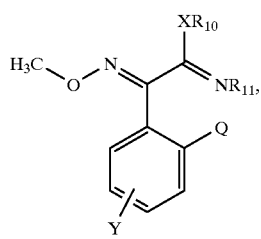

II wherein $R_{10}$, $R_{11}$, Q and Y are as defined, can be prepared analogously to known methods, such as those referred to in the following literature references:
  "The Chemistry of amidines and imidates" ed. S. Patai, John Wiley & Sons, Vol. 1, 1974 and Vol. 2, 1991, Chapters 7 and 9;
  Houben-Weyl "Methoden der organischen Chemie" Vol. 8, 1975 and E5, 1985.

A) For example, imino(thio)ethers of the general formula II wherein X is oxygen or sulfur and wherein $R_{10}$ and Y are as defined above can be prepared in accordance with the following Scheme

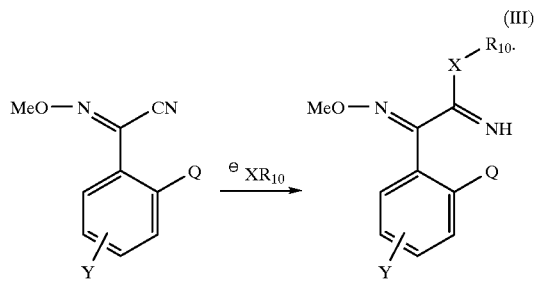

A nitrile of the general formula III is reacted with a (thio)alcoholate $R_{10}X^{\ominus}$ at a temperature of from 20° C. to 150° C., if necessary in an autoclave under pressure. The corresponding (thio)alcohol or inert organic solvents, such as diethyl ether, dichloromethane, dimethylformamide, tetrahydrofuran or toluene, are used as diluents as appropriate.

B) Imino(thio)ethers of the general formula II wherein X is oxygen or sulfur can also be prepared from the (thio)amides of the general formula IV

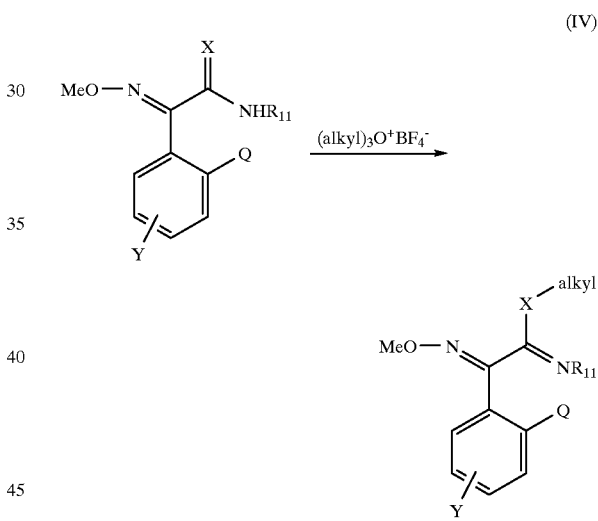

For that purpose, the (thio)amides are reacted with a trialkyloxonium tetrafluoroborate at a temperature of from 0° C. to 50° C. in a suitable solvent, such as dichloromethane, chloroform or toluene.

C) Iminothioethers of the general formula II wherein X is sulfur can also be prepared from the thioamides of the general formula V

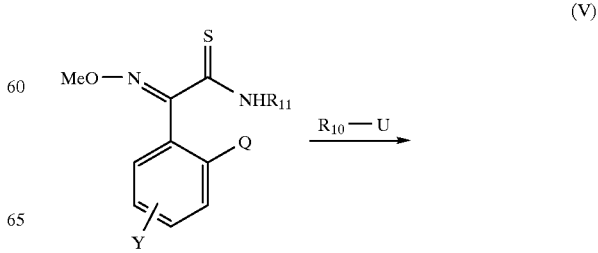

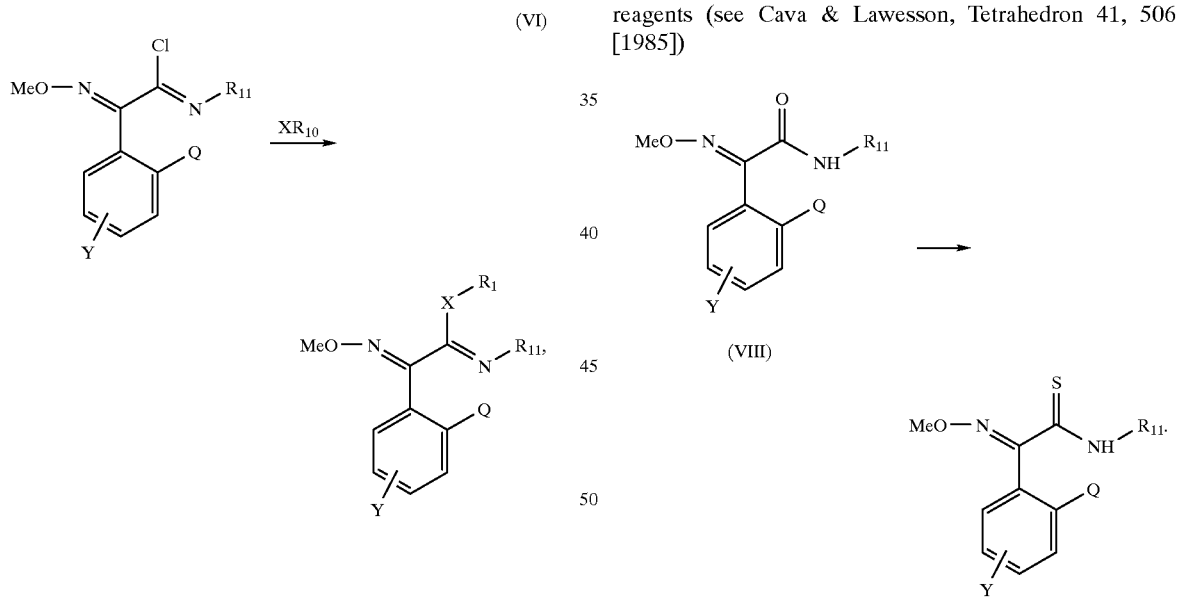

by reaction with a compound $R_{10}$-U wherein U is a leaving group. The reaction is carried out in the presence of bases, such as potassium carbonate, potassium hydroxide, sodium ethanolate and sodium hydride, in a suitable solvent, such as diethyl ether, tetrahydrofuran, dimethylformamide, dimethyl sulfoxide or toluene, at a temperature of from 10° C. to 100° C.

D) Imino(thio)ethers of the general formula II wherein $R_{11}$ is —C(O)$R_{14}$ can be prepared from the corresponding N-unsubstituted imino(thio)ethers by acylation.

E) In a further form of the process, imino(thio)ethers and amidines of the general formula II can be obtained, using chlorides of the general formula VI (VI)

as starting material, by reaction with (thio)alcoholates or amines in a suitable organic solvent, such as diethyl ether, dichloromethane, dimethylformamide, tetrahydrofuran or toluene, at a temperature of from −20° C. to +80° C. The chlorides themselves can be obtained from the corresponding (thio)amides, for example by reaction with phosphorus oxychloride, thionyl chloride or triphenylphosphine/carbon tetrachloride. See C. Ferri, Reaktionen der Organischen Synthese; p. 564, G. Thieme Verlag, Stuttgart 1978.

F) Amidines of the general formula II wherein X is $NR_{10}$ can also be prepared from the imino ethers of the general formula VII

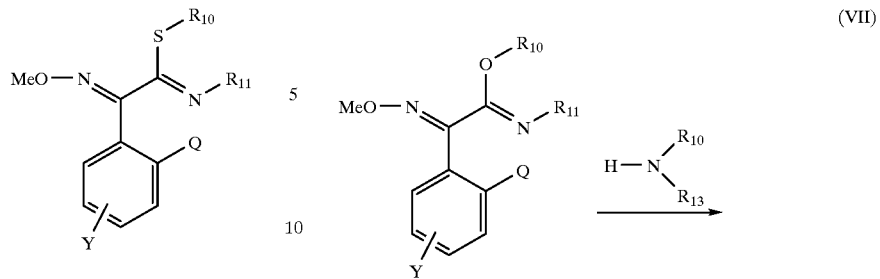

(VII)

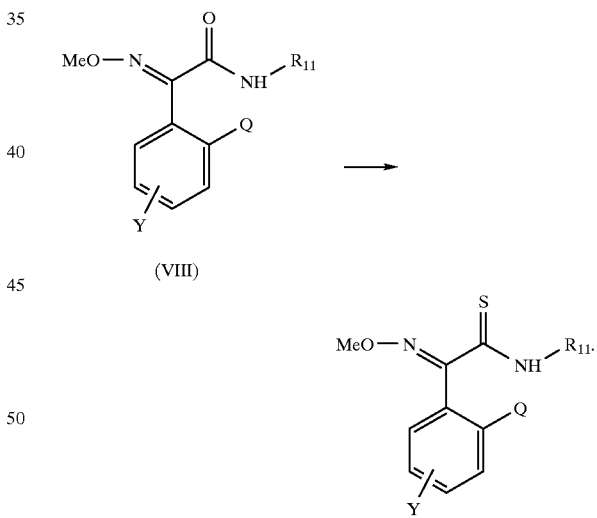

by reaction with a primary or secondary amine in a suitable solvent, such as dichloromethane, dioxane, dimethylformamide or toluene, at a temperature of from −20° C. to +60° C.

G) Thioamides of the general formula Ib can be prepared from the corresponding amides by "sulfuration". There may be used for that reaction, for example, $PS_5$ or Lawesson reagents (see Cava & Lawesson, Tetrahedron 41, 5061 [1985])

(VIII)

(Ib)

H) Furthermore, thioamides of the general formula Ib' can be obtained from the nitrites of formula III by the addition of hydrogen sulfide in the presence of a base, such as potassium carbonate, potassium hydroxide or triethylamine, in a suitable solvent, such as dichloromethane, dimethylformamide, chloroform, carbon tetrachloride or tetrahydro-furan; or by reaction with bis(trimethylsilyl) sulfide and sodium methanolate in accordance with P. Y. Lin, Synthesis 1992, (12), 1219

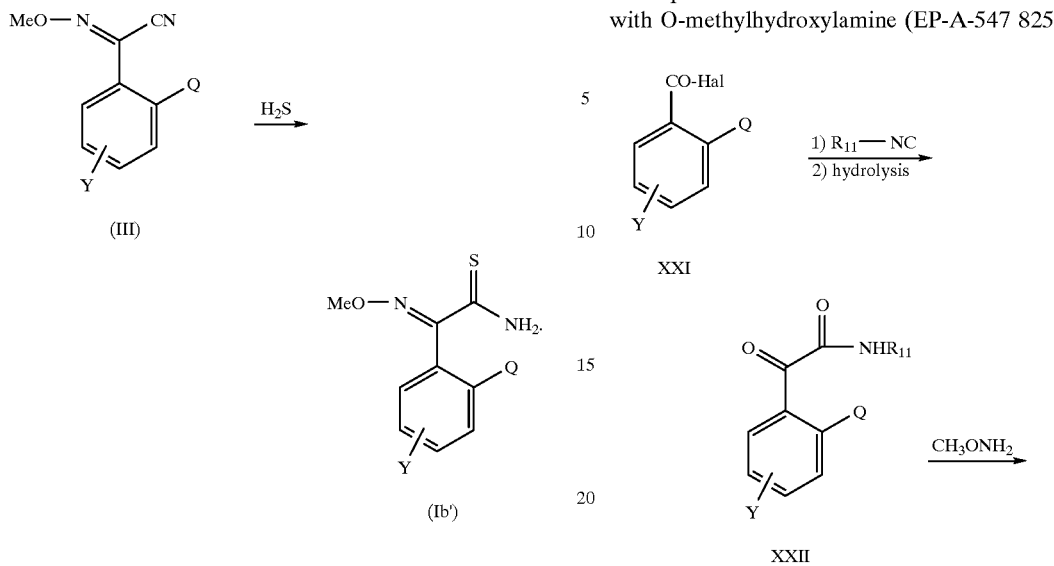

I) The thioamides thus obtained can be converted into the corresponding thiocarboxylic acid amide S-oxides by oxidation with, for example, hydrogen peroxide in glacial acetic acid.

The starting compounds for the above-mentioned reactions can be prepared in accordance with methods that are generally known, for example in accordance with Scheme 1 and Scheme 2 wherein A, X, Y, $R_1$, $R_2$ and $R_3$ are as defined above.

In addition, amides of formula VIII can be prepared, for example, by reaction of a benzoic acid halide of formula XXI with an isocyanide and subsequent hydrolysis to form a compound of the formula XXII which is reacted further with O-methylhydroxylamine (EP-A-547 825).

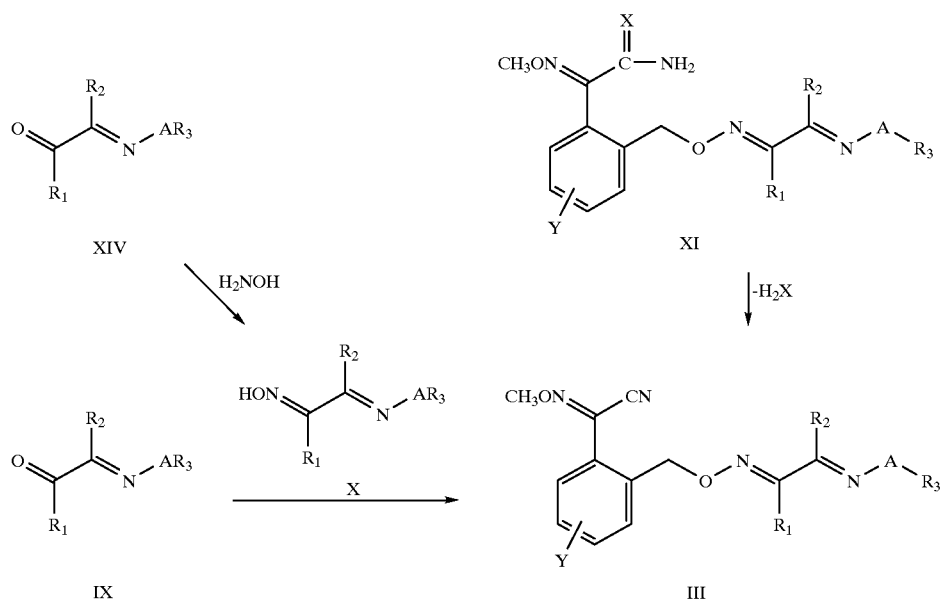

Scheme 1

U: leaving group
X: O, S

Scheme 2

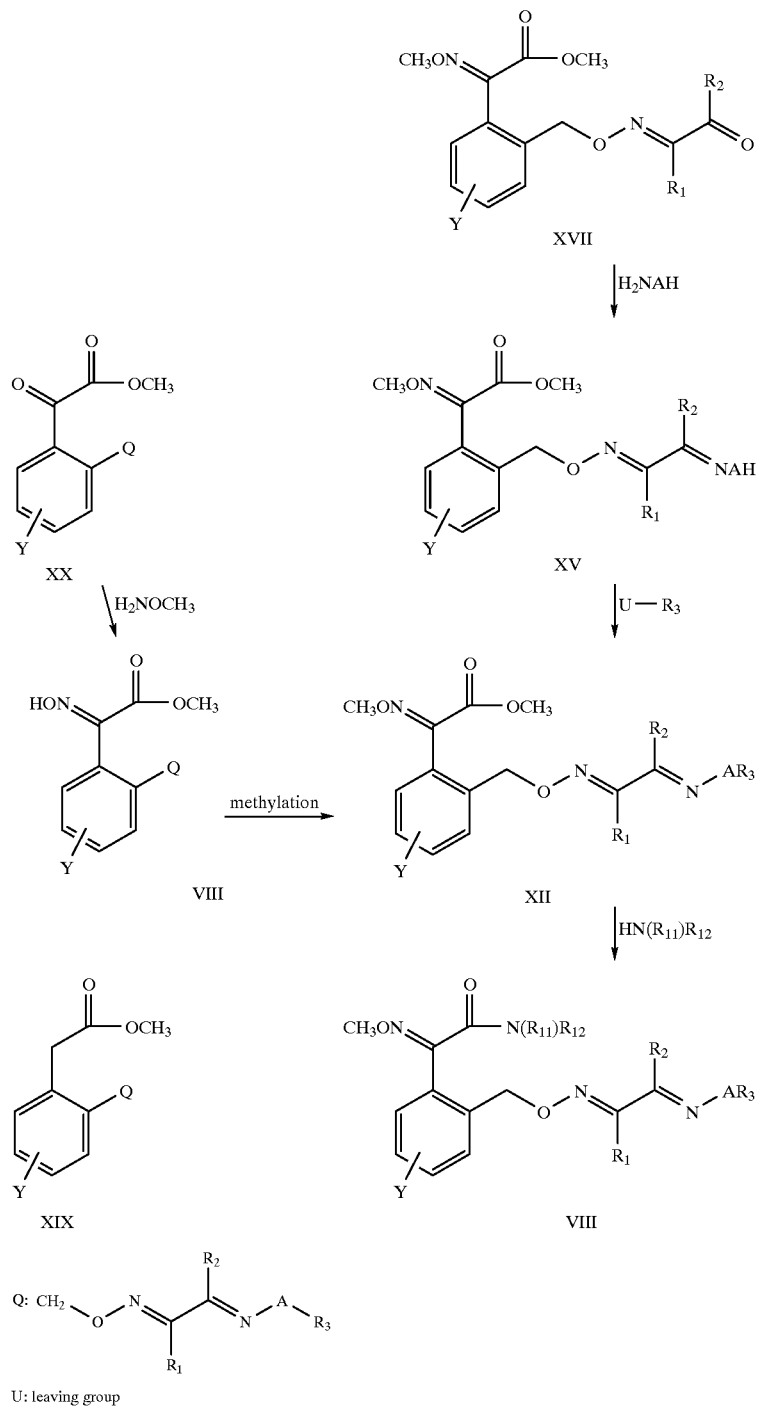

The preparation of the starting compounds shown in Scheme 1 and Scheme 2 is described, for example, in: EP-A-416 857 (XIV); EP-A-506 149 (XVII); EP-A-254 426 (XIX and XX).

Compounds of formula IX wherein U is halogen can be prepared from the known α-hydroximino-o-tolylacetonitrile by O-methylation with dimethyl sulfate or methyl iodide in the presence of a base, followed by halogenation, for example with N-bromo- or N-chloro-succinimide in boiling carbon tetrachloride.

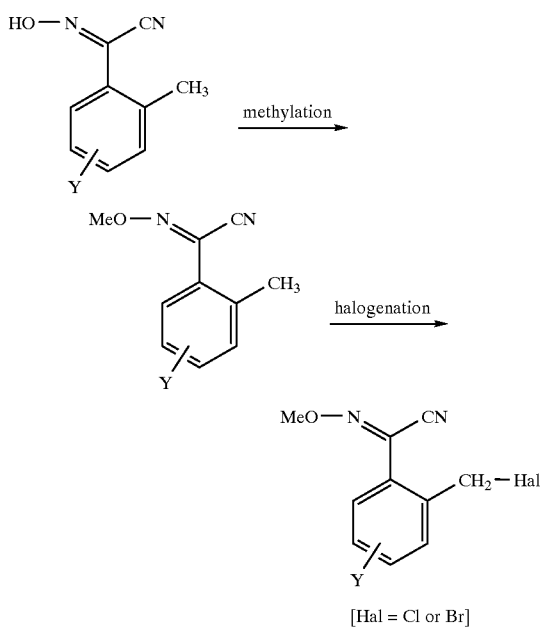

[Hal = Cl or Br]

The invention relates also to the novel intermediates of formula III

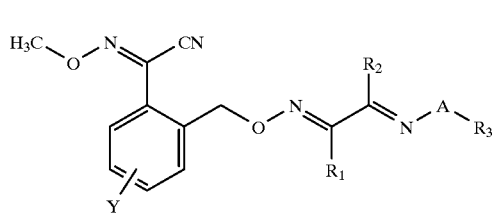

wherein A, $R_1$, $R_2$, $R_3$ and Y are as defined for formula I.

Preference is given to compounds of formula III wherein

A is oxygen, and

Y is hydrogen, and $R_1$, $R_2$ and $R_3$ are as defined for formula I; especially those wherein $R_1$ and $R_3$ are methyl.

The invention relates also to the novel intermediates of formula X

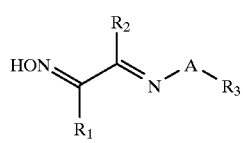

wherein A, $R_1$, $R_2$ and $R_3$ are as defined for formula I.

The intermediates of formulae III and X can additionally be used in the preparation of other phenylacetic acid derivatives, such as those described, for example, in WO 95/18789, WO 95/21153 and WO 95/21154.

It has now been found that compounds of formula I have, for practical requirements, an especially advantageous microbicidal spectrum in the control of phytopathogenic microorganisms, especially fungi. They have very advantageous curative, preventive and, in particular, systemic properties, and can be used in the protection of numerous plants. With the compounds of formula I it is possible to inhibit or destroy the pests which occur on plants or on parts of plants (the fruit, blossom, leaves, stems, tubers, roots) in different crops of useful plants, while at the same time parts of plants which grow later are also protected from phytopathogenic microorganisms.

The compounds of formula I can also be used as dressing agents for protecting seed (fruit, tubers, grains) and plant cuttings against fungus infections as well as against phytopathogenic fungi which occur in the soil.

Compounds of formula I are effective, for example, against the phytopathogenic fungi belonging to the following classes: *Fungi imperfecti* (especially Botrytis, Pyricularia, Helminthosporium, Fusarium, Septoria, Cercospora, Cercosporella and Alternaria); Basidiomycetes (e.g. Rhizoctonia, Hemileia, Puccinia); Ascomycetes (e.g. Venturia and Erysiphe, Podosphaera, Monilinia, Uncinula), and especially against the class of the Oomycetes (e.g. Phytophthora, Peronospora, Bremia, Pythium, Plasmopara).

The compounds of formula I according to the invention are also valuable active ingredients against insects and pests of the order Acarina, such as those occurring on useful plants and ornamentals in agriculture, horticulture and forestry, while being well tolerated by warm-blooded animals, fish and plants. The compounds of formula I are suitable especially for controlling pests, such as spider mites, aphids, budworms and plant- and leaf-hoppers in rice, in cotton, vegetable, fruit and rice crops. They are suitable mainly for the control of spider mites, such as *Panonychus ulmi*, aphids, such as *Aphis craccivora*, budworms, such as those of *Heliothis virescens*, and leaf- and plant-hoppers in rice, such as *Nilaparvata lugens* or *Nephotettix cincticeps*.

The good pesticidal activity of the compounds I according to the invention corresponds to a mortality of at least 50 to 60% of the mentioned pests.

Further areas of use of the compounds according to the invention are the protection of stored goods and materials, the stored material being protected against rotting and mould as well as against animal pests (for example grain weevils, mites, fly larvae, etc.). In the hygiene sector, compounds of formula I successfully control animal parasites, such as ticks, mites, botflies, etc., in or on domestic animals and productive livestock. The compounds I are effective against all or individual development stages of normally sensitive species of pests, but also of resistant species of pests. Their action may manifest itself, for example, in the mortality of the pests, which occurs immediately or only after some time, for example during moulting, or in reduced oviposition and/or hatching rate.

The activity of the compounds I according to the invention and of the compositions comprising them can be substantially broadened and adapted to prevailing circumstances by the addition of other insecticides and/or acaricides. Examples of suitable additives include representatives of the following classes of active ingredient: organophosphorus compounds, nitrophenols and derivatives, formamidines, ureas, carbamates, pyrethroids and chlorinated hydrocarbons.

Target crops to be protected within the scope of the present invention comprise e.g. the following species of plants: cereals (wheat, barley, rye, oats, triticale, rice, maize, sorghum and related species); beet (sugar beet and fodder beet); pomes, stone fruit and soft fruit (apples, pears, plums, peaches, almonds, cherries, strawberries, gooseberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as tobacco, nuts, coffee, sugar cane, tea, pepper and other spice plants, vines, hops, aubergines, bananas and natural rubber plants, as well as flowers and ornamentals.

The compounds of formula I are normally used in the form of compositions and can be applied to the crop area or plants to be treated, simultaneously or in succession, with further compounds. These further compounds can be fertilisers or micronutrient donors or other compositions that influence plant growth. It is also possible to use selective herbicides as well as insecticides, fungicides, bactericides, nematicides, molluscicides or mixtures of several of these compositions, if desired together with further carriers, surfactants or other application-promoting adjuvants customarily employed in formulation technology, without reducing the effectiveness of the compounds of formula I.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite.

Particularly advantageous application-promoting adjuvants which are able to reduce substantially the rate of application are also natural (animal or vegetable) or synthetic phospholipids of the series of the cephalins and lecithins, which can be obtained e.g. from soybeans.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurine salts.

Non-ionic surfactants are polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals.

The anionic, non-ionic or cationic surfactants customarily employed in formulation technology are known to the person skilled in the art or can be taken from the relevant specialist literature.

The agrochemical compositions usually comprise 0.1 to 99%, preferably 0.1 to 95%, of a compound of formula I, 99.9 to 1%, preferably 99.9 to 5%, of a solid or liquid adjuvant, and 0 to 25%, preferably 0.1 to 25%, of a surfactant.

Whereas commercial products will preferably be formulated as concentrates, the end user will normally employ dilute formulations.

The compositions may also comprise further adjuvants, such as stabilisers, antifoams, viscosity regulators, binders, tackifiers as well as fertilisers or other active ingredients for obtaining special effects.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredient with an extender, e.g. with a solvent (mixture), a solid carrier and, where appropriate, surface-active compounds (surfactants).

A preferred method of applying a compound of formula I or an agrochemical composition comprising at least one of those compounds is application to the leaves (foliar application). The frequency and rate of application depend upon the risk of infestation by the pathogen in question. The compounds of formula I can, however, also penetrate the plant through the roots via the soil (systemic action) if the locus of the plant is impregnated with a liquid formulation or if the compounds are introduced into the soil in solid form, e.g. in the form of granules (soil application). In paddy rice crops, such granules may be applied in metered amounts to the flooded rice field. The compounds of formula I may, however, also be applied to seeds (coating) either by impregnating the seeds with a liquid formulation of the active ingredient or by coating them with a solid formulation. In principle, any kind of plant propagation material can be protected using compounds of formula I, for example the seeds, roots, stems, twigs or shoots.

The compounds of formula I are used in unmodified form or, preferably, together with the adjuvants conventionally employed in formulation technology. For that purpose they are advantageously formulated in known manner e.g. into emulsifiable concentrates, coatable pastes, directly sprayable or dilutable solutions, dilute emulsions, wettable powders, soluble powders, dusts, granules, (by encapsulation in e.g. polymer substances). As with the nature of the compositions, the methods of application, such as spraying, atomising, dusting, scattering, coating or pouring, are chosen in accordance with the intended objectives and the prevailing circumstances. Advantageous rates of application are normally from 1 g to 2 kg of active ingredient (a.i.) per ha, preferably from 25 g to 800 g a.i./ha and especially from 50 g to 400 g a.i./ha. When used as seed-dressing agents, amounts of from 0.001 g to 1.0 g of active ingredient per kg of seed are advantageously used.

The Examples which follow serve to illustrate the invention in greater detail, but do not limit the invention.

1. PREPARATION EXAMPLES

Example P-1: Preparation of

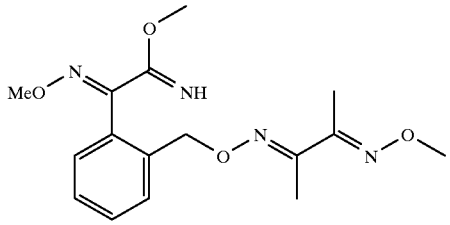

With stirring at room temperature, 1.99 g of trimethyloxonium tetrafluoroborate are added in a single portion to 3.44 g of 2-[([(3-methoximino-2-butyl)imino]oxy)o-tolyl]-glyoxylic acid amide O-methyloxime in 20 ml of dichloromethane. The resulting suspension is stirred for 20 hours and then diluted with 200 ml of ethyl acetate and washed with 150 ml of semi-saturated sodium chloride solution. The aqueous phase is extracted with a further 200 ml of ethyl acetate, and the combined organic phases are dried over magnesium sulfate and concentrated. The residue is purified by chromatography on silica gel with hexane/ethyl acetate (4:1) as eluant. O-Methyl-2-[([(3-methoximino-2-butyl) imino]oxy)-o-tolyl]-2-methoximinoacetimidates are obtained in the form of a solid. Crystals from heptane; m.p. 107–109.5° C.

Example P-2: Preparation of

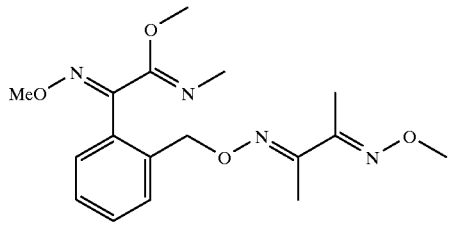

3.01 g of N-methyl-2-[([(3-methoximino-2-butyl)imino] oxy)o-tolyl]-2-methoximinoacetamide and 3.07 g of triphenylphosphine are dissolved in 10 ml of acetonitrile at approx. 40° C. The reaction mixture is then cooled to 20° C. and 0.96 ml of carbon tetrachloride is added to the white suspension in the course of 2 minutes. The resulting yellow solution is stirred for 3 hours at room temperature. While cooling with an ice-bath, the solution of imidoyl chloride thus obtained is added in the course of 30 minutes to a solution of 14.4 mmol of sodium methanolate in 10 ml of methanol. The yellow reaction mixture is stirred for a further 1 hour at room temperature and then poured into 150 ml of ice-water. The mixture is extracted with 2×250 ml of ethyl acetate and the extracts are dried over magnesium sulfate and concentrated using a rotary evaporator. The solid residue is purified by chromatography on silica gel using hexane/ethyl acetate (9:1) as eluant. N,O-Dimethyl-2-[([(3-methoximino-2-butyl)imino]oxy)-o-tolyl]-2-methoximinoacetimidates having a melting point of 71.6° C. are thus obtained.

Example P-3: Preparation of

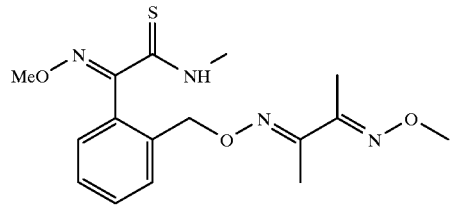

6.39 g of Lawesson reagent are added, with stirring, to a solution of 4.8 g of N-methyl-2-[([(3-methoximino-2-butyl) imino]oxy)o-tolyl]-2-methoximinoacetamide in 70 ml of toluene and the resulting suspension is then heated at 80° C. for 5 hours. The reaction mixture is then diluted with 200 ml of ethyl acetate and washed with 150 ml of water. The aqueous phase is extracted with a further 200 ml of ethyl acetate, and the combined organic phases are dried over magnesium sulfate and concentrated using a rotary evaporator. The residue is purified by chromatography on silica gel with hexane/ethyl acetate (4:1). N-Methyl-2-[([(3-methoximino-2-butyl)imino]oxy)o-tolyl]-2-methoximinothioacetamide is thus obtained in the form of a yellow oil; MS: M-HS 317 (2), 237 (79), 207 (46), 132 (74), 116 (39), 74 (100).

Example P-4: Preparation of

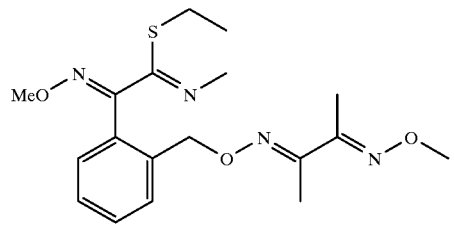

At room temperature, 1 g of potassium carbonate and 0.5 ml of ethyl bromide are added in succession, each in a single portion, to a yellow solution of 2.1 g of N-methyl-2-[([(3-methoximino-2-butyl)imino]oxy)o-tolyl]-2-methoximinoacetamide in 20 ml of dimethylformamide. The resulting suspension is then stirred for 24 hours at room temperature and then added to 150 ml of ice-water and extracted with 200 ml of ethyl acetate. The aqueous phase is again extracted with 200 ml of ethyl acetate and the combined organic phases are dried over magnesium sulfate and concentrated using a rotary evaporator. The residue is purified by chromatography on silica gel with hexane/ethyl acetate (9:1). N-Methyl,S-ethyl-2-[([(3-methoximino-2-butyl)imino]oxy)o-tolyl]-2-methoximino-thioacetimidates are obtained in the form of a slightly yellow oil. MS: M+ 378 (2), 347 (18), 317 (14), 265 (25), 235 (44), 205 (45), 116 (70), 72 (100).

PREPARATION OF INTERMEDIATES

Example P-5: Preparation of the Compound

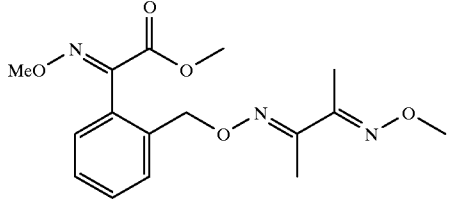

First a spatula tip of potassium iodide and then, over a period of 3 hours, a mixture consisting of 50 g of 2-(2-bromomethylphenyl)glyoxylic acid methyl ester O-methyloxime and 22.78 g of 2-hydroximino-3-methoximino-butane dissolved in 50 ml of dimethylformamide are added to a grey suspension of 8.4 g of an approx. 60% sodium hydride dispersion in 50 ml of dimethylformamide. The reaction temperature is maintained at from 25° C. to 50° C. with occasional cooling. The reaction mixture is then stirred for 3 hours at room temperature, poured into 500 ml of ice-water and extracted twice with 750 ml of ethyl acetate each time. The combined organic phases are dried over magnesium sulfate and concentrated using a rotary evaporator. The residue is purified by chromatography on silica gel with hexane/ethyl acetate (4:1). Methyl-2-[([(3-methoximino-2-butyl)imino]-oxy)o-tolyl]-2-methoximinoacetate having a melting point of 104–106° C. is thus obtained.

Example P-6: Preparation of the Compound

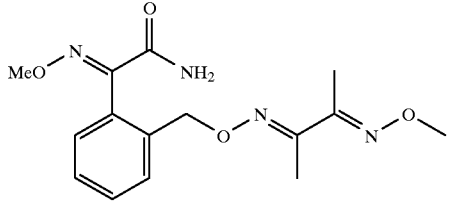

A yellow suspension of 16.77 g of methyl-2-[([(3-methoximino-2-butyl)imino]oxy)-o-tolyl]-2-methoximinoacetate in 120 ml of methanol is charged for a period of 6 hours with a constant stream of ammonia. The temperature rises initially to 46° C. The reaction solution, which has become clear, is then stirred overnight, during which time the product precipitates. The mixture is concentrated using a rotary evaporator and the residue is dissolved while hot in 50 ml of toluene and 50 ml of heptane. On cooling, crystalline 2-[([(3-methoximino-2-butyl)imino]oxy)o-tolyl]-2-methoximinoacetamide having a melting point of 127.5–128.5° C. is obtained.

Example P-7: Preparation of

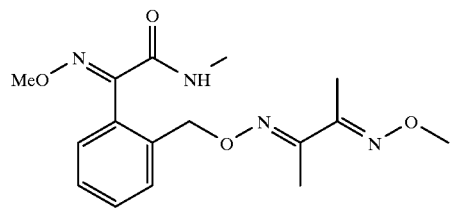

At room temperature, 5.62 ml of an 8 molar solution of methylamine in ethanol is added in a single portion to a suspension of 5.03 g of methyl-2-[([(3-methoximino-2-butyl)imino]-oxy)o-tolyl]-2-methoximinoacetate in 20 ml of ethanol. The reaction mixture is then stirred for 20 hours at room temperature, and ethanol and excess methylamine are distilled off using a rotary evaporator. N-Methyl-2-[([(3-methoximino-2-butyl)imino]oxy)o-tolyl]-2-methoximinoacetamide having a melting point of 90–92° C. is obtained.

Example P-8: Preparation of

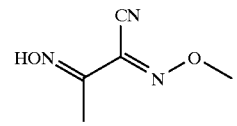

1.7 g of a 60% sodium hydride dispersion is washed with hexane and 40 ml of N,N-dimethylformamide are added. With ice-cooling, 4.5 g of 2-hydroxyimino-3-oxo-butyronitrile are added in portions to the resulting suspension. Half an hour after the evolution of hydrogen has ceased, 2.75 ml of methyl iodide are added dropwise. After stirring for 3 hours at room temperature, the reaction mixture is poured into ice-water and extracted three times with 20 ml of diethyl ether each time. The brown oil that remains after drying over sodium sulfate and removal of the solvent by evaporation is purified with ethyl acetate/hexane (1:2) on silica gel.

4.1 g of the yellow oil obtained above are stirred for 3 hours at room temperature together with 3.5 g of hydroxylamine hydrochloride in 20 ml of pyridine. The reaction mixture is poured into ice-water and the crystals that form after a short time are filtered off. Washing with water and drying yield the end product in the form of light brown crystals having a melting point of 140–145° C.

Example P-9: Preparation of

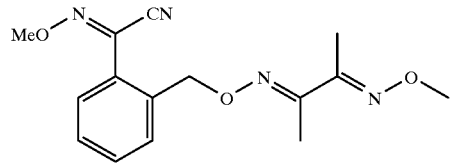

With stirring under reflux, 2.12 g of Lawesson reagent are added to a solution of 2.24 g of 2-[([(3-methoximino-2-butyl)imino]oxy)o-tolyl]-2-methoximinoacetamide in 30 ml of toluene and the resulting suspension is maintained under reflux for one hour. The reaction mixture is then concentrated using a rotary evaporator and purified by chromatography on silica gel with ethyl acetate/hexane (1:3). 2-[([(3-Methoximino-2-butyl)imino]oxy)-o-tolyl]-2-methoximinothioacetamide is obtained in the form of yellow crystals having a melting point of 149° C.

2.2 g of the thioacetamide thus obtained are stirred at 100° C. for 24 hours together with 0.9 g of potassium carbonate in 20 ml of dimethylformamide. The reaction mixture is then poured into 200 ml of ice-water and extracted twice with ethyl acetate. The organic phases are dried over magnesium sulfate and concentrated by evaporation using a rotary evaporator. The residue is purified by chromatography on silica gel with ethyl acetate/hexane (1:19). 2-[([(3-Methoximino-2-butyl)imino]oxy)o-tolyl]-2-methoximinoacetonitrile having a melting point of 75–77° C. is obtained.

The compounds of the Tables can be prepared in the above manner or analogously to one of the methods indicated.

Abbreviations: Ac=acetyl; Et=ethyl; i-Pr=isopropyl; Me=methyl; Ph=phenyl; Pr=n-propyl; Bu=n-butyl; m.p.=melting point. DS=diastereoisomer; Reg=regioisomer; "E" and "Z" relate to the configuration of the double bond. "NMR" stands for "Nuclear magnetic resonance spectrum". MS=mass spectrum. "%" stands for "percent by weight", unless the concentrations in question are given in other units.

The physical data in the Tables are the m.p. or $^1$H-NMR of $R_1/R_2$ or $R_3$ or MS molecular peak (rel. intensity) and base peak.

* The symbol "-" in column Z indicates that the compound has no Z—B substituent.

TABLE 0

(Intermediates)

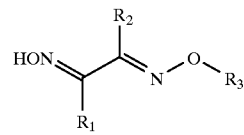

| $R_1$ | $R_2$ | $R_3$ | phys. data |
|---|---|---|---|
| CH$_3$ | CN | CH$_3$ | m.p. 140–145 |
| CH$_3$ | COOCH$_3$ | CH$_3$ | |
| CH$_3$ | COO(CH$_2$)$_3$CH$_3$ | CH$_3$ | colourless oil |
| CH$_3$ | COOC(CH$_3$)$_3$ | CH$_3$ | m.p. 111–119 |
| CH$_3$ | CON(CH$_2$CH$_3$)2 | CH$_3$ | |
| CH$_3$ | CON-morpholinyl | CH$_3$ | |
| CH$_3$ | CON-piperidinyl | CH$_3$ | |
| CH$_3$ | 2-Δ$^2$-thiazolinyl | CH$_3$ | m.p. 162–164 |
| CH$_3$ | 2-Δ$^2$-oxazolinyl | CH$_3$ | |

TABLE 0-continued (Intermediates)

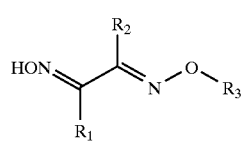

| $R_1$ | $R_2$ | $R_3$ | phys. data |
|---|---|---|---|
| CH$_3$ | (oxazoline structure) | CH$_3$ | |
| CH$_3$ | 2-O-Me-phenyl | CH$_3$ | m.p. 108–132 (E/Z) |
| CH$_3$ | 4-O-Me-phenyl | CH$_3$ | m.p. 95–98 (E/Z) |
| CH$_3$ | 4-O-Et-phenyl | CH$_3$ | m.p. 113–114 (Isom.1) m.p. 127–130 (Isom.2) |
| CH$_3$ | 4-O-Pr-phenyl | CH$_3$ | oil |
| CH$_3$ | 4-O-i-Pr-phenyl | CH$_3$ | m.p. 145–147 (Isom.1) oil (Isom.2) |
| CH$_3$ | 4-O-sec-Bu-phenyl | CH$_3$ | m.p. 146–149 (Isom.1) oil (Isom.2) |
| CH$_3$ | 4-OCF$_3$-phenyl | CH$_3$ | m.p. 184–186 |
| CH$_3$ | 2-Me-phenyl | CH$_3$ | m.p. 141–143 |
| CH$_3$ | 4-Me-phenyl | CH$_3$ | m.p. 156–157 |
| CH$_3$ | 2,4-Di-Me-phenyl | CH$_3$ | m.p. 144–146 |
| CH$_3$ | 4-Biphenyl | CH$_3$ | m.p. 184–186 (Isom.1) m.p. 132–134 (Isom 2) |

TABLE 1

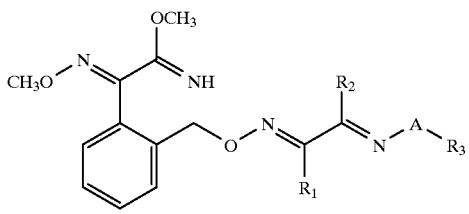

| Ex. No. | A | $R_1$ | $R_2$ | $R_3$/ NR$_3$R$_4$ | phys. data |
|---|---|---|---|---|---|
| 1.1 | NMe | Me | Me | 6-CF$_3$-2-pyridyl | |
| 1.2 | NMe | H | Me | 6-CF$_3$-2-pyridyl | |
| 1.3 | NMe | Me | Δ | 6-CF$_3$-2-pyridyl | |
| 1.4 | NMe | Me | H | phenyl | |
| 1.5 | NMe | Me | Me | phenyl | |
| 1.6 | NMe | Δ | Me | phenyl | |
| 1.7 | NMe | Me | Me | 4-CF$_3$-2-pyridyl | |
| 1.8 | NMe | H | Me | 4-CF$_3$-2-pyridyl | |
| 1.9 | NMe | Δ | Δ | phenyl | |
| 1.10 | NMe | Me | Me | 5-CF$_3$-2-pyridyl | |
| 1.11 | NMe | H | Me | 5-CF$_3$-2-pyridyl | |
| 1.12 | — | H | Me | 4-(1,2,4-triazolyl) | |
| 1.13 | — | Me | Me | 4-(1,2,4-triazolyl) | |
| 1.14 | — | Me | Δ | 4-(1,2,4-triazolyl) | |
| 1.15 | — | Me | Δ | 4-morpholinyl | |
| 1.16 | — | Me | Me | 4-morpholinyl | |
| 1.17 | — | H | Me | 4-morpholinyl | |
| 1.18 | NPh | H | Me | phenyl | |
| 1.19 | NPh | Me | Me | phenyl | |
| 1.20 | NPh | Me | Δ | phenyl | |
| 1.21 | NPh | Δ | Me | phenyl | |
| 1.22 | NMe | Me | Me | 2-nitrophenyl | |
| 1.23 | NMe | H | Me | 2-nitrophenyl | |

TABLE 1-continued

| Ex. No. | A | R₁ | R₂ | R₃/NR₃R₄ | phys. data |
|---|---|---|---|---|---|
| 1.24 | O | H | Me | Me | |
| 1.25 | O | Δ | Me | Me | |
| 1.26 | O | Me | Δ | Me | |
| 1.27 | O | Me | H | Me | |
| 1.28 | NMe | H | Me | 3-CF₃-2-pyridyl | |
| 1.29 | NMe | Me | Me | 3-CF₃-2-pyridyl | |
| 1.30 | NMe | Δ | Me | 3-CF₃-2-pyridyl | |
| 1.31 | NMe | Δ | Me | 3-nitro-2-pyridyl | |
| 1.32 | NMe | H | Me | 3-nitro-2-pyridyl | |
| 1.33 | NMe | Me | Me | 3-nitro-2-pyridyl | |
| 1.34 | NMe | Me | Me | 2-CF₃-phenyl | |
| 1.35 | NMe | Me | Δ | 2-CF₃-phenyl | |
| 1.36 | NMe | H | Me | 2-CF₃-phenyl | |
| 1.37 | NMe | Me | Me | 3-CF₃-phenyl | |
| 1.38 | NMe | Me | Δ | 3-CF₃-phenyl | |
| 1.39 | NMe | H | Me | 4-CF₃-phenyl | |
| 1.40 | NMe | Me | Me | 4-CF₃-phenyl | |
| 1.41 | NMe | Me | Me | 2-chlorophenyl | |
| 1.42 | NMe | Me | Me | 3-chlorophenyl | |
| 1.43 | NMe | H | Me | 4-chlorophenyl | |
| 1.44 | NMe | Me | Me | 4-chlorphenyl | |
| 1.45 | O | Me | Me | phenyl | |
| 1.46 | O | Me | Δ | phenyl | |
| 1.47 | O | Me | Me | benzyl | |
| 1.48 | O | Me | Me | Et | |
| 1.49 | O | H | Me | Et | |
| 1.50 | O | Δ | Me | Et | |
| 1.51 | O | Me | Δ | Et | |
| 1.52 | O | Me | H | methoxymethyl | |
| 1.53 | O | H | Me | methoxymethyl | |
| 1.54 | O | Me | Me | methoxymethyl | |
| 1.55 | O | Me | Δ | methoxymethyl | |
| 1.56 | O | Δ | Me | methoxymethyl | |
| 1.57 | O | Me | Me | ethoxymethyl | |
| 1.58 | O | H | Me | cyanomethyl | |
| 1.59 | O | Me | Me | cyanomethyl | |
| 1.60 | O | Δ | Me | cyanomethyl | |
| 1.61 | — | Me | Me | azepino | |
| 1.62 | — | Me | Me | piperidino | |
| 1.63 | — | Me | Me | pyrrolidino | |
| 1.64 | O | H | Me | tert-butyl | |
| 1.65 | O | Me | Me | tert-butyl | |
| 1.66 | O | Me | Me | propargyl | |
| 1.67 | O | Δ | Me | propargyl | |
| 1.68 | O | Me | Δ | propargyl | |
| 1.69 | O | Δ | Me | 2,2-dichloro-cyclopropylmethyl | |
| 1.70 | O | H | Me | H | |
| 1.71 | O | Me | Me | H | |
| 1.72 | O | Δ | Me | CF₃CH₂ | |
| 1.73 | O | Me | H | CF₃CH₂ | |
| 1.74 | O | Me | H | CF₃CH₂CH₂ | |
| 1.75 | O | Δ | Me | CF₃CH₂CH₂CH₂ | |
| 1.76 | NMe | Me | Me | Me | |
| 1.77 | NMe | Me | Δ | Me | |
| 1.78 | O | Δ | Me | CH₂—CCl=CH₂ | |
| 1.79 | O | Me | Me | propyl | |
| 1.80 | O | Me | Me | butyl | |
| 1.81 | O | Me | Me | hexyl | |
| 1.82 | O | Me | Me | methoxycarbonyl-methyl | |
| 1.83 | O | H | Me | methoxycarbonyl-methyl | |
| 1.84 | O | Me | Me | 3-fluorobenzyl | |
| 1.85 | O | Me | Me | 4-chlorobenzyl | |
| 1.86 | O | Me | Me | 2-chlorobenzyl | |
| 1.87 | O | Me | Me | 2-CF₃-benzyl | |
| 1.88 | O | Me | Me | 3-CF₃-benzyl | |
| 1.89 | O | Me | Me | 4-CF₃-benzyl | |
| 1.90 | O | Me | Me | 3,4-dichlorobenzyl | |
| 1.91 | O | Me | Me | 2,4,6-trimethylbenzyl | |
| 1.92 | O | Me | Me | 4-chloro-2-nitrobenzyl | |
| 1.93 | O | Me | Me | 3-methoxybenzyl | |
| 1.94 | O | Me | Me | 2-phenethyl | |
| 1.95 | O | Me | Me | 3-phenylpropyl | |
| 1.96 | O | Me | Me | 2-(4-nitrophenyl)ethyl | |
| 1.97 | O | Me | Me | 2-(2-CF₃-phenyl)ethyl | |
| 1.98 | O | Me | Me | 2-(4-methoxy-phenyl)ethyl | |
| 1.99 | O | Me | Me | 2-chloro-6-fluoro-benzyl | |
| 1.100 | O | Me | Me | 3,4-methylenedioxy-benzyl | |
| 1.101 | O | Me | Me | 2-cyanobenzyl | |
| 1.102 | O | Me | Me | 2-(4-chloro-phenyl)ethyl | |
| 1.103 | O | Me | Me | 2-(1,3-dioxo-lanyl)methyl | |
| 1.104 | O | Me | Me | 2,2,3,3-tetrafluoro-cyclobutylmethyl | |
| 1.105 | O | Me | Me | α-fluoroethoxy-carbonylmethyl | |
| 1.106 | O | Me | 2-thienyl | Me | |
| 1.107 | O | Me | 4-methyl-phenyl | Et | |
| 1.108 | NMe | Me | 4-methyl-phenyl | Me | |
| 1.109 | O | Me | CN | Et | |
| 1.110 | O | Me | CN | tert-butyl | |
| 1.111 | O | Me | CN | propargyl | |
| 1.112 | O | Me | CN | cyclopropylmethyl | |
| 1.113 | O | Me | CN | CH₂C(Cl)=CH₂ | |
| 1.114 | O | Me | CN | CH₂CH₂F | |
| 1.115 | O | Me | CN | CH₂CH₂CH₂F | |
| 1.116 | O | Me | CN | 2,2-dichlorocyclo-propylmethyl | |
| 1.117 | O | H | CN | Me | |
| 1.118 | O | CN | CN | Me | |
| 1.119 | O | Et | CN | Me | |
| 1.120 | O | Δ | CN | Me | |
| 1.121 | O | Me | COOMe | Et | |
| 1.122 | O | Me | COOMe | tert-butyl | |
| 1.123 | O | Me | COOMe | propargyl | |
| 1.124 | O | Me | COOMe | cyclopropylmethyl | |
| 1.125 | O | Me | COOMe | CH₂C(Cl)=CH₂ | |
| 1.126 | O | Me | COOMe | CH₂CH₂ | |
| 1.127 | O | Me | COOMe | CH₂CH₂CH₂CF₃ | |
| 1.128 | O | Me | COOMe | 2,2-dichlorocyclo-propylmethyl | |
| 1.129 | O | Me | COOMe | methoxymethyl | |
| 1.130 | O | H | COOMe | Me | |
| 1.131 | O | CN | COOMe | Me | |
| 1.132 | O | Δ | COOMe | Me | |
| 1.133 | O | Me | COOEt | Me | |
| 1.134 | O | Me | COOPropyl | Me | |
| 1.135 | O | Me | COOC(Me)₃ | Me | |
| 1.136 | O | Me | COOCH(Me)₂ | Me | |

TABLE 1-continued

[Structure: methyl (E)-2-[2-[[[[1-(methoxyimino)ethyl]phenyl]methoxy]imino]methyl]phenyl]-3-methoxyacrylate type backbone with R1, R2, A, R3 substituents]

| Ex. No. | A | R1 | R2 | R3/NR3R4 | phys. data |
|---|---|---|---|---|---|
| 1.137 | O | Me | COOCH2-cyclopropyl | Me | |
| 1.138 | O | Me | COOCH2CH=CH2 | Me | |
| 1.139 | O | Me | COOCH2C≡CH | Me | |
| 1.140 | O | Me | COOCH2CN | Me | |
| 1.141 | O | Me | COOCH2CF3 | Me | |
| 1.142 | O | Me | COOCH2CH2OMe | Me | |
| 1.143 | O | Me | COOCH2CH2SMe | Me | |
| 1.144 | O | Me | CON(Me)2 | Me | |
| 1.145 | O | Me | CON(Me)Et | Me | |
| 1.146 | O | Me | CON(Et)2 | Me | |
| 1.147 | O | Me | CON(Me)propyl | Me | |
| 1.148 | O | Me | CON-piperidinyl | Me | |
| 1.149 | O | Me | CON-morpholinyl | Me | |
| 1.150 | O | Me | CON-pyrrolidinyl | Me | |
| 1.151 | O | Me | CON-(4-methylpiperazinyl) | Me | |
| 1.152 | O | Me | CON-azepanyl | Me | |
| 1.153 | O | Me | CON-(2,6-dimethylmorpholinyl) | Me | |
| 1.154 | O | Me | CON(CH2CH2CN)2 | Me | |
| 1.155 | O | Me | SOMe | Me | |
| 1.156 | O | Me | SO2Me | Me | |
| 1.157 | O | Me | SOCH(Me)2 | Me | |
| 1.158 | O | Me | SO2CH(Me)2 | Me | |
| 1.159 | O | Me | SOC(Me)3 | Me | |
| 1.160 | O | Me | SO2C(Me)3 | Me | |
| 1.161 | O | Me | SO-phenyl | Me | |
| 1.162 | O | Me | SO2-phenyl | Me | |
| 1.163 | O | Me | SO2-(4-Me-phenyl) | Me | |
| 1.164 | O | Me | SO2-(4-F-phenyl) | Me | |
| 1.165 | O | Me | SO2-(4-Cl-phenyl) | Me | |
| 1.166 | O | Me | SO2-(4-OMe-phenyl) | Me | |
| 1.167 | O | Me | SO2-(4-OMe-3-NO2-phenyl) | Me | |
| 1.168 | O | Me | SO2-(3,5-dichlorophenyl) | Me | |
| 1.169 | O | H | 2-Δ²-thiazolinyl | Me | |
| 1.170 | O | CN | 2-Δ²-thiazolinyl | Me | |
| 1.171 | O | Et | 2-Δ²-thiazolinyl | Me | |
| 1.172 | O | Δ | 2-Δ²-thiazolinyl | Me | |
| 1.173 | O | Me | 2-Δ²-thiazolinyl | Et | |
| 1.174 | O | Me | 2-Δ²-thiazolinyl | tert-butyl | |
| 1.175 | O | Me | 2-Δ²-thiazolinyl | propargyl | |
| 1.176 | O | Me | 2-Δ²-thiazolinyl | cyclopropylmethyl | |
| 1.177 | O | Me | 2-Δ²-thiazolinyl | CH2C(Cl)=CH2 | |
| 1.178 | O | Me | 2-Δ²-thiazolinyl | CH2CH2F | |
| 1.179 | O | Me | 2-Δ²-thiazolinyl | CH2CH2CH2CF3 | |
| 1.180 | O | Me | 2-Δ²-thiazolinyl | 2,2-dichlorocyclopropylmethyl | |

TABLE 1-continued

Structure:

2-[(methoxyimino)(methoxy)methyl]phenyl derivative with -CH₂-O-N=C(R₁)-C(R₂)=N-A-R₃ substituent (with NH and OCH₃ groups on the phenyl-attached imino carbon)

| Ex. No. | A | R₁ | R₂ | R₃/NR₃R₄ | phys. data |
|---|---|---|---|---|---|
| 1.181 | O | Me | 2-methyl-4-(COOEt)-thiazolinyl | Me | |
| 1.182 | O | Me | 2-methyl-4,4-dimethyl... (2-methyl-5,5-dimethyl-4-COOMe-thiazolinyl) | Me | |
| 1.183 | O | Me | 2-methyl-5,6-dihydro-4H-1,3-thiazinyl | Me | |
| 1.184 | O | Me | 2-Δ²-oxazolinyl | Et | |
| 1.185 | O | Me | 2-Δ²-oxazolinyl | tert-butyl | |
| 1.186 | O | Me | 2-Δ²-oxazolinyl | propargyl | |
| 1.187 | O | Me | 2-Δ²-oxazolinyl | cyclopropylmethyl | |
| 1.188 | O | Me | 2-Δ²-oxazolinyl | CH₂C(Cl)=CH₂ | |
| 1.189 | O | Me | 2-Δ²-oxazolinyl | CH₂CH₂F | |
| 1.190 | O | Me | 2-Δ²-oxazolinyl | CH₂CH₂CH₂CF₃ | |
| 1.191 | O | Me | 2-Δ²-oxazolinyl | 2,2-dichloro-cyclopropylmethyl | |
| 1.192 | O | Me | 2,4,4-trimethyl-6-methyl-5,6-dihydro-4H-1,3-oxazinyl | Me | |
| 1.193 | O | Me | 2-methyl-4-methyl-2-oxazolinyl | Me | |
| 1.194 | O | Me | 2-methyl-4,4-dimethyl-2-oxazolinyl | Me | |
| 1.195 | O | Me | 2-pyridyl | Me | |
| 1.196 | O | Me | 3-pyridyl | Me | |
| 1.197 | O | Me | 4-pyridyl | Me | |
| 1.198 | O | Me | 2-pyrimidinyl | Me | |
| 1.199 | O | Me | 4-chloro-5-cyano-6-methylthio-2-pyrimidinyl | Me | |
| 1.200 | O | Me | 4,6-dichloro-2-pynmidinyl | Me | |
| 1.201 | O | Me | 3-methoxy-2-pyrazinyl | Me | |
| 1.202 | O | Me | 2-pyrazinyl | Me | |
| 1.203 | O | Me | 5-ethoxycarbonyl-4-trifluoromethyl-2-thiazolyl | Me | |
| 1.204 | O | Me | 2-methyl-4-ethyl-thiazolyl | Me | |

TABLE 2

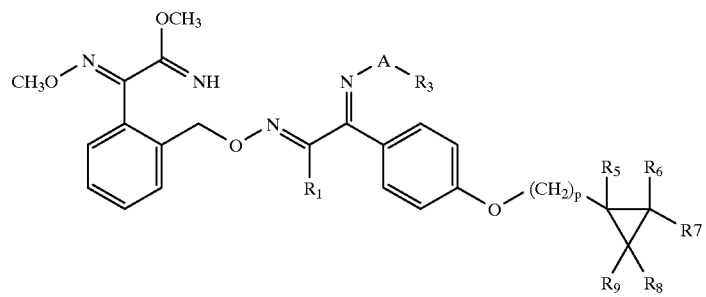

| Ex. No. | A | R₁ | R₃ | R₅ | R₆ | R₇ | R₈ | R₉ | p | phys. data |
|---|---|---|---|---|---|---|---|---|---|---|
| 2.1 | NMe | Me | Me | H | Cl | Cl | H | H | 1 | |
| 2.2 | NMe | H | Me | H | Cl | Cl | H | H | 1 | |
| 2.3 | NMe | Me | Me | H | F | F | H | H | 1 | |
| 2.4 | NMe | Me | Me | H | Br | Br | H | H | 1 | |
| 2.5 | NMe | Me | Et | H | F | F | H | H | 1 | |
| 2.6 | NPh | Me | Me | H | Cl | Cl | H | H | 1 | |
| 2.7 | NPh | H | Me | H | Cl | Cl | H | H | 1 | |
| 2.8 | NPh | Me | Et | H | Cl | Cl | H | H | 1 | |
| 2.9 | O | H | Me | H | Cl | Cl | H | H | 1 | |
| 2.10 | O | Me | Me | H | F | F | H | H | 1 | |
| 2.11 | O | H | Me | H | F | F | H | H | 1 | |
| 2.12 | O | Me | H | H | F | F | H | H | 1 | |
| 2.13 | O | Me | C₃H₇ | H | Cl | Cl | H | H | 1 | |
| 2.14 | O | Me | Δ | H | Cl | Cl | H | H | 1 | |
| 2.15 | O | Δ | Me | H | Cl | Cl | H | H | 1 | |
| 2.16 | O | Me | Et | H | Cl | Cl | H | H | 1 | |
| 2.17 | O | H | Me | H | Br | Br | H | H | 1 | |
| 2.18 | O | Me | Me | H | Cl | Cl | H | H | 2 | |
| 2.19 | O | H | Me | H | Cl | Cl | H | H | 2 | |
| 2.20 | O | Me | Me | H | F | F | H | H | 2 | |
| 2.21 | O | Me | Me | Me | Cl | Cl | H | H | 1 | |
| 2.22 | O | Me | Me | H | Cl | Cl | Me | Me | 1 | |

TABLE 3

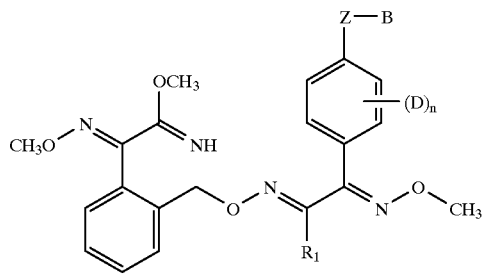

| Ex. No. | R₁ | Z* | n | B or D | phys. data |
|---|---|---|---|---|---|
| 3.1 | Me | — | 1 | 3-CF₃ | |
| 3.2 | Me | — | 1 | 4-chloro | |
| 3.3 | Me | — | 1 | 3-chloro | |
| 3.4 | Me | — | 1 | 2-fluoro | |
| 3.5 | Me | O | 0 | Me | |
| 3.6 | Me | — | 1 | 4-bromo | |
| 3.7 | Me | — | 1 | 4-fluoro | |
| 3.8 | Me | — | 2 | 3-F-5-CF₃ | |
| 3.9 | Me | — | O | | |
| 3.10 | Me | — | 1 | 3-bromo | |
| 3.11 | Me | — | 2 | 3,4-methylenedioxy | |
| 3.12 | SMe | — | 1 | 4-methyl | |
| 3.13 | Et | — | 1 | 4-methyl | |
| 3.14 | Me | — | 1 | 4-isobutyl | |
| 3.15 | Me | O | 0 | 2,2,2-trifluoroethyl | |

TABLE 3-continued

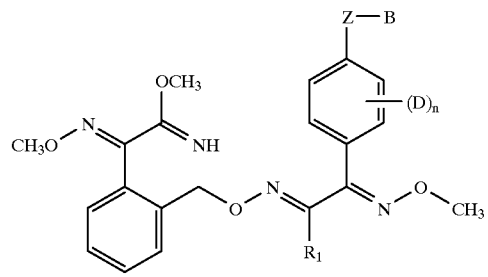

| Ex. No. | R₁ | Z* | n | B or D | phys. data |
|---|---|---|---|---|---|
| 3.16 | CN | — | 1 | 4-methyl | |
| 3.17 | CN | — | 1 | 4-chloro | |
| 3.18 | CN | — | 2 | 3,4-dichloro | |
| 3.19 | CN | O | 0 | CF₃ | |
| 3.20 | CN | — | 1 | 3-CF₃ | |
| 3.21 | CN | — | 1 | 4-fluoro | |
| 3.22 | Me | O | 0 | phenyl | |
| 3.23 | Me | O | 0 | CH₂CH=CCl₂ | |
| 3.24 | Me | O | 0 | CH₂CH=CF₂ | |
| 3.25 | Me | O | 0 | CH₂CH=CBr₂ | |
| 3.26 | Me | O | 0 | 4-Cl-phenyl | |
| 3.27 | Me | O | 0 | 4-F-phenyl | |
| 3.28 | Me | S | 0 | phenyl | |
| 3.29 | Me | CH₂O | 0 | phenyl | |
| 3.30 | Me | O | 0 | 3,3-dimethylallyl | |

TABLE 3-continued

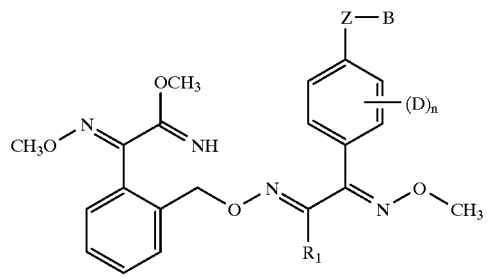

| Ex. No. | $R_1$ | $Z^*$ | n | B or D | phys. data |
|---|---|---|---|---|---|
| 3.31 | Me | O | 0 | 2-methylallyl | |
| 3.32 | Me | O | 0 | 3-methyl | |
| 3.33 | Me | OCH$_2$ | 0 | 3-CF$_3$-phenyl | |
| 3.34 | Me | CH$_2$O | 0 | 3-CF$_3$-phenyl | |
| 3.35 | Me | OCH$_2$ | 0 | C$_6$H$_{11}$ | |
| 3.36 | Me | OCH$_2$ | 0 | 3-CH$_3$-phenyl | |
| 3.37 | Me | OCH$_2$ | 0 | 3-OCH$_3$-phenyl | |
| 3.38 | Me | OCH$_2$ | 0 | 4-CF$_3$-phenyl | |
| 3.39 | Me | OCH$_2$ | 0 | 4-Br-phenyl | |
| 3.40 | Me | OCH$_2$ | 0 | 4-CH$_3$-phenyl | |
| 3.41 | Me | OCH$_2$ | 0 | 4-OCH$_3$-phenyl | |
| 3.42 | Me | OCH$_2$ | 0 | 2-CF$_3$-phenyl | |
| 3.43 | Me | OCH$_2$ | 0 | 2-F-phenyl | |

TABLE 3-continued

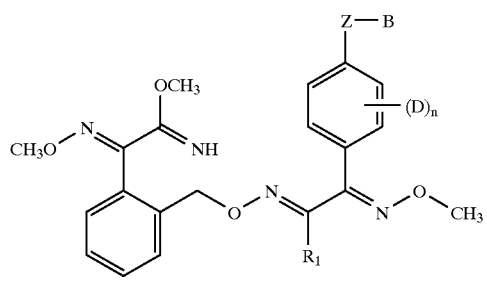

| Ex. No. | $R_1$ | $Z^*$ | n | B or D | phys. data |
|---|---|---|---|---|---|
| 3.44 | Me | OCH$_2$ | 0 | 2-Cl-phenyl | |
| 3.45 | Me | OCH$_2$ | 0 | 2-Br-phenyl | |
| 3.46 | Me | OCH$_2$ | 0 | 3-F-phenyl | |
| 3.47 | Me | OCH$_2$ | 0 | 3-Cl-phenyl | |
| 3.48 | Me | OCH$_2$ | 0 | 3-Br-phenyl | |
| 3.49 | CN | — | — | H | |
| 3.50 | CN | — | 1 | 4-tert-butyl | |
| 3.51 | CN | O | 0 | phenyl | |
| 3.52 | Me | O | 0 | CF$_2$CHF$_2$ | |
| 3.53 | Me | O | 0 | CF$_2$CHCl$_2$ | |
| 3.54 | Me | O | 0 | CF$_2$CHBr$_2$ | |
| 3.55 | Me | — | 1 | 4-tert-butyl | |
| 3.56 | Me | — | 1 | 4-CF$_3$ | |
| 3.57 | Me | OCH$_2$ | 0 | 4-Cl-phenyl | |

TABLE 4

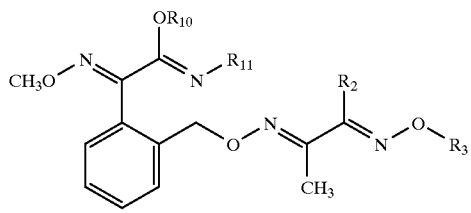

| Ex. No. | $R_{10}$ | $R_{11}$ | $R_2$ | $R_3$ | phys. data |
|---|---|---|---|---|---|
| 4.1 | Me | H | Me | Me | 107–109° C. |
| 4.2 | Et | H | Me | Me | 348 (12), 116 |
| 4.3 | Me | Me | Me | Me | 348 (1), 72 |
| 4.4 | Me | H | Me | methoxymethyl | |
| 4.5 | Et | H | Me | methoxymethyl | |
| 4.6 | Me | Me | Me | methoxymethyl | |
| 4.7 | Me | H | Me | cyanomethyl | |
| 4.8 | Et | H | Me | cyanomethyl | |
| 4.9 | Me | Me | Me | cyanomethyl | |
| 4.10 | Me | H | Me | allyl | |
| 4.11 | Et | H | Me | allyl | |
| 4.12 | Me | Me | Me | allyl | |
| 4.13 | Me | H | Me | methallyl | |
| 4.14 | Et | H | Me | methallyl | |
| 4.15 | Me | Me | Me | methallyl | |
| 4.16 | Me | H | Me | propargyl | |
| 4.17 | Et | H | Me | propargyl | |
| 4.18 | Me | Me | Me | propargyl | |
| 4.19 | Me | H | Me | 2,2-dichlorocyclopropylmethyl | |

TABLE 4-continued

| Ex. No. | $R_{10}$ | $R_{11}$ | $R_2$ | $R_3$ | phys. data |
|---|---|---|---|---|---|
| 4.20 | Et | H | Me | 2,2-dichlorocyclopropylmethyl | |
| 4.21 | Me | Me | Me | 2,2-dichlorocyclopropylmethyl | |
| 4.22 | Me | H | Me | $CH_2CF_3$ | |
| 4.23 | Et | H | Me | $CH_2CF_3$ | |
| 4.24 | Me | Me | Me | $CF_2CF_3$ | |
| 4.25 | Me | H | Me | $CH_2CH_2CF_3$ | |
| 4.26 | Et | H | Me | $CH_2CH_2CF_3$ | |
| 4.27 | Me | Me | Me | $CH_2CH_2CF_3$ | |
| 4.28 | Me | H | Me | $CH_2CH_2CH_2CF_3$ | |
| 4.29 | Et | H | Me | $CH_2CH_2CH_2CF_3$ | |
| 4.30 | Me | Me | Me | $CH_2CH_2CH_2CF_3$ | |
| 4.31 | Me | H | Me | $CH_2C(Cl)=CH_2$ | |
| 4.32 | Et | H | Me | $CH_2C(Cl)=CH_2$ | |
| 4.33 | Me | Me | Me | $CH_2C(Cl)=CH_2$ | |
| 4.34 | Me | H | Me | cyclopropylmethyl | |
| 4.35 | Et | H | Me | cyclopropylmethyl | |
| 4.36 | Me | Me | Me | cyclopropylmethyl | |
| 4.37 | Me | H | Me | $CH_2CH_2F$ | |
| 4.38 | Et | H | Me | $CH_2CH_2F$ | |
| 4.39 | Me | Me | Me | $CH_2CH_2F$ | |
| 4.40 | Me | H | CN | Me | |
| 4.41 | Et | H | CN | Me | |
| 4.42 | Me | Me | CN | Me | |
| 4.43 | Me | H | CN | $CH_2CF_3$ | |
| 4.44 | Et | H | CN | $CH_2CF_3$ | |
| 4.45 | Me | Me | CN | $CH_2CF_3$ | |
| 4.46 | Me | H | COOMe | Me | |
| 4.47 | Et | H | COOMe | Me | |
| 4.48 | Me | Me | COOMe | Me | |
| 4.49 | Me | H | COOMe | $CH_2CF_3$ | |
| 4.50 | Et | H | COOMe | $CH_2CF_3$ | |
| 4.51 | Me | Me | COOMe | $CH_2CF_3$ | |
| 4.52 | Me | H | COObutyl | Me | |
| 4.53 | Et | H | COObutyl | Me | |
| 4.54 | Me | Me | COObutyl | Me | |
| 4.55 | Me | H | 2-$\Delta^2$-thiazolinyl | Me | |
| 4.56 | Et | H | 2-$\Delta^2$-thiazolinyl | Me | |
| 4.57 | Me | Me | 2-$\Delta^2$-thiazolinyl | Me | |
| 4.58 | Me | H | 2-$\Delta^2$-thiazolinyl | $CH_2CF_3$ | |
| 4.59 | Et | H | 2-$\Delta^2$-thiazolinyl | $CH_2CF_3$ | |
| 4.60 | Me | Me | 2-$\Delta^2$-thiazolinyl | $CH_2CF_3$ | |
| 4.61 | Me | H | 2-$\Delta^2$-oxazolinyl | Me | |
| 4.62 | Et | H | 2-$\Delta^2$-oxazolinyl | Me | |
| 4.63 | Me | Me | 2-$\Delta^2$-oxazolinyl | Me | |
| 4.64 | Me | H | 2-$\Delta^2$-oxazolinyl | $CH_2CF_3$ | |
| 4.65 | Et | H | 2-$\Delta^2$-oxazolinyl | $CH_2CF_3$ | |
| 4.66 | Me | Me | 2-$\Delta^2$-oxazolinyl | $CH_2CF_3$ | |
| 4.67 | Me | H | 2-thiazolyl | Me | |
| 4.68 | Et | H | 2-thiazolyl | Me | |
| 4.69 | Me | Me | 2-thiazolyl | Me | |
| 4.70 | Me | OH | Me | Me | |
| 4.71 | Me | OMe | Me | Me | |

TABLE 5

Structure: general formula with R10, R11, R1, Z-B, (D)n substituents on a bis-oxime-ether scaffold (CH3O-N=C(-)-C(=N-R11)-O-R10 on one phenyl; -CH2-O-N=C(R1)-C(=N-OCH3)- on phenyl bearing Z-B and (D)n)

| Ex. No. | $R_{10}$ | $R_{11}$ | $R_1$ | Z* | n | B or D | phys. data |
|---|---|---|---|---|---|---|---|
| 5.1 | Me | H | Me | — | 1 | 4-methyl | |
| 5.2 | Et | H | Me | — | 1 | 4-methyl | |
| 5.3 | Me | Me | Me | — | 1 | 4-methyl | |
| 5.4 | Me | H | Me | — | 1 | 2-methyl | |
| 5.5 | Et | H | Me | — | 1 | 2-methyl | |
| 5.6 | Me | Me | Me | — | 1 | 2-methyl | |
| 5.7 | Me | H | Me | O | 0 | allyl | 2.09 |
| 5.8 | Et | H | Me | O | 0 | allyl | |
| 5.9 | Me | Me | Me | O | 0 | allyl | |
| 5.10 | Me | H | Me | O | 0 | propargyl | |
| 5.11 | Et | H | Me | O | 0 | propargyl | |
| 5.12 | Me | Me | Me | O | 0 | propargyl | |
| 5.13 | Me | H | Me | O | 0 | ethyl | |
| 5.14 | Et | H | Me | O | 0 | ethyl | |
| 5.15 | Me | Me | Me | O | 0 | ethyl | |
| 5.16 | Me | H | CN | — | 1 | 2-chloro | |
| 5.17 | Et | H | CN | — | 1 | 2-chloro | |
| 5.18 | Me | Me | CN | — | 1 | 2-chloro | |
| 5.19 | Me | H | Me | $OCH_2$ | 0 | phenyl | |
| 5.20 | Et | H | Me | $OCH_2$ | 0 | phenyl | |
| 5.21 | Me | Me | Me | $OCH_2$ | 0 | phenyl | |
| 5.22 | Me | H | Me | O | 0 | n-propyl | |
| 5.23 | Et | H | Me | O | 0 | n-propyl | |
| 5.24 | Me | Me | Me | O | 0 | n-propyl | |
| 5.25 | Me | H | Me | $OCH_2$ | 0 | 4-F-phenyl | |
| 5.26 | Et | H | Me | $OCH_2$ | 0 | 4-F-phenyl | |
| 5.27 | Me | Me | Me | $OCH_2$ | 0 | 4-F-phenyl | |
| 5.28 | Me | H | Me | S | 0 | Me | |
| 5.29 | Et | H | Me | S | 0 | Me | |
| 5.30 | Me | Me | Me | S | 0 | Me | |
| 5.31 | Me | H | Me | SO | 0 | Me | |
| 5.32 | Et | H | Me | SO | 0 | Me | |
| 5.33 | Me | Me | Me | SO | 0 | Me | |
| 5.34 | Me | H | Me | $SO_2$ | 0 | Me | |
| 5.35 | Et | H | Me | $SO_2$ | 0 | Me | |
| 5.36 | Me | Me | Me | $SO_2$ | 0 | Me | |
| 5.37 | Me | H | Me | S | 0 | Et | |
| 5.38 | Et | H | Me | S | 0 | Et | |
| 5.39 | Me | Me | Me | S | 0 | Et | |
| 5.40 | Me | H | Me | SO | 0 | Et | |
| 5.41 | Et | H | Me | SO | 0 | Et | |
| 5.42 | Me | Me | Me | SO | 0 | Et | |
| 5.43 | Me | H | Me | $SO_2$ | 0 | Et | |
| 5.44 | Et | H | Me | $SO_2$ | 0 | Et | |
| 5.45 | Me | Me | Me | $SO_2$ | 0 | Et | |
| 5.46 | Me | H | Me | S | 0 | $n-C_3H_7$ | |
| 5.47 | Et | H | Me | S | 0 | $n-C_3H_7$ | |
| 5.48 | Me | Me | Me | S | 0 | $n-C_3H_7$ | |
| 5.49 | Me | H | Me | SO | 0 | $n-C_3H_7$ | |
| 5.50 | Et | H | Me | SO | 0 | $n-C_3H_7$ | |
| 5.51 | Me | Me | Me | SO | 0 | $n-C_3H_7$ | |
| 5.52 | Me | H | Me | $SO_2$ | 0 | $n-C_3H_7$ | |
| 5.53 | Et | H | Me | $SO_2$ | 0 | $n-C_3H_7$ | |
| 5.54 | Me | Me | Me | $SO_2$ | 0 | $n-C_3H_7$ | |
| 5.55 | Me | H | CN | O | 0 | Me | |
| 5.56 | Et | H | CN | O | 0 | Me | |
| 5.57 | Me | Me | CN | O | 0 | Me | |
| 5.58 | Me | H | Me | — | 1 | 4-ethyl | |
| 5.59 | Et | H | Me | — | 1 | 4-ethyl | |
| 5.60 | Me | Me | Me | — | 1 | 4-ethyl | |
| 5.61 | Me | H | Me | — | 1 | 4-n-propyl | |
| 5.62 | Et | H | Me | — | 1 | 4-n-propyl | |
| 5.63 | Me | Me | Me | — | 1 | 4-n-propyl | |
| 5.64 | Me | OH | Me | O | 0 | 4-n-Propyl | |
| 5.65 | Me | OMe | Me | O | 0 | 4-n-Propyl | |
| 5.66 | Me | OH | Me | O | 0 | Ethyl | |
| 5.67 | Me | OMe | Me | O | 0 | Ethyl | |

TABLE 6

| Ex. No. | $R_{10}$ | $R_{11}$ | $R_6$ | $R_7$ | phys. data |
|---|---|---|---|---|---|
| 6.1 | Me | H | Cl | Cl | |

TABLE 6-continued
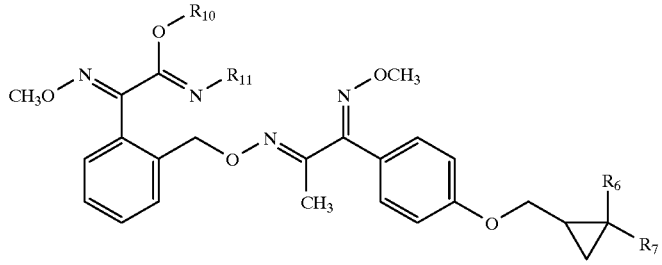
| Ex. No. | R₁₀ | R₁₁ | R₆ | R₇ | phys. data |
|---------|-----|-----|-----|-----|------------|
| 6.2 | Et | H | Cl | Cl | |
| 6.3 | Me | Me | Cl | Cl | |
| 6.4 | Me | H | Br | Br | |
| 6.5 | Et | H | Br | Br | |
| 6.6 | Me | Me | Br | Br | |
| 6.7 | Me | H | F | F | |
| 6.8 | Et | H | F | F | |
| 6.9 | Me | Me | F | F | |
| 6.10 | Me | H | H | H | |
| 6.11 | Et | H | H | H | |
| 6.12 | Me | Me | H | H | |
TABLE 7
204 compounds of the formula
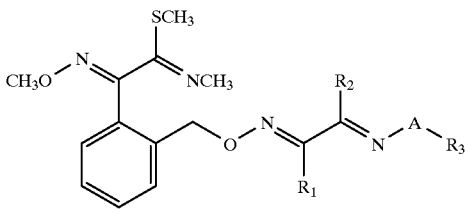
wherein A, $R_1$, $R_2$ and $R_3$ are as defined for the corresponding compounds of Table 1.
TABLE 8
22 compounds of the formula
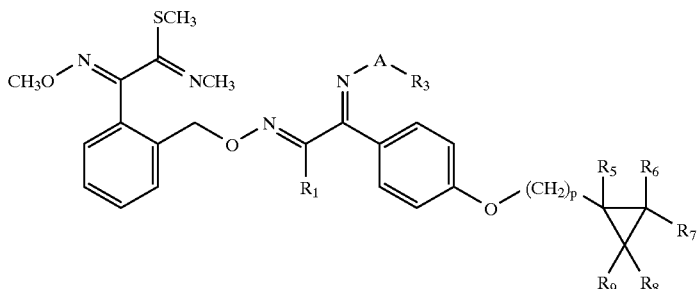
wherein A, $R_1$, $R_3$, $R_5$ to $R_9$ and p are as defined for the corresponding compounds of Table 2.

TABLE 9

57 compounds of the formula

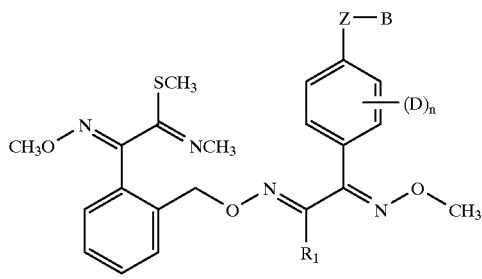

wherein $R_1$, Z, n, B and D are as defined for the corresponding compounds of Table 3.

TABLE 10

204 compounds of the formula

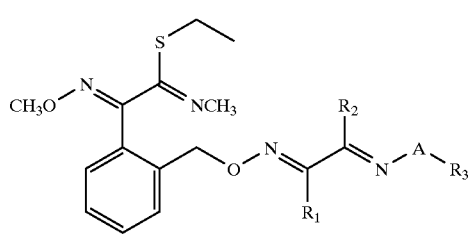

wherein A, $R_1$, $R_2$ and $R_3/NR_3R_4$ are as defined for the corresponding compounds of Table 1.

TABLE 11

22 compounds of the formula

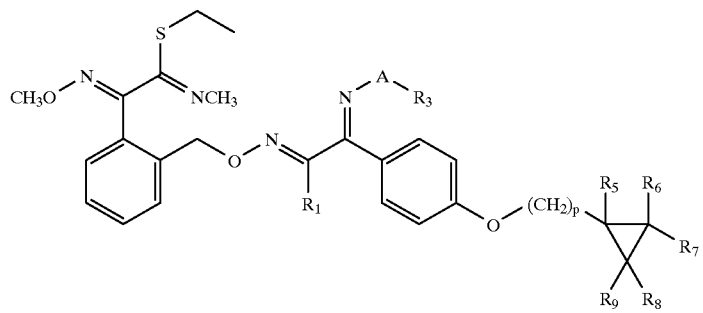

wherein A, $R_1$, $R_3$, $R_5$, $R_6$, $R_7$, $R_8$, $R_9$ and p are as defined for the corresponding compounds of Table 2.

TABLE 12

57 compounds of the formula

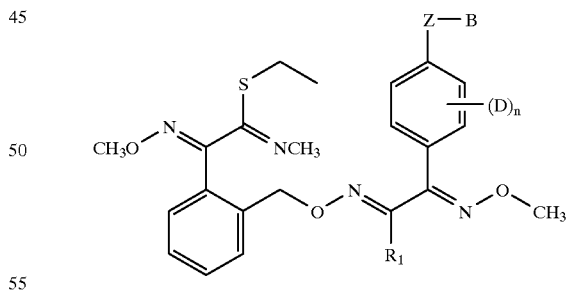

wherein $R_1$, Z, n, B and D are as defined for the corresponding compounds of Table 3.

TABLE 13

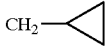

| Ex. No. | R₁₀ | R₁₁ | R₂ | R₃ | phys. data |
|---|---|---|---|---|---|
| 13.1 | Me | H | Me | Me | 350 (2), 116 |
| 13.2 | Me | Me | Me | Me | 364 (1), 72 |
| 13.3 | Et | Me | Me | Me | 378 (2), 72 |
| 13.4 | n-Pr | Me | Me | Me | |
| 13.5 | n-Bu | Me | Me | Me | |
| 13.6 | Et | Et | Me | Me | 392 (1), 72 |
| 13.7 | allyl | Me | Me | Me | |
| 13.8 | methallyl | Me | Me | Me | |
| 13.9 | benzyl | Me | Me | Me | |
| 13.10 | CH₂— | | Me | Me | Me | |
| 13.11 | CH₂—O—CH₃ | Me | Me | Me | |
| 13.12 | CH₂COOMe | Me | Me | Me | |
| 13.13 | CH(Me)COOMe | Me | Me | Me | |
| 13.14 | CH(Me)COO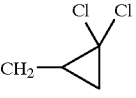 | | Me | Me | Me | |
| 13.15 | Me | H | Me | CH₂OCH₃ | |
| 13.16 | Me | Me | Me | CH₂OCH₃ | |
| 13.17 | Et | Me | Me | CH₂OCH₃ | |
| 13.18 | allyl | Me | Me | CH₂OCH₃ | |
| 13.19 | Me | Me | Me | CH₂CN | |
| 13.20 | Et | Me | Me | CH₂CN | |
| 13.21 | allyl | Me | Me | CH₂CN | |
| 13.22 | Me | Me | Me | allyl | |
| 13.23 | Et | Me | Me | allyl | |
| 13.24 | allyl | Me | Me | allyl | |
| 13.25 | Me | Me | Me | methallyl | |
| 13.26 | Et | Me | Me | methallyl | |
| 13.27 | allyl | Me | Me | methallyl | |
| 13.28 | Me | Me | Me | propargyl | |
| 13.29 | Et | Me | Me | propargyl | |
| 13.30 | allyl | Me | Me | propargyl | |
| 13.31 | Me | Me | Me | 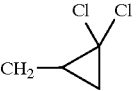 | |
| 13.32 | Et | Me | Me | 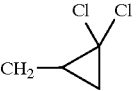 | |
| 13.33 | CH₂COOMe | Me | Me | 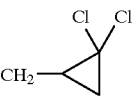 | |
| 13.34 | Me | H | Me | CH₂CF₃ | |
| 13.35 | Me | Me | Me | CH₂CF₃ | |
| 13.36 | Et | Me | Me | CH₂CF₃ | |
| 13.37 | allyl | Me | Me | CH₂CF₃ | |
| 13.38 | CH₂OCH₃ | Me | Me | CH₂CF₃ | |
| 13.39 | Me | Me | Me | CH₂CH₂CF₃ | |

TABLE 13-continued

[Structure: CH₃O-N= attached to C bearing S-R₁₀ and =N-R₁₁ group, connected to phenyl ring with ortho -CH₂-O-N=C(R₂)-C(CH₃)=N-O-R₃]

| Ex. No. | R₁₀ | R₁₁ | R₂ | R₃ | phys. data |
|---|---|---|---|---|---|
| 13.40 | Et | Me | Me | CH₂CH₂CF₃ | |
| 13.41 | allyl | Me | Me | CH₂CH₂CF₃ | |
| 13.42 | n-Pr | Me | Me | CH₂CH₂CF₃ | |
| 13.43 | Me | Me | Me | CH₂CH₂CH₂CF₃ | |
| 13.44 | Et | Me | Me | CH₂CH₂CH₂CF₃ | |
| 13.45 | Me | H | Me | CH₂C(Cl)=CH₂ | |
| 13.46 | Me | Me | Me | CH₂C(Cl)=CH₂ | |
| 13.47 | Et | Me | Me | CH₂C(Cl)=CH₂ | |
| 13.48 | allyl | Me | Me | CH₂C(Cl)=CH₂ | |
| 13.49 | Me | Me | Me | CH₂-cyclopropyl | |
| 13.50 | Et | Me | Me | CH₂-cyclopropyl | |
| 13.51 | Me | Me | Me | CH₂CH₂F | |
| 13.52 | Et | Me | Me | CH₂CH₂F | |
| 13.53 | Me | H | CN | Me | |
| 13.54 | Me | Me | CN | Me | |
| 13.55 | Et | Me | CN | Me | |
| 13.56 | i-Pr | Me | CN | Me | |
| 13.57 | allyl | Me | CN | Me | |
| 13.58 | benzyl | Me | CN | Me | |
| 13.59 | Me | Me | CN | CH₂CF₃ | |
| 13.60 | Et | Me | CN | CH₂CF₃ | |
| 13.61 | allyl | Me | CN | CH₂CF₃ | |
| 13.62 | Me | H | COOMe | Me | |
| 13.63 | Me | Me | COOMe | Me | |
| 13.64 | Et | Me | COOMe | Me | |
| 13.65 | n-Bu | Me | COOMe | Me | |
| 13.66 | allyl | Me | COOMe | Me | |
| 13.67 | Me | Me | COOMe | Me | |
| 13.68 | Et | Me | COOMe | Me | |
| 13.69 | allyl | Me | COOMe | Me | |
| 13.70 | Me | Me | COOBu | Me | |
| 13.71 | Et | Me | COOBu | Me | |
| 13.72 | allyl | Me | COOBu | Me | |
| 13.73 | Me | Me | 2-Δ²-thiazolinyl | Me | |
| 13.74 | Et | Me | 2-Δ²-thiazolinyl | Me | |
| 13.75 | allyl | Me | 2-Δ²-thiazolinyl | Me | |
| 13.76 | n-Pr | Me | 2-Δ²-thiazolinyl | Me | |
| 13.77 | CH(Me)COOMe | Me | 2-Δ²-thiazolinyl | Me | |
| 13.78 | Me | H | 2-Δ²-oxazolinyl | Me | |
| 13.79 | Me | Me | 2-Δ²-oxazolinyl | Me | |
| 13.80 | Et | Me | 2-Δ²-oxazolinyl | Me | |
| 13.81 | i-Pr | Me | 2-Δ²-oxazolinyl | Me | |
| 13.82 | allyl | Me | 2-Δ²-oxazolinyl | Me | |
| 13.83 | CH₂-cyclopropyl | Me | 2-Δ²-oxazolinyl | Me | |
| 13.84 | Me | Me | 2-thiazolyl | Me | |
| 13.85 | Et | Me | 2-thiazolyl | Me | |
| 13.86 | allyl | Me | 2-thiazolyl | Me | |
| 13.87 | Me | OMe | Me | Me | |
| 13.88 | Et | OMe | Me | Me | |

TABLE 14

| Ex. No. | $R_{10}$ | $R_{11}$ | $R_1$ | $Z^*$ | n | B or D | phys. data |
|---|---|---|---|---|---|---|---|
| 14.1 | Me | H | Me | — | 1 | 4-methyl | |
| 14.2 | Me | Me | Me | — | 1 | 4-methyl | |
| 14.3 | Et | Me | Me | — | 1 | 4-methyl | |
| 14.4 | n-Pr | Me | Me | — | 1 | 4-methyl | |
| 14.5 | n-Bu | Me | Me | — | 1 | 4-methyl | |
| 14.6 | i-Pr | Me | Me | — | 1 | 4-methyl | |
| 14.7 | allyl | Me | Me | — | 1 | 4-methyl | |
| 14.8 | methallyl | Me | Me | — | 1 | 4-methyl | |
| 14.9 | benzyl | Me | Me | — | 1 | 4-methyl | |
| 14.10 |  | Me | Me | — | 1 | 4-methyl | |
| 14.11 | $CH_2OCH_3$ | Me | Me | — | 1 | 4-methyl | |
| 14.12 | $CH_2COOMe$ | Me | Me | — | 1 | 4-methyl | |
| 14.13 | CH(Me)COOMe | Me | Me | — | 1 | 4-methyl | |
| 14.14 | CH(Me)COO-iBu | Me | Me | — | 1 | 4-methyl | |
| 14.15 | Me | Me | Me | O | 0 | allyl | |
| 14.16 | Et | Me | Me | O | 0 | allyl | |
| 14.17 | n-Pr | Me | Me | O | 0 | allyl | |
| 14.18 | Me | Me | Me | O | 0 | propargyl | |
| 14.19 | Et | Me | Me | O | 0 | propargyl | |
| 14.20 | n-Bu | Me | Me | O | 0 | propargyl | |
| 14.21 | Me | Me | Me | O | 0 | ethyl | |
| 14.22 | Et | Me | Me | O | 0 | ethyl | |
| 14.23 | allyl | Me | Me | O | 0 | ethyl | |
| 14.24 | Me | Me | CN | — | 1 | 2-chloro | |
| 14.25 | Et | Me | CN | — | 1 | 2-chloro | |
| 14.26 | allyl | Me | CN | — | 1 | 2-chloro | |
| 14.27 | Me | Me | Me | $OCH_2$ | 0 | phenyl | |
| 14.28 | Et | Me | Me | $OCH_2$ | 0 | phenyl | |
| 14.29 | allyl | Me | Me | $OCH_2$ | 0 | phenyl | |
| 14.30 | i-Pr | Me | Me | $OCH_2$ | 0 | phenyl | |
| 14.31 | Me | Me | Me | O | 0 | n-Pr | |
| 14.32 | Et | Me | Me | O | 0 | n-Pr | |
| 14.33 | allyl | Me | Me | O | 0 | n-Pr | |
| 14.34 | Me | Me | Me | $OCH_2$ | 0 | 4-F-phenyl | |
| 14.35 | Et | Me | Me | $OCH_2$ | 0 | 4-F-phenyl | |
| 14.36 | allyl | Me | Me | $OCH_2$ | 0 | 4-F-phenyl | |
| 14.37 | Me | Me | Me | S | 0 | Me | |
| 14.38 | Et | Me | Me | S | 0 | Me | |
| 14.39 | allyl | Me | Me | S | 0 | Me | |
| 14.40 | n-Pr | Me | Me | S | 0 | Me | |
| 14.41 | i-Pr | Me | Me | S | 0 | Me | |
| 14.42 | Me | Me | Me | SO | 0 | Me | |
| 14.43 | Et | Me | Me | SO | 0 | Me | |
| 14.44 | allyl | Me | Me | SO | 0 | Me | |
| 14.45 | Me | Me | Me | $SO_2$ | 0 | Me | |
| 14.46 | Et | Me | Me | $SO_2$ | 0 | Me | |
| 14.47 | allyl | Me | Me | $SO_2$ | 0 | Me | |
| 14.48 | Me | H | Me | S | 0 | Et | |
| 14.49 | Me | Me | Me | S | 0 | Et | |
| 14.50 | Et | Me | Me | S | 0 | Et | |
| 14.51 | benzyl | Me | Me | S | 0 | Et | |
| 14.52 | allyl | Me | Me | S | 0 | Et | |

TABLE 14-continued

[Structure: compound with CH3O-N=, S-R10, N-R11 groups on benzene ring connected via CH2-O-N= to another group with R1, N-OCH3, and phenyl with (D)n and Z-B substituents]

| Ex. No. | R10 | R11 | R1 | Z* | n | B or D | phys. data |
|---------|-----|-----|-----|-----|---|--------|------------|
| 14.53 | CH2-cyclopropyl | Me | Me | S | 0 | Et | |
| 14.54 | Me | Me | Me | SO | 0 | Et | |
| 14.55 | Et | Me | Me | SO | 0 | Et | |
| 14.56 | allyl | Me | Me | SO | 0 | Et | |
| 14.57 | Me | Me | Me | SO2 | 0 | Et | |
| 14.58 | Et | Me | Me | SO2 | 0 | Et | |
| 14.59 | allyl | Me | Me | SO2 | 0 | Et | |
| 14.60 | CH2OCH3 | Me | Me | SO2 | 0 | Et | |
| 14.61 | Me | Me | Me | S | 0 | n-C3H7 | |
| 14.62 | Et | Me | Me | S | 0 | n-C3H7 | |
| 14.63 | allyl | Me | Me | S | 0 | n-C3H7 | |
| 14.64 | Me | Me | Me | SO | 0 | n-C3H7 | |
| 14.65 | Et | Me | Me | SO | 0 | n-C3H7 | |
| 14.66 | allyl | Me | Me | SO | 0 | n-C3H7 | |
| 14.67 | Me | Me | Me | SO2 | 0 | n-C3H7 | |
| 14.68 | Et | Me | Me | SO2 | 0 | n-C3H7 | |
| 14.69 | allyl | Me | Me | SO2 | 0 | n-C3H7 | |
| 14.70 | Me | Me | CN | O | 0 | Me | |
| 14.71 | Et | Me | CN | O | 0 | Me | |
| 14.72 | allyl | Me | CN | O | 0 | Me | |
| 14.73 | n-Pr | Me | CN | O | 0 | Me | |
| 14.74 | Me | H | Me | — | 1 | 4-ethyl | |
| 14.75 | Me | Me | Me | — | 1 | 4-ethyl | |
| 14.76 | Et | Me | Me | — | 1 | 4-ethyl | |
| 14.77 | i-Pr | Me | Me | — | 1 | 4-ethyl | |
| 14.78 | benzyl | Me | Me | — | 1 | 4-ethyl | |
| 14.79 | CH2COOMe | Me | Me | — | 1 | 4-ethyl | |
| 14.80 | Me | H | Me | — | 1 | 4-n-Pr | |
| 14.81 | Me | Me | Me | — | 1 | 4-n-Pr | |
| 14.82 | Et | Me | Me | — | 1 | 4-n-Pr | |
| 14.83 | n-Bu | Me | Me | — | 1 | 4-n-Pr | |
| 14.84 | allyl | Me | Me | — | 1 | 4-n-Pr | |
| 14.85 | CH2-cyclopropyl | Me | Me | — | 1 | 4-n-Pr | |

TABLE 15

[Structure: compound with CH3O-N=, S-R10, N-R11 groups on benzene ring connected via CH2-O-N= to another group with CH3, N-OCH3, and phenyl with O-CH2-cyclopropyl bearing R6 and R7]

| Ex. No. | R10 | R11 | R6 | R7 | phys. data |
|---------|-----|-----|-----|-----|------------|
| 15.1 | Me | H | Cl | Cl | |
| 15.2 | Me | Me | Cl | Cl | |

TABLE 15-continued

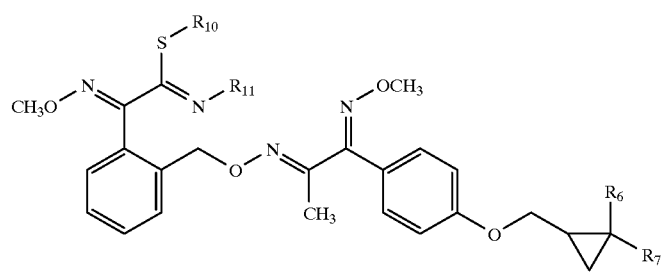

| Ex. No. | $R_{10}$ | $R_{11}$ | $R_6$ | $R_7$ | phys. data |
|---|---|---|---|---|---|
| 15.3 | Et | Me | Cl | Cl | |
| 15.4 | n-Pr | Me | Cl | Cl | |
| 15.5 | i-Pr | Me | Cl | Cl | |
| 15.6 | allyl | Me | Cl | Cl | |
| 15.7 | methallyl | Me | Cl | Cl | |
| 15.8 | CH$_2$–⊲ | Me | Cl | Cl | |
| 15.9 | CH$_2$OCH$_3$ | Me | Cl | Cl | |
| 15.10 | benzyl | Me | Cl | Cl | |
| 15.11 | CH$_2$COOMe | Me | Cl | Cl | |
| 15.12 | CH(Me)COOMe | Me | Cl | Cl | |
| 15.13 | Me | Me | Br | Br | |
| 15.14 | Et | Me | Br | Br | |
| 15.15 | allyl | Me | Br | Br | |
| 15.16 | Me | H | F | F | |
| 15.17 | Me | Me | F | F | |
| 15.18 | Et | Me | F | F | |
| 15.19 | n-Pr | Me | F | F | |
| 15.20 | i-Pr | Me | F | F | |
| 15.21 | allyl | Me | F | F | |
| 15.22 | methallyl | Me | F | F | |
| 15.23 | Me | Me | H | H | |
| 15.24 | Et | Me | H | H | |
| 15.25 | allyl | Me | H | H | |
| 15.26 | benzyl | Me | H | H | |
| 15.27 | CH$_2$COOMe | Me | H | H | |

TABLE 16

204 compounds of the formula

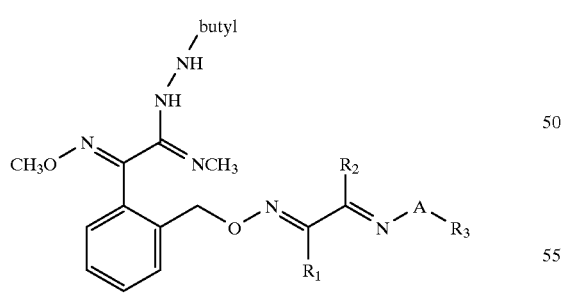

wherein A, $R_1$, $R_2$ and $R_3$/NR$_3$R$_4$ are as defined for the corresponding compounds of Table 1.

TABLE 17

22 compounds of the formula

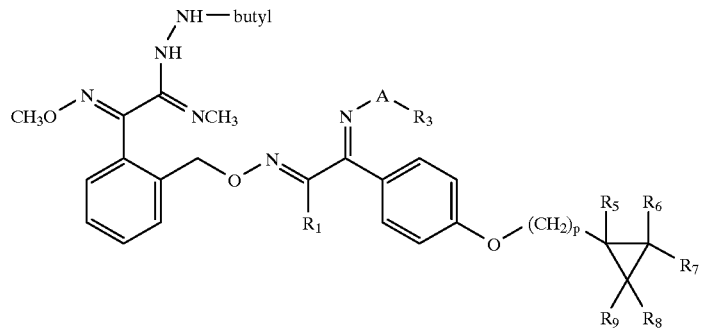

wherein A, $R_1$, $R_3$, $R_5$, $R_6$, $R_7$, $R_8$, $R_9$ and p are as defined for the corresponding compounds of Table 2.

TABLE 18

57 compounds of the formula

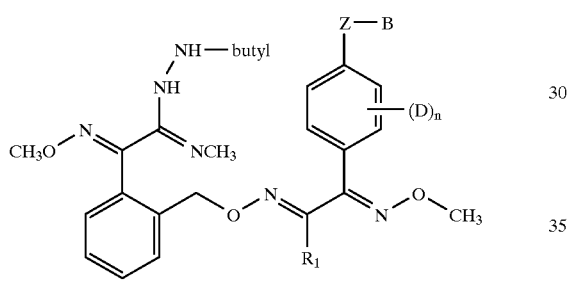

wherein $R_1$, Z, n, B and D are as defined for the corresponding compounds of Table 3.

TABLE 19

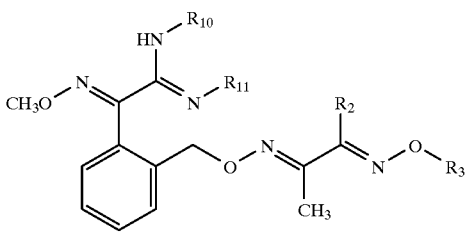

| Ex. No. | $R_{10}$ | $R_{11}$ | $R_2$ | $R_3$ | phys. data |
|---|---|---|---|---|---|
| 19.1 | Me | Me | Me | Me | |
| 19.2 | Et | Me | Me | Me | |
| 19.3 | NHMe | Me | Me | Me | |
| 19.4 | NHEt | Me | Me | Me | |
| 19.5 | NHPr | Me | Me | Me | |
| 19.6 | NHBu | Me | Me | Me | |
| 19.7 | Nt—Bu | Me | Me | Me | |
| 19.8 | NHCH$_2$CF$_3$ | Me | Me | Me | |
| 19.9 | H | OCH$_2$CH=CH$_2$ | Me | Me | |
| 19.10 | Me | OH | Me | Me | |
| 19.11 | NHMe | Me | Me | CH$_2$OCH$_3$ | |
| 19.12 | NHBu | Me | Me | CH$_2$OCH$_3$ | |

TABLE 19-continued

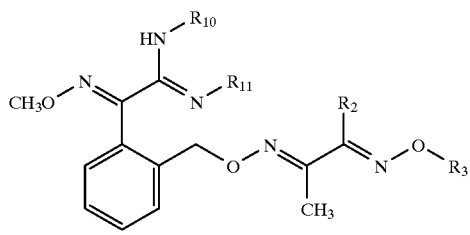

| Ex. No. | R₁₀ | R₁₁ | R₂ | R₃ | phys. data |
|---|---|---|---|---|---|
| 19.13 | NHMe | Me | Me | CH₂CN | |
| 19.14 | NHEt | Me | Me | CH₂CN | |
| 19.15 | NHMe | Me | Me | allyl | |
| 19.16 | NHPr | Me | Me | allyl | |
| 19.17 | NHMe | Me | Me | methallyl | |
| 19.18 | NHBu | Me | Me | methallyl | |
| 19.19 | NHMe | Me | Me | propargyl | |
| 19.20 | NHBu | Me | Me | propargyl | |
| 19.21 | NHMe | Me | Me | CH₂-(2,2-dichlorocyclopropyl) | |
| 19.22 | NHEt | Me | Me | CH₂-(2,2-dichlorocyclopropyl) | |
| 19.23 | NHPr | Me | Me | CH₂-(2,2-dichlorocyclopropyl) | |
| 19.24 | NHBu | Me | Me | CH₂-(2,2-dichlorocyclopropyl) | |
| 19.25 | NHMe | Me | Me | CH₂CF₃ | |
| 19.26 | NHEt | Me | Me | CH₂CF₃ | |
| 19.27 | NHBu | Me | Me | CH₂CF₃ | |
| 19.28 | Nt—Bu | Me | Me | CH₂CF₃ | |
| 19.29 | NHCH₂CF₃ | Me | Me | CH₂CF₃ | |
| 19.30 | Me | OH | Me | CH₂CF₃ | |
| 19.31 | NHMe | Me | Me | CH₂CH₂CF₃ | |
| 19.32 | NHBu | Me | Me | CH₂CH₂CF₃ | |
| 19.33 | NHMe | Me | Me | CH₂CH₂CH₂CF₃ | |
| 19.34 | NHBu | Me | Me | CH₂CH₂CH₂CF₃ | |
| 19.35 | NHMe | Me | Me | CH₂C(Cl)=CH₂ | |
| 19.36 | NHEt | Me | Me | CH₂C(Cl)=CH₂ | |
| 19.37 | NHBu | Me | Me | CH₂C(Cl)=CH₂ | |
| 19.38 | NHMe | Me | Me | CH₂-cyclopropyl | |
| 19.39 | NHBu | Me | Me | CH₂-cyclopropyl | |
| 19.40 | NHMe | Me | Me | CH₂CH₂F | |
| 19.41 | NHBu | Me | Me | CH₂CH₂F | |
| 19.42 | NHMe | Me | CN | Me | |
| 19.43 | NHEt | Me | CN | Me | |
| 19.44 | NHBu | Me | CN | Me | |
| 19.45 | Nt—Bu | Me | CN | Me | |
| 19.46 | NHMe | Me | CN | CH₂CF₃ | |
| 19.47 | NHBu | Me | CN | CH₂CF₃ | |
| 19.48 | NHMe | Me | COOMe | Me | |

TABLE 19-continued

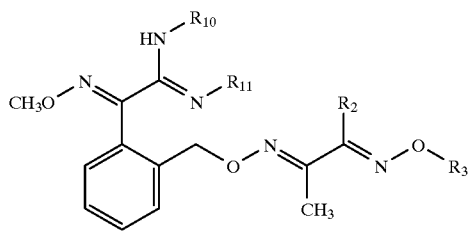

| Ex. No. | R10 | R11 | R2 | R3 | phys. data |
|---|---|---|---|---|---|
| 19.49 | NHEt | Me | COOMe | Me | |
| 19.50 | NHBu | Me | COOMe | Me | |
| 19.51 | NHMe | Me | COOMe | $CH_2CF_3$ | |
| 19.52 | NHEt | Me | COOMe | $CH_2CF_3$ | |
| 19.53 | NHBu | Me | COOMe | $CH_2CF_3$ | |
| 19.54 | Nt—Bu | Me | COOMe | $CH_2CF_3$ | |
| 19.55 | NHMe | Me | COOBu | Me | |
| 19.56 | NHBu | Me | COOBu | Me | |
| 19.57 | NHMe | Me | 2-$\Delta^2$-thiazolinyl | Me | |
| 19.58 | NHEt | Me | 2-$\Delta^2$-thiazolinyl | Me | |
| 19.59 | NHPr | Me | 2-$\Delta^2$-thiazolinyl | Me | |
| 19.60 | NHBu | Me | 2-$\Delta^2$-thiazolinyl | Me | |
| 19.61 | Nt—Bu | Me | 2-$\Delta^2$-thiazolinyl | Me | |
| 19.62 | NHMe | Me | 2-$\Delta^2$-oxazolinyl | Me | |
| 19.63 | NHEt | Me | 2-$\Delta^2$-oxazolinyl | Me | |
| 19.64 | NHBu | Me | 2-$\Delta^2$-oxazolinyl | Me | |
| 19.65 | NHMe | Me | 2-Thiazolyl | Me | |
| 19.66 | NHBu | Me | 2-Thiazolyl | Me | |
| 19.67 | Me | H | Me | Me | |
| 19.68 | Me | OMe | Me | Me | |

TABLE 20

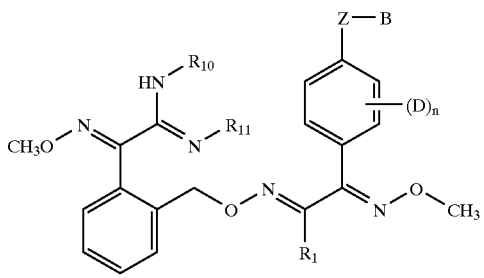

| Ex. No. | R10 | R11 | R1 | Z* | n | B or D | phys. data |
|---|---|---|---|---|---|---|---|
| 20.1 | Me | Me | Me | — | 1 | 4-methyl | |
| 20.2 | Et | Me | Me | — | 1 | 4-methyl | |
| 20.3 | NHMe | Me | Me | — | 1 | 4-methyl | |
| 20.4 | NHEt | Me | Me | — | 1 | 4-methyl | |
| 20.5 | NHPr | Me | Me | — | 1 | 4-methyl | |
| 20.6 | NHBu | Me | Me | — | 1 | 4-methyl | |
| 20.7 | Nt—Bu | Me | Me | — | 1 | 4-methyl | |
| 20.8 | $NHCH_2CF_3$ | Me | Me | — | 1 | 4-methyl | |
| 20.9 | H | $OCH_2CH=CH_2$ | Me | — | 1 | 4-methyl | |
| 20.10 | Me | OH | Me | — | 1 | 4-methyl | |
| 20.11 | NHMe | Me | Me | — | 1 | 2-methyl | |
| 20.12 | NHEt | Me | Me | — | 1 | 2-methyl | |
| 20.13 | NHBu | Me | Me | — | 1 | 2-methyl | |
| 20.14 | NHMe | Me | Me | O | 0 | allyl | |

TABLE 20-continued

| Ex. No. | R₁₀ | R₁₁ | R₁ | Z* | n | B or D | phys. data |
|---|---|---|---|---|---|---|---|
| 20.15 | NHBu | Me | Me | O | 0 | allyl | |
| 20.16 | NHMe | Me | Me | O | 0 | propargyl | |
| 20.17 | NHBu | Me | Me | O | 0 | propargyl | |
| 20.18 | NHMe | Me | Me | O | 0 | ethyl | |
| 20.19 | NHEt | Me | Me | O | 0 | ethyl | |
| 20.20 | NHBu | Me | Me | O | 0 | ethyl | |
| 20.21 | NHMe | Me | CN | — | 1 | 2-chloro | |
| 20.22 | NHBu | Me | CN | — | 1 | 2-chloro | |
| 20.23 | NHt—Bu | Me | CN | — | 1 | 2-chloro | |
| 20.24 | NHMe | Me | Me | OCH₂ | 0 | phenyl | |
| 20.25 | NHBu | Me | Me | OCH₂ | 0 | phenyl | |
| 20.26 | NHMe | Me | Me | O | 0 | n-Pr | |
| 20.27 | NHBu | Me | Me | O | 0 | n-Pr | |
| 20.28 | NHMe | Me | Me | OCH₂ | 0 | 4-F-phenyl | |
| 20.29 | NHBu | Me | Me | OCH₂ | 0 | 4-F-phenyl | |
| 20.30 | NHMe | Me | Me | S | 0 | Me | |
| 20.31 | NHEt | Me | Me | S | 0 | Me | |
| 20.32 | NHPr | Me | Me | S | 0 | Me | |
| 20.33 | NHBu | Me | Me | S | 0 | Me | |
| 20.34 | Nt—Bu | Me | Me | S | 0 | Me | |
| 20.35 | NHMe | Me | Me | SO | 0 | Me | |
| 20.36 | NHBu | Me | Me | SO | 0 | Me | |
| 20.37 | NHMe | Me | Me | SO₂ | 0 | Me | |
| 20.38 | NHBu | Me | Me | SO₂ | 0 | Me | |
| 20.39 | Et | Me | Me | S | 0 | Et | |
| 20.40 | NHMe | Me | Me | S | 0 | Et | |
| 20.41 | NHEt | Me | Me | S | 0 | Et | |
| 20.42 | NHBu | Me | Me | S | 0 | Et | |
| 20.43 | Nt—Bu | Me | Me | S | 0 | Et | |
| 20.44 | NHMe | Me | Me | SO | 0 | Et | |
| 20.45 | NHBu | Me | Me | SO | 0 | Et | |
| 20.46 | NHMe | Me | Me | SO₂ | 0 | Et | |
| 20.47 | NHBu | Me | Me | SO₂ | 0 | Et | |
| 20.48 | NHMe | Me | Me | S | 0 | n-Pr | |
| 20.49 | NHBu | Me | Me | S | 0 | n-Pr | |
| 20.50 | Nt—Bu | Me | Me | S | 0 | n-Pr | |
| 20.51 | NHMe | Me | Me | SO | 0 | n-Pr | |
| 20.52 | NHBu | Me | Me | SO | 0 | n-Pr | |
| 20.53 | NHMe | Me | Me | SO₂ | 0 | n-Pr | |
| 20.54 | NHBu | Me | Me | SO₂ | 0 | n-Pr | |
| 20.55 | NHMe | Me | CN | O | 0 | Me | |
| 20.56 | NHBu | Me | CN | O | 0 | Me | |
| 20.57 | NHMe | Me | Me | — | 1 | 4-ethyl | |
| 20.58 | NHBu | Me | Me | — | 1 | 4-ethyl | |
| 20.59 | NHMe | Me | Me | — | 1 | 4-n-Pr | |
| 20.60 | NHBu | Me | Me | — | 1 | 4-n-Pr | |
| 20.61 | Me | H | Me | — | 1 | 2-methyl | |
| 20.62 | Me | OMe | Me | — | 1 | 2-methyl | |
| 20.63 | Me | H | Me | — | 1 | 4-tert.butyl | |
| 20.64 | Me | OMe | Me | — | 1 | 4-tert.butyl | |

TABLE 21

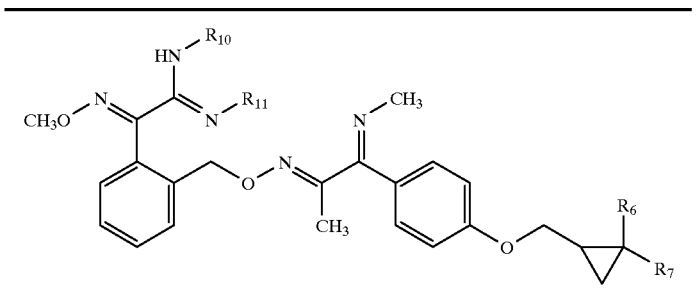

| Ex. No. | R₁₀ | R₁₁ | R₆ | R₇ | phys. data |
|---|---|---|---|---|---|
| 21.1 | Me | Me | Cl | Cl | |
| 21.2 | Et | Me | Cl | Cl | |
| 21.3 | NHMe | Me | Cl | Cl | |
| 21.4 | NHEt | Me | Cl | Cl | |
| 21.5 | NHPr | Me | Cl | Cl | |
| 21.6 | NHBu | Me | Cl | Cl | |
| 21.7 | Nt-Bu | Me | Cl | Cl | |
| 21.8 | NHCH₂CF₃ | Me | Cl | Cl | |
| 21.9 | H | OCH₂CH=CH₂ | Cl | Cl | |
| 21.10 | Me | O | Cl | Cl | |
| 21.11 | NHMe | Me | Br | Br | |
| 21.12 | NHEt | Me | Br | Br | |
| 21.13 | NHPr | Me | Br | Br | |
| 21.14 | NHBu | Me | Br | Br | |
| 21.15 | NHMe | Me | F | F | |
| 21.16 | NHEt | Me | F | F | |
| 21.17 | NHBu | Me | F | F | |
| 21.18 | NHCH₂CF₃ | Me | F | F | |
| 21.19 | NHMe | Me | H | H | |
| 21.20 | NHBu | Me | H | H | |
| 21.21 | NHCH₂CF₃ | Me | H | H | |

TABLE 22

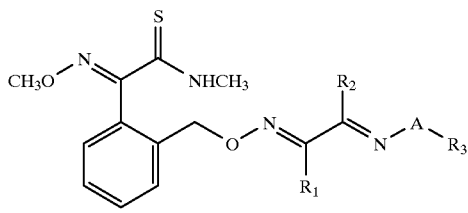

| Ex. No. | A | R₁ | R₂ | R₃/NR₃R₄ | phys. data |
|---|---|---|---|---|---|
| 22.1 | NMe | Me | Me | 6-CF₃-2-pyridyl | |
| 22.2 | NMe | H | Me | 6-CF₃-2-pyridyl | |
| 22.3 | NMe | Me | Δ | 6-CF₃-2-pyridyl | |
| 22.4 | NMe | Me | H | phenyl | |
| 22.5 | NMe | Me | Me | phenyl | |
| 22.6 | NMe | Δ | Me | phenyl | |
| 22.7 | NMe | Me | Me | 4-CF₃-2-pyridyl | |
| 22.8 | NMe | H | Me | 4-CF₃-2-pyridyl | |
| 22.9 | NMe | Δ | Δ | phenyl | |
| 22.10 | NMe | Me | Me | 5-CF₃-2-pyridyl | |
| 22.11 | NMe | H | Me | 5-CF₃-2-pyridyl | |
| 22.12 | — | H | Me | 4-(1,2,4-triazolyl) | |
| 22.13 | — | Me | Me | 4-(1,2,4-triazolyl) | |
| 22.14 | — | Me | Δ | 4-(1,2,4-triazolyl) | |
| 22.15 | — | Me | Δ | 4-morpholinyl | |
| 22.16 | — | Me | Me | 4-morpholinyl | |
| 22.17 | — | H | Me | 4-morpholinyl | |
| 22.18 | NPh | H | Me | phenyl | |
| 22.19 | NPh | Me | Me | phenyl | |
| 22.20 | NPh | Me | Δ | phenyl | |
| 22.21 | NPh | Δ | Me | phenyl | |
| 22.22 | NMe | Me | Me | 2-nitrophenyl | |
| 22.23 | NMe | H | Me | 2-nitrophenyl | |

TABLE 22-continued

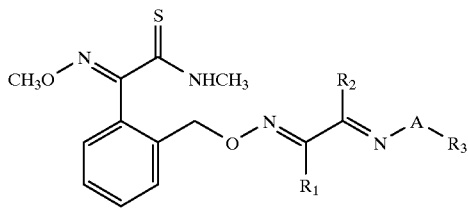

| Ex. No. | A | R₁ | R₂ | R₃/NR₃R₄ | phys. data |
|---|---|---|---|---|---|
| 22.24 | O | H | Me | Me | |
| 22.25 | O | Δ | Me | Me | |
| 22.26 | O | Me | Δ | Me | |
| 22.27 | O | Me | H | Me | |
| 22.28 | NMe | H | Me | 3-CF₃-2-pyridyl | |
| 22.29 | NMe | Me | Me | 3-CF₃-2-pyridyl | |
| 22.30 | NMe | Δ | Me | 3-CF₃-2-pyridyl | |
| 22.31 | NMe | Δ | Me | 3-nitro-2-pyridyl | |
| 22.32 | NMe | H | Me | 3-nitro-2-pyridyl | |
| 22.33 | NMe | Me | Me | 3-nitro-2-pyridyl | |
| 22.34 | NMe | Me | Me | 2-CF₃-phenyl | |
| 22.35 | NMe | Me | Δ | 2-CF₃-phenyl | |
| 22.36 | NMe | H | Me | 2-CF₃-phenyl | |
| 22.37 | NMe | Me | Me | 3-CF₃-phenyl | |
| 22.38 | NMe | Me | Δ | 3-CF₃-phenyl | |
| 22.39 | NMe | H | Me | 4-CF₃-phenyl | |
| 22.40 | NMe | Me | Me | 4-CF₃-phenyl | |
| 22.41 | NMe | Me | Me | 2-chlorophenyl | |
| 22.42 | NMe | Me | Me | 3-chlorophenyl | |
| 22.43 | NMe | H | Me | 4-chlorophenyl | |
| 22.44 | NMe | Me | Me | 4-chlorophenyl | |
| 22.45 | O | Me | Me | phenyl | |
| 22.46 | O | Me | Δ | phenyl | |
| 22.47 | O | Me | Me | benzyl | |
| 22.48 | O | Me | Me | Et | |
| 22.49 | O | H | Me | Et | |
| 22.50 | O | Δ | Me | Et | |
| 22.51 | O | Me | Δ | Et | |
| 22.52 | O | Me | H | methoxymethyl | |
| 22.53 | O | H | Me | methoxymethyl | |
| 22.54 | O | Me | Me | methoxymethyl | |
| 22.55 | O | Me | Δ | methoxymethyl | |
| 22.56 | O | Δ | Me | methoxymethyl | |
| 22.57 | O | Me | Me | ethoxymethyl | |
| 22.58 | O | H | Me | cyanomethyl | |
| 22.59 | O | Me | Me | cyanomethyl | |
| 22.60 | O | Δ | Me | cyanomethyl | |
| 22.61 | — | Me | Me | azepino | |
| 22.62 | — | Me | Me | piperidino | |
| 22.63 | — | Me | Me | pyrrolidino | |
| 22.64 | O | H | Me | tert-butyl | |
| 22.65 | O | Me | Me | tert-butyl | |
| 22.66 | O | Me | Me | propargyl | |
| 22.67 | O | Δ | Me | propargyl | |
| 22.68 | O | Me | Δ | propargyl | |
| 22.69 | O | Δ | Me | 2,2-dichlorocyclopropylmethyl | |
| 22.70 | O | H | Me | H | |
| 22.71 | O | Me | Me | H | |
| 22.72 | O | Δ | Me | CF₃CH₂ | |
| 22.73 | O | Me | H | CF₃CH₂ | |
| 22.74 | O | Me | H | CF₃CH₂CH₂ | |
| 22.75 | O | Δ | Me | CF₃CH₂CH₂CH₂ | |
| 22.76 | NMe | Me | Me | Me | |
| 22.77 | NMe | Me | Δ | Me | |
| 22.78 | O | Δ | Me | CH₂—CCl=CH₂ | |
| 22.79 | O | Me | Me | propyl | |
| 22.80 | O | Me | Me | butyl | |
| 22.81 | O | Me | Me | hexyl | |
| 22.82 | O | Me | Me | methoxycarbonylmethyl | |
| 22.83 | O | H | Me | methoxycarbonylmethyl | |
| 22.84 | O | Me | Me | 3-fluorobenzyl | |
| 22.85 | O | Me | Me | 4-chlorobenzyl | |
| 22.86 | O | Me | Me | 2-chlorobenzyl | |
| 22.87 | O | Me | Me | 2-CF₃-benzyl | |
| 22.88 | O | Me | Me | 3-CF₃-benzyl | |

TABLE 22-continued

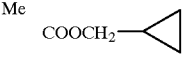

| Ex. No. | A | R₁ | R₂ | R₃/NR₃R₄ | phys. data |
|---|---|---|---|---|---|
| 22.89 | O | Me | Me | 4-CF₃-benzyl | |
| 22.90 | O | Me | Me | 3,4-dichlorobenzyl | |
| 22.91 | O | Me | Me | 2,4,6-trimethylbenzyl | |
| 22.92 | O | Me | Me | 4-chloro-2-nitrobenzyl | |
| 22.93 | O | Me | Me | 3-methoxybenzyl | |
| 22.94 | O | Me | Me | 2-phenethyl | |
| 22.95 | O | Me | Me | 3-phenylpropyl | |
| 22.96 | O | Me | Me | 2-(4-nitrophenyl)ethyl | |
| 22.97 | O | Me | Me | 2-(2-CF₃-phenyl)ethyl | |
| 22.98 | O | Me | Me | 2-(4-methoxyphenyl)ethyl | |
| 22.99 | O | Me | Me | 2-chloro-6-fluorobenzyl | |
| 22.100 | O | Me | Me | 3,4-methylenedioxybenzyl | |
| 22.101 | O | Me | Me | 2-cyanobenzyl | |
| 22.102 | O | Me | Me | 2-(4-chlorophenyl)ethyl | |
| 22.103 | O | Me | Me | 2-(22,3-dioxolanyl)methyl | |
| 22.104 | O | Me | Me | 2,2,3,3-tetrafluorocyclobutylmethyl | |
| 22.105 | O | Me | Me | α-fluoroethoxycarbonylmethyl | |
| 22.106 | O | Me | 2-thienyl | Me | |
| 22.107 | O | Me | 4-methylphenyl | Et | |
| 22.108 | NMe | Me | 4-methylphenyl | Me | |
| 22.109 | O | Me | CN | Et | |
| 22.110 | O | Me | CN | tert-butyl | |
| 22.111 | O | Me | CN | propargyl | |
| 22.112 | O | Me | CN | cyclopropylmethyl | |
| 22.113 | O | Me | CN | CH₂C(Cl)=CH₂ | |
| 22.114 | O | M | CN | CH₂CH₂F | |
| 22.115 | O | Me | CN | CH₂CH₂CH₂F | |
| 22.116 | O | Me | CN | 2,2-dichlorocyclopropylmethyl | |
| 22.117 | O | H | CN | Me | |
| 22.118 | O | CN | CN | Me | |
| 22.119 | O | Et | CN | Me | |
| 22.120 | O | Δ | CN | Me | |
| 22.121 | O | Me | COOMe | Et | |
| 22.122 | O | Me | COOMe | tert-butyl | |
| 22.123 | O | Me | COOMe | propargyl | |
| 22.124 | O | Me | COOMe | cyclopropylmethyl | |
| 22.125 | O | Me | COOMe | CH₂C(Cl)=CH₂ | |
| 22.126 | O | Me | COOMe | CH₂CH₂F | |
| 22.127 | O | Me | COOMe | CH₂CH₂CH₂CF₃ | |
| 22.128 | O | Me | COOMe | 2,2-dichlorocyclopropylmethyl | |
| 22.129 | O | Me | COOMe | methoxymethyl | |
| 22.130 | O | H | COOMe | Me | |
| 22.131 | O | CN | COOMe | Me | |
| 22.132 | O | Δ | COOMe | Me | |
| 22.133 | O | Me | COOEt | Me | |
| 22.134 | O | Me | COOpropyl | Me | |
| 22.135 | O | Me | COOC(Me)₃ | Me | |
| 22.136 | O | Me | COOCH(Me)₂ | Me | |
| 22.137 | O | Me | COOCH₂-▷ | Me | |
| 22.138 | O | Me | COOCH₂CH=CH₂ | Me | |
| 22.139 | O | Me | COOCH₂C≡CH | Me | |
| 22.140 | O | Me | COOCH₂CN | Me | |
| 22.141 | O | Me | COOCH₂CF₃ | Me | |
| 22.142 | O | Me | COOCH₂CH₂OMe | Me | |
| 22.143 | O | Me | COOCH₂CH₂SMe | Me | |
| 22.144 | O | Me | CON(Me)₂ | Me | |
| 22.145 | O | Me | CON(Me)Et | Me | |
| 22.146 | O | Me | CON(Et)₂ | Me | |
| 22.147 | O | Me | CON(Me)propyl | Me | |

TABLE 22-continued
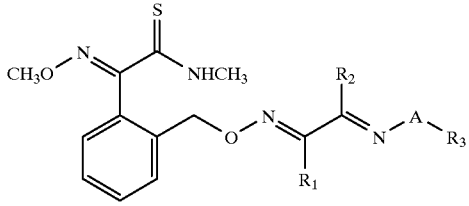
| Ex. No. | A | R₁ | R₂ | R₃/NR₃R₄ | phys. data |
|---|---|---|---|---|---|
| 22.148 | O | Me |  | Me | |
| 22.149 | O | Me |  | Me | |
| 22.150 | O | Me |  | Me | |
| 22.151 | O | Me | 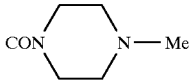 | Me | |
| 22.152 | O | Me | 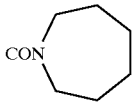 | Me | |
| 22.153 | O | Me | 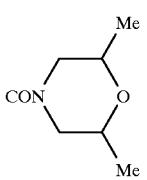 | Me | |
| 22.154 | O | Me | CON(CH₂CH₂CN)₂ | Me | |
| 22.155 | O | Me | SOMe | Me | |
| 22.156 | O | Me | SO₂Me | Me | |
| 22.157 | O | Me | SOCH(Me)₂ | Me | |
| 22.158 | O | Me | SO₂CH(Me)₂ | Me | |
| 22.159 | O | Me | SOC(Me)₃ | Me | |
| 22.160 | O | Me | SO₂C(Me)₃ | Me | |
| 22.161 | O | Me | 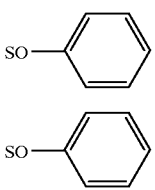 | Me | |
| 22.162 | O | Me | 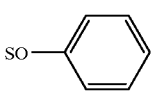 | Me | |

TABLE 22-continued

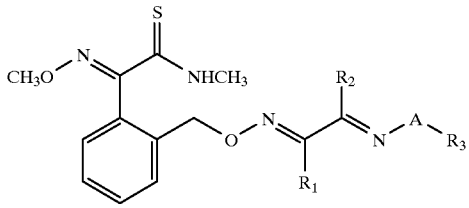

| Ex. No. | A | R₁ | R₂ | R₃/NR₃R₄ | phys. data |
|---|---|---|---|---|---|
| 22.163 | O | Me |  | Me | |
| 22.164 | O | Me |  | Me | |
| 22.165 | O | Me |  | Me | |
| 22.166 | O | Me | 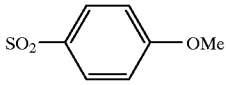 | Me | |
| 22.167 | O | Me | 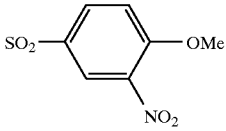 | Me | |
| 22.168 | O | Me | 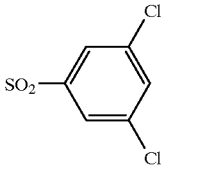 | Me | |
| 22.169 | O | H | 2-Δ²-thiazolinyl | Me | |
| 22.170 | O | CN | 2-Δ²-thiazolinyl | Me | |
| 22.171 | O | Et | 2-Δ²-thiazolinyl | Me | |
| 22.172 | O | Δ | 2-Δ²-thiazolinyl | Me | |
| 22.173 | O | Me | 2-Δ²-thiazolinyl | Et | |
| 22.174 | O | Me | 2-Δ²-thiazolinyl | tert-butyl | |
| 22.175 | O | Me | 2-Δ²-thiazolinyl | propargyl | |
| 22.176 | O | Me | 2-Δ²-thiazolinyl | cyclopropylmethyl | |
| 22.177 | O | Me | 2-Δ²-thiazolinyl | CH₂C(Cl)=CH₂ | |
| 22.178 | O | Me | 2-Δ²-thiazolinyl | CH₂CH₂F | |
| 22.179 | O | Me | 2-Δ²-thiazolinyl | CH₂CH₂CH₂CF₃ | |
| 22.180 | O | Me | 2-Δ²-thiazolinyl | 2,2-dichlorocyclopropylmethyl | |
| 22.181 | O | Me | 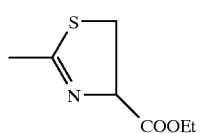 | Me | |

TABLE 22-continued

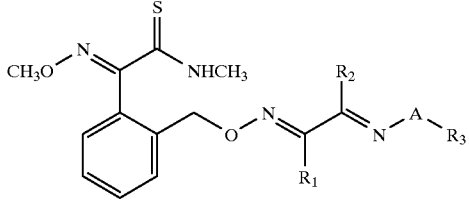

| Ex. No. | A | R₁ | R₂ | R₃/NR₃R₄ | phys. data |
|---|---|---|---|---|---|
| 22.182 | O | Me | 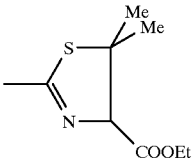 | Me | |
| 22.183 | O | Me | 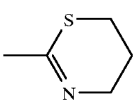 | Me | |
| 22.184 | O | Me | 2-Δ²-oxazolinyl | Et | |
| 22.185 | O | Me | 2-Δ²-oxazolinyl | tert-butyl | |
| 22.186 | O | Me | 2-Δ²-oxazolinyl | propargyl | |
| 22.187 | O | Me | 2-Δ²-oxazolinyl | cyclopropylmethyl | |
| 22.188 | O | Me | 2-Δ²-oxazolinyl | CH₂C(Cl)=CH₂ | |
| 22.189 | O | Me | 2-Δ²-oxazolinyl | CH₂CH₂F | |
| 22.190 | O | Me | 2-Δ²-oxazolinyl | CH₂CH₂CH₂CF₃ | |
| 22.191 | O | Me | 2-Δ²-oxazolinyl | 2,2-dichlorocyclopropylmethyl | |
| 22.192 | O | Me | 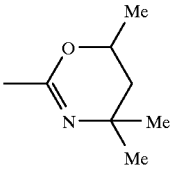 | Me | |
| 22.193 | O | Me | 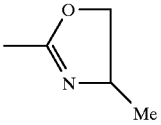 | Me | |
| 22.194 | O | Me | 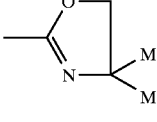 | Me | |
| 22.195 | O | Me | 2-pyridyl | Me | |
| 22.196 | O | Me | 3-pyridyl | Me | |
| 22.197 | O | Me | 4-pyridyl | Me | |
| 22.198 | O | Me | 2-pyrimidinyl | Me | |
| 22.199 | O | Me | 4-chloro-5-cyano-6-methylthio-2-pyrimidinyl | Me | |
| 22.200 | O | Me | 4,6-dichloro-2-pyrimidinyl | Me | |
| 22.201 | O | Me | 3-methoxy-2-pyrazinyl | Me | |
| 22.202 | O | Me | 2-pyrazinyl | Me | |
| 22.203 | O | Me | 5-ethoxycarbonyl-4-trifluoromethyl-2-thiazolyl | Me | |
| 22.204 | O | Me | 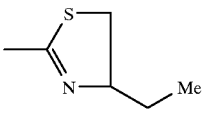 | Me | |

TABLE 23

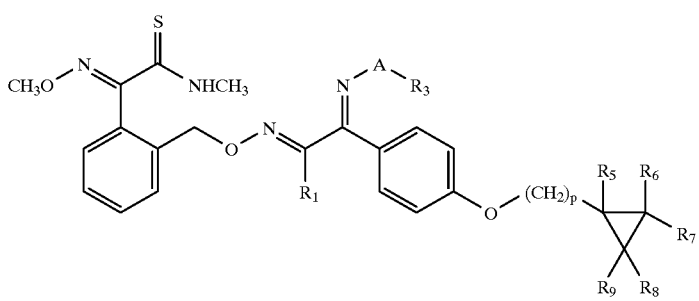

| Ex. No. | A | R₁ | R₃ | R₅ | R₆ | R₇ | R₈ | R₉ | p | phys. data |
|---|---|---|---|---|---|---|---|---|---|---|
| 23.1 | NMe | Me | Me | H | Cl | Cl | H | H | 1 | |
| 23.2 | NMe | H | Me | H | Cl | Cl | H | H | 1 | |
| 23.3 | NMe | Me | Me | H | F | F | H | H | 1 | |
| 23.4 | NMe | Me | Me | H | Br | Br | H | H | 1 | |
| 23.5 | NMe | Me | Et | H | F | F | H | H | 1 | |
| 23.6 | NPh | Me | Me | H | Cl | Cl | H | H | 1 | |
| 23.7 | NPh | H | Me | H | Cl | Cl | H | H | 1 | |
| 23.8 | NPh | Me | Et | H | Cl | Cl | H | H | 1 | |
| 23.9 | O | H | Me | H | Cl | Cl | H | H | 1 | |
| 23.10 | O | Me | Me | H | F | F | H | H | 1 | |
| 23.11 | O | H | Me | H | F | F | H | H | 1 | |
| 23.12 | O | Me | H | H | F | F | H | H | 1 | |
| 23.13 | O | Me | C₃H₇ | H | Cl | Cl | H | H | 1 | |
| 23.14 | O | Me | Δ | H | Cl | Cl | H | H | 1 | |
| 23.15 | O | Δ | Me | H | Cl | Cl | H | H | 1 | |
| 23.16 | O | Me | Et | H | Cl | Cl | H | H | 1 | |
| 23.17 | O | H | Me | H | Br | Br | H | H | 1 | |
| 23.18 | O | Me | Me | H | Cl | Cl | H | H | 2 | |
| 23.19 | O | H | Me | H | Cl | Cl | H | H | 2 | |
| 23.20 | O | Me | Me | H | F | F | H | H | 2 | |
| 23.21 | O | Me | Me | Me | Cl | Cl | H | H | 1 | |
| 23.22 | O | Me | Me | H | Cl | Cl | Me | Me | 1 | |

TABLE 24

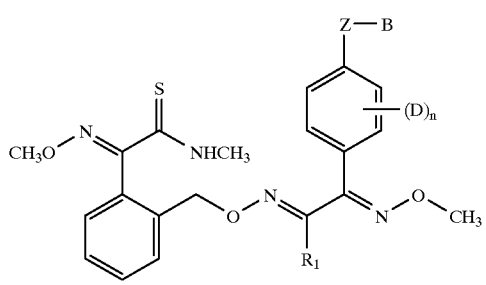

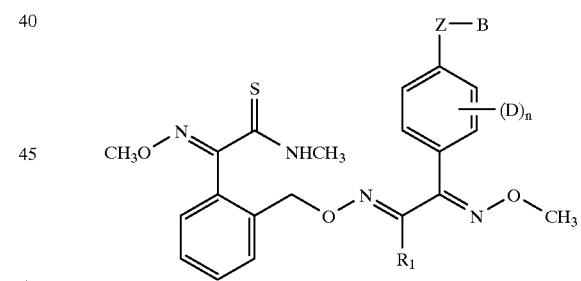

| Ex. No. | R₁ | Z* | n | B or D | phys. data |
|---|---|---|---|---|---|
| 24.1 | Me | — | 1 | 3-CF₃ | |
| 24.2 | Me | — | 1 | 4-chloro | |
| 24.3 | Me | — | 1 | 3-chloro | |
| 24.4 | Me | — | 1 | 2-fluoro | |
| 24.5 | Me | O | 0 | Me | |
| 24.6 | Me | — | 1 | 4-bromo | |
| 24.7 | Me | — | 1 | 4-fluoro | |
| 24.8 | Me | — | 2 | 3-F-5-CF₃ | |
| 24.9 | Me | — | 0 | — | |
| 24.10 | Me | — | 1 | 3-bromo | |
| 24.11 | Me | — | 2 | 3,4-methylenedioxy | |
| 24.12 | SMe | — | 1 | 4-methyl | |
| 24.13 | Et | — | 1 | 4-methyl | |
| 24.14 | Me | — | 1 | 4-isobutyl | |
| 24.15 | Me | O | 0 | 2,2,2-trifluoroethyl | |
| 24.16 | CN | — | 1 | 4-methyl | |
| 24.17 | CN | — | 1 | 4-chloro | |
| 24.18 | CN | — | 2 | 3,4-dichloro | |
| 24.19 | CN | O | 0 | CF₃ | |
| 24.20 | CN | — | 1 | 3-CF₃ | |
| 24.21 | CN | — | 1 | 4-fluoro | |
| 24.22 | Me | O | 0 | phenyl | |
| 24.23 | Me | O | 0 | CH₂CH=CCl₂ | |
| 24.24 | Me | O | 0 | CH₂CH=CF₂ | |
| 24.25 | Me | O | 0 | CH₂CH=CBr₂ | |
| 24.26 | Me | O | 0 | 4-Cl-phenyl | |
| 24.27 | Me | O | 0 | 4-F-phenyl | |
| 24.28 | Me | S | 0 | phenyl | |
| 24.29 | Me | CH₂O | 0 | phenyl | |
| 24.30 | Me | O | 0 | 3,3-dimethylallyl | |
| 24.31 | Me | O | 0 | 2-methylallyl | |
| 24.32 | Me | O | 0 | 3-methyl | |
| 24.33 | Me | OCH₂ | 0 | 3-CF₃-phenyl | oil |
| 24.34 | Me | CH₂O | 0 | 3-CF₃-phenyl | |

TABLE 24-continued

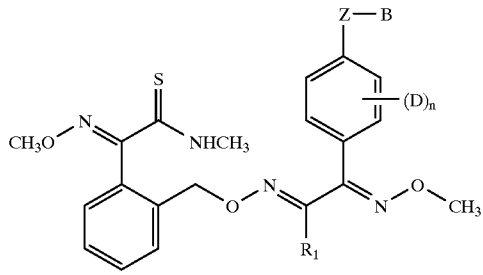

| Ex. No. | $R_1$ | $Z^*$ | n | B or D | phys. data |
|---|---|---|---|---|---|
| 24.35 | Me | $OCH_2$ | 0 | $C_6H_{11}$ | |
| 24.36 | Me | $OCH_2$ | 0 | 3-$CH_3$-phenyl | |
| 24.37 | Me | $OCH_2$ | 0 | 3-$OCH_3$-phenyl | |
| 24.38 | Me | $OCH_2$ | 0 | 4-$CF_3$-phenyl | |
| 24.39 | Me | $OCH_2$ | 0 | 4-Br-phenyl | |
| 24.40 | Me | $OCH_2$ | 0 | 4-$CH_3$-phenyl | |
| 24.41 | Me | $OCH_2$ | 0 | 4-$OCH_3$-phenyl | |
| 24.42 | Me | $OCH_2$ | 0 | 2-$CF_3$-phenyl | |
| 24.43 | Me | $OCH_2$ | 0 | 2-F-phenyl | |
| 24.44 | Me | $OCH_2$ | 0 | 2-Cl-phenyl | |
| 24.45 | Me | $OCH_2$ | 0 | 2-Br-phenyl | |
| 24.46 | Me | $OCH_2$ | 0 | 3-F-phenyl | |
| 24.47 | Me | $OCH_2$ | 0 | 3-Cl-phenyl | |
| 24.48 | Me | $OCH_2$ | 0 | 3-Br-phenyl | |
| 24.49 | CN | — | — | H | |
| 24.50 | CN | — | 1 | 4-tert-butyl | |
| 24.51 | CN | O | 0 | phenyl | |
| 24.52 | Me | O | 0 | $CF_2CHF_2$ | |
| 24.53 | Me | O | 0 | $CF_2CHCl_2$ | |
| 24.54 | Me | O | 0 | $CF_2CHBr_2$ | |
| 24.55 | Me | — | 1 | 4-tert-butyl | oil |
| 24.56 | Me | — | 1 | 4-$CF_3$ | foam |
| 24.57 | Me | $OCH_2$ | 0 | 4-Cl-phenyl | |

TABLE 24-continued

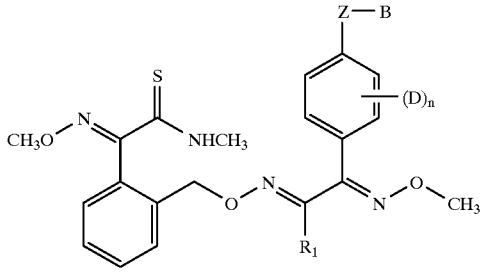

| Ex. No. | $R_1$ | $Z^*$ | n | B or D | phys. data |
|---|---|---|---|---|---|
| 24.58 | Me | — | 1 | 2-methyl | m.p. 123–4° C. |
| 24.59 | Me | — | 1 | 4-phenyl | oil |

TABLE 25

204 compounds of the formula

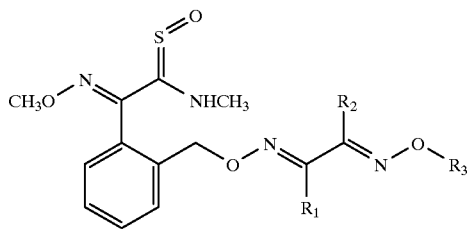

wherein A, $R_1$, $R_2$ and $R_3/NR_3R_4$ are as defined for the corresponding compounds of of Table 1.

TABLE 26

22 compounds of the formula

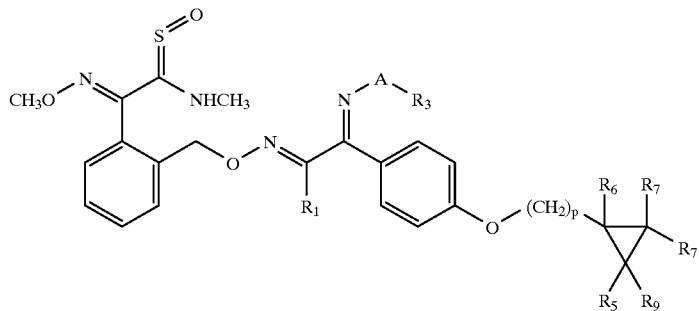

wherein A, $R_1$, $R_3$, $R_5$, $R_6$, $R_7$, $R_8$, $R_9$ and p are as defined for the corresponding compounds of Table 2.

TABLE 27

57 compounds of the formula

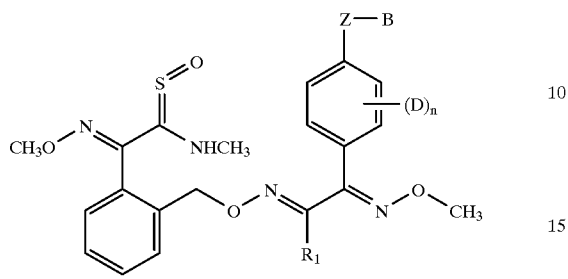

wherein $R_1$, Z, n, B, and D are as defined for the corresponding compounds of Table 3.

TABLE 28

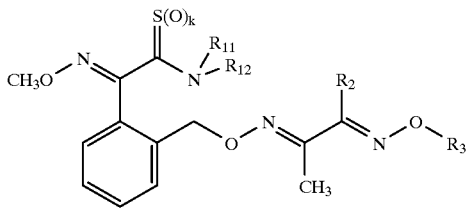

| Ex. No. | $R_{11}$ | $R_{12}$ | k | $R_2$ | $R_3$ | phys. data |
|---|---|---|---|---|---|---|
| 28.1 | H | H | 0 | Me | Me | 303 (2, M-HS), 60 |
| 28.2 | Me | H | 0 | Me | Me | 317 (2, M-HS), 74 |
| 28.3 | Me | H | 1 | Me | Me | |
| 28.4 | Et | H | 0 | Me | Me | 331 (1, M-HS), 88 |
| 28.5 | Me | Me | 0 | Me | Me | |
| 28.6 | Me | Me | 1 | Me | Me | |
| 28.7 | Et | Me | 0 | Me | Me | |
| 28.8 | $COCH_3$ | Me | 0 | Me | Me | |
| 28.9 | allyl | Me | 0 | Me | Me | |
| 28.10 | Me | H | 0 | Me | $CH_2OCH_3$ | |
| 28.11 | Me | H | 1 | Me | $CH_2OCH_3$ | |
| 28.12 | Me | H | 0 | Me | $CH_2CN$ | |
| 28.13 | Me | H | 1 | Me | $CH_2CN$ | |
| 28.14 | Me | H | 0 | Me | allyl | |
| 28.15 | Me | H | 1 | Me | allyl | |
| 28.16 | Me | H | 0 | Me | methallyl | |
| 28.17 | Me | H | 1 | Me | methallyl | |
| 28.18 | Me | H | 0 | Me | propargyl | |
| 28.19 | Me | H | 1 | Me | propargyl | |
| 28.20 | Me | H | 0 | Me | $CH_2$-cyclopropyl(Cl,Cl) | |
| 28.21 | Me | H | 1 | Me | $CH_2$-cyclopropyl(Cl,Cl) | |
| 28.22 | H | H | 0 | Me | $CH_2CF_3$ | |
| 28.23 | Me | H | 0 | Me | $CH_2CF_3$ | 98–99° C. |
| 28.24 | Me | H | 1 | Me | $CH_2CF_3$ | |
| 28.25 | Me | Me | 1 | Me | $CH_2CF_3$ | |
| 28.26 | Et | Me | 0 | Me | $CH_2CF_3$ | |
| 28.27 | Me | H | 0 | Me | $CH_2CH_2CF_3$ | |
| 28.28 | Me | H | 1 | Me | $CH_2CH_2CF_3$ | |
| 28.29 | Me | H | 0 | Me | $CH_2CH_2CH_2CF_3$ | |

TABLE 28-continued

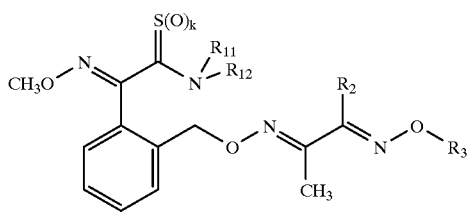

| Ex. No. | R11 | R12 | k | R2 | R3 | phys. data |
|---|---|---|---|---|---|---|
| 28.30 | Me | H | 1 | Me | CH₂CH₂CH₂CF₃ | |
| 28.31 | Me | H | 0 | Me | CH₂C(Cl)=CH₂ | 79–80° C. |
| 28.32 | Me | H | 1 | Me | CH₂C(Cl)=CH₂ | |
| 28.33 | Me | Me | 0 | Me | CH₂C(Cl)=CH₂ | |
| 28.34 | Me | Me | 1 | Me | CH₂C(Cl)=CH₂ | |
| 28.35 | Me | H | 0 | Me | CH₂—▷ | |
| 28.36 | Me | H | 1 | Me | CH₂—▷ | |
| 28.37 | Me | H | 0 | Me | CH₂CH₂F | |
| 28.38 | Me | H | 1 | Me | CH₂CH₂F | |
| 28.39 | H | H | 0 | CN | Me | |
| 28.40 | Me | H | 0 | CN | Me | |
| 28.41 | Me | H | 1 | CN | Me | |
| 28.42 | Et | Me | 0 | CN | Me | |
| 28.43 | Et | Me | 1 | CN | Me | |
| 28.44 | Me | H | 0 | CN | CH₂CF₃ | |
| 28.45 | Me | H | 1 | CN | CH₂CF₃ | |
| 28.46 | Et | H | 0 | CN | CH₂CF₃ | |
| 28.47 | Me | H | 0 | COOMe | Me | |
| 28.48 | Me | H | 1 | COOMe | Me | |
| 28.49 | allyl | Me | 0 | COOMe | Me | |
| 28.50 | allyl | Me | 1 | COOMe | Me | |
| 28.51 | Me | H | 0 | COOMe | CH₂CF₃ | |
| 28.52 | Me | H | 1 | COOMe | CH₂CF₃ | |
| 28.53 | Me | H | 0 | COOBu | Me | |
| 28.54 | Me | H | 1 | COOBu | Me | |
| 28.55 | Me | Me | 0 | COOBu | Me | |
| 28.56 | Me | Me | 1 | COOBu | Me | |
| 28.57 | H | H | 0 | 2-Δ²-thiazolinyl | Me | |
| 28.58 | Me | H | 0 | 2-Δ²-thiazolinyl | Me | |
| 28.59 | Me | H | 1 | 2-Δ²-thiazolinyl | Me | |
| 28.60 | Et | H | 0 | 2-Δ²-thiazolinyl | Me | |
| 28.61 | Et | H | 1 | 2-Δ²-thiazolinyl | Me | |
| 28.62 | Me | Me | 0 | 2-Δ²-thiazolinyl | Me | |
| 28.63 | Me | Me | 1 | 2-Δ²-thiazolinyl | Me | |
| 28.64 | Et | Me | 0 | 2-Δ²-thiazolinyl | Me | |
| 28.65 | Et | Me | 1 | 2-Δ²-thiazolinyl | Me | |
| 28.66 | Me | H | 0 | 2-Δ²-oxazolinyl | Me | |
| 28.67 | Et | H | 0 | 2-Δ²-oxazolinyl | Me | |
| 28.68 | Me | Me | 0 | 2-Δ²-oxazolinyl | Me | |
| 28.69 | Me | Me | 1 | 2-Δ²-oxazolinyl | Me | |
| 28.70 | Et | Me | 0 | 2-Δ²-oxazolinyl | Me | |
| 28.71 | Et | Me | 1 | 2-Δ²-oxazolinyl | Me | |
| 28.72 | Me | H | 0 | 2-thiazolyl | Me | |
| 28.73 | Me | H | 1 | 2-thiazolyl | Me | |

TABLE 29

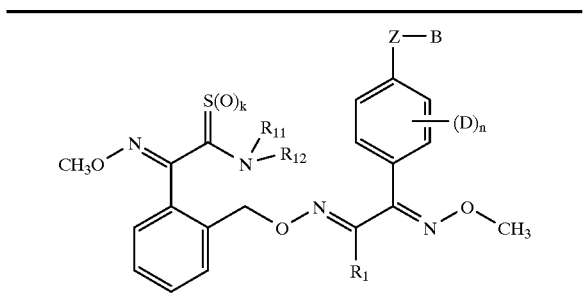

| Ex. No. | $R_{11}$ | $R_{12}$ | k | $R_1$ | Z* | n | B or D | phys. data |
|---|---|---|---|---|---|---|---|---|
| 29.1 | H | H | 0 | Me | — | 1 | 4-methyl | |
| 29.2 | Me | H | 0 | Me | — | 1 | 4-methyl | |
| 29.3 | Me | H | 1 | Me | — | 1 | 4-methyl | |
| 29.4 | Et | H | 0 | Me | — | 1 | 4-methyl | |
| 29.5 | Me | Me | 0 | Me | — | 1 | 4-methyl | |
| 29.6 | Me | Me | 1 | Me | — | 1 | 4-methyl | |
| 29.7 | Et | Me | 0 | Me | — | 1 | 4-methyl | |
| 29.8 | COCH$_3$ | Me | 0 | Me | — | 1 | 4-methyl | |
| 29.9 | allyl | Me | 0 | Me | — | 1 | 4-methyl | |
| 29.10 | Me | H | 0 | Me | — | 1 | 2-methyl | |
| 29.11 | Me | H | 1 | Me | — | 1 | 2-methyl | |
| 29.12 | Me | Me | 0 | Me | — | 1 | 2-methyl | |
| 29.13 | Me | Me | 1 | Me | — | 1 | 2-methyl | |
| 29.14 | Me | H | 0 | Me | O | 0 | allyl | 350(2), 116 |
| 29.15 | Me | H | 1 | Me | O | 0 | allyl | |
| 29.16 | Me | H | 0 | Me | O | 0 | propargyl | |
| 29.17 | Me | H | 1 | Me | O | 0 | propargyl | |
| 29.18 | Me | H | 0 | Me | O | 0 | ethyl | |
| 29.19 | Me | H | 1 | Me | O | 0 | ethyl | |
| 29.20 | Me | H | 0 | CN | — | 1 | 2-chloro | |
| 29.21 | Me | H | 1 | CN | — | 1 | 2-chloro | |
| 29.22 | Et | Me | 0 | CN | — | 1 | 2-chloro | |
| 29.23 | Et | Me | 1 | CN | — | 1 | 2-chloro | |
| 29.24 | Me | H | 0 | Me | OCH$_2$ | 0 | phenyl | |
| 29.25 | Me | H | 1 | Me | OCH$_2$ | 0 | phenyl | |
| 29.26 | Me | H | 0 | Me | O | 0 | n-Pr | |
| 29.27 | Me | H | 1 | Me | O | 0 | n-Pr | |
| 29.28 | Me | Me | 0 | Me | O | 0 | n-Pr | |
| 29.29 | Me | Me | 1 | Me | O | 0 | n-Pr | |
| 29.30 | Me | H | 0 | Me | OCH$_2$ | 0 | 4-F-phenyl | |
| 29.31 | Me | H | 1 | Me | OCH$_2$ | 0 | 4-F-phenyl | |
| 29.32 | Me | H | 0 | Me | S | 0 | Me | |
| 29.33 | Me | H | 1 | Me | S | 0 | Me | |
| 29.34 | Me | Me | 0 | Me | S | 0 | Me | |
| 29.35 | Me | Me | 1 | Me | S | 0 | Me | |
| 29.36 | Me | H | 0 | Me | SO | 0 | Me | |
| 29.37 | Me | H | 1 | Me | SO | 0 | Me | |
| 29.38 | Me | H | 0 | Me | SO$_2$ | 0 | Me | |
| 29.39 | Me | H | 1 | Me | SO$_2$ | 0 | Me | |
| 29.40 | H | H | 0 | Me | S | 0 | Et | |
| 29.41 | Me | H | 0 | Me | S | 0 | Et | |
| 29.42 | Me | H | 1 | Me | S | 0 | Et | |
| 29.43 | Me | Me | 0 | Me | S | 0 | Et | |
| 29.44 | Et | Me | 0 | Me | S | 0 | Et | |
| 29.45 | Me | H | 0 | Me | SO | 0 | Et | |
| 29.46 | Me | H | 1 | Me | SO | 0 | Et | |
| 29.47 | Me | H | 0 | Me | SO$_2$ | 0 | Et | |
| 29.48 | Me | H | 1 | Me | SO$_2$ | 0 | Et | |
| 29.49 | Me | H | 0 | Me | S | 0 | n-C$_3$H$_7$ | |
| 29.50 | Me | H | 1 | Me | S | 0 | n-C$_3$H$_7$ | |
| 29.51 | Me | H | 0 | Me | SO | 0 | n-C$_3$H$_7$ | |
| 29.52 | Me | H | 1 | Me | SO | 0 | n-C$_3$H$_7$ | |
| 29.53 | Me | H | 0 | Me | SO$_2$ | 0 | n-C$_3$H$_7$ | |
| 29.54 | Me | H | 1 | Me | SO$_2$ | 0 | n-C$_3$H$_7$ | |
| 29.55 | Me | H | 0 | CN | O | 0 | Me | |
| 29.56 | Me | H | 1 | CN | O | 0 | Me | |
| 29.57 | Et | H | 0 | CN | O | 0 | Me | |
| 29.58 | Et | H | 1 | CN | O | 0 | Me | |
| 29.59 | Me | Me | 0 | CN | O | 0 | Me | |
| 29.60 | Me | Me | 1 | CN | O | 0 | Me | |
| 29.61 | H | H | 0 | Me | — | 1 | 4-ethyl | |
| 29.62 | Me | H | 0 | Me | — | 1 | 4-ethyl | |
| 29.63 | Me | H | 1 | Me | — | 1 | 4-ethyl | |
| 29.64 | Me | Me | 0 | Me | — | 1 | 4-ethyl | |
| 29.65 | Me | Me | 1 | Me | — | 1 | 4-ethyl | |
| 29.66 | Et | Me | 0 | Me | — | 1 | 4-ethyl | |
| 29.67 | Et | Me | 1 | Me | — | 1 | 4-ethyl | |
| 29.68 | allyl | Me | 0 | Me | — | 1 | 4-ethyl | |
| 29.69 | allyl | Me | 1 | Me | — | 1 | 4-ethyl | |
| 29.70 | Me | H | 0 | Me | — | 1 | 4-n-Pr | |
| 29.71 | Me | H | 1 | Me | — | 1 | 4-n-Pr | |
| 29.72 | Me | Me | 0 | Me | — | 1 | 4-n-Pr | |
| 29.73 | Me | Me | 1 | Me | — | 1 | 4-n-Pr | |

TABLE 30

| Ex. No. | $R_{11}$ | $R_{12}$ | k | $R_6$ | $R_7$ | phys. data |
|---|---|---|---|---|---|---|
| 30.1 | H | H | 0 | Cl | Cl | |
| 30.2 | Me | H | 0 | Cl | Cl | |
| 30.3 | Me | H | 1 | Cl | Cl | |
| 30.4 | Et | H | 0 | Cl | Cl | |
| 30.5 | Et | H | 1 | Cl | Cl | |
| 30.6 | Me | Me | 0 | Cl | Cl | |
| 30.7 | Me | Me | 1 | Cl | Cl | |
| 30.8 | Et | Me | 0 | Cl | Cl | |
| 30.9 | Et | Me | 1 | Cl | Cl | |
| 30.10 | COCH$_3$ | Me | 0 | Cl | Cl | |
| 30.11 | COCH$_3$ | Me | 1 | Cl | Cl | |
| 30.12 | allyl | Me | 0 | Cl | Cl | |
| 30.13 | allyl | Me | 1 | Cl | Cl | |
| 30.14 | Me | H | 0 | Br | Br | |
| 30.15 | Me | H | 1 | Br | Br | |
| 30.16 | H | H | 0 | F | F | |
| 30.17 | Me | H | 0 | F | F | |
| 30.18 | Me | H | 1 | F | F | |
| 30.19 | Me | Me | 0 | F | F | |
| 30.20 | Me | Me | 1 | F | F | |
| 30.21 | Et | Me | 0 | F | F | |
| 30.22 | Et | Me | 1 | F | F | |
| 30.23 | Me | H | 0 | H | H | |
| 30.24 | Me | H | 1 | H | H | |
| 30.25 | Et | H | 0 | H | H | |
| 30.26 | Et | H | 1 | H | H | |
| 30.27 | Me | Me | 0 | H | H | |

TABLE 30-continued (structure with S(O)k, R11, R12, OCH3, R6, R7 groups)

| Ex. No. | $R_{11}$ | $R_{12}$ | k | $R_6$ | $R_7$ | phys. data |
|---|---|---|---|---|---|---|
| 30.28 | Me | Me | 1 | H | H | |
| 30.29 | Et | Me | 0 | H | H | |
| 30.30 | Et | Me | 1 | H | H | |

TABLE 31

(Intermediates)

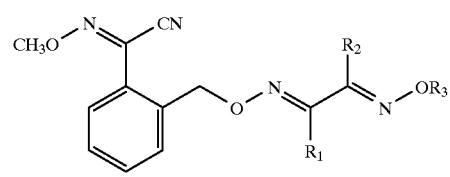

| Ex. No. | $R_1$ | $R_2$ | $R_3$ | phys. data |
|---|---|---|---|---|
| 31.1 | Me | Me | Me | m.p. 75–77° C. |
| 31.2 | Me | Δ | Me | |
| 31.3 | Me | Me | 2,2-dichloro-cyclopropylmethyl | |
| 31.4 | Me | Me | H | |
| 31.5 | Me | Me | $CF_3CH_2$ | |
| 31.6 | Me | Me | $CF_3CH_2CH_2$ | |
| 31.7 | Me | Me | $CF_3CH_2CH_2CH_2$ | |
| 31.8 | Me | Me | 4-methoxybenzyl | |
| 31.9 | Me | Me | $CH_2F$ | |
| 31.10 | Me | Me | cyclopropylmethyl | |
| 31.11 | Me | Me | $CH_2CH_2F$ | |
| 31.12 | Me | CN | Me | |
| 31.13 | Me | COOMe | Me | |
| 31.14 | Me | $COOC(Me)_3$ | Me | |
| 31.15 | Me | $COOCH(Me)_2$ | Me | |
| 31.16 | Me | $COOCH_2CH=CH_2$ | Me | |
| 31.17 | Me | 2-$\Delta^2$-thiazolinyl | Me | |
| 31.18 | Me | 2-thiazolyl | Me | |
| 31.19 | Me | 2-pyridyl | Me | |
| 31.20 | Me | 3-pyridyl | Me | |
| 31.21 | Me | 2-pyrazinyl | Me | |
| 31.22 | Me | 5-Me-3-isoxazolyl | Me | |
| 31.23 | Me | 1-naphthyl | Me | |
| 31.24 | Me | 2-naphthyl | Me | |
| 31.25 | Me | 4-biphenyl | Me | |

TABLE 32

(Intermediates)

| Ex. No. | $R_1$ | $Z^*$ | n | B or D | phys. data |
|---|---|---|---|---|---|
| 32.1 | Me | — | 1 | 2-Me | |
| 32.2 | Me | — | 1 | 3-Me | |
| 32.3 | Me | — | 1 | 4-Me | |
| 32.4 | Me | — | 1 | 2-$CF_3$ | |
| 32.5 | Me | — | 1 | 3-$CF_3$ | |
| 32.6 | Me | — | 1 | 4-$CF_3$ | |
| 32.7 | Me | — | 1 | 4-Et | |
| 32.8 | Me | — | 1 | 4-tert-butyl | |
| 32.9 | Me | — | 2 | 2,3-dimethyl | |
| 32.10 | Me | — | 2 | 2,4-dimethyl | |
| 32.11 | Me | — | 2 | 2,5-dimethyl | |
| 32.12 | Me | — | 2 | 2-Me,4-F | |
| 32.13 | Me | — | 2 | 2-Me,5-F | |
| 32.14 | Me | — | 2 | 2-F,5-Me | |
| 32.15 | Me | — | 2 | 3-$CF_3$,4-Cl | |
| 32.16 | Me | O | 0 | Me | |
| 32.17 | Me | O | 0 | Et | |
| 32.18 | Me | O | 0 | n-propyl | |
| 32.19 | Me | O | 0 | i-propyl | |
| 32.20 | Me | O | 0 | 3-$CF_3$-phenyl | |
| 32.21 | Me | O | 0 | 4-fluorophenyl | |
| 32.22 | Me | O | 0 | 4-chlorophenyl | |
| 32.23 | Me | O | 0 | 4-bromophenyl | |
| 32.24 | Me | O | 0 | $CF_3$ | |
| 32.25 | Me | O | 0 | $CHF_2$ | |
| 32.26 | Me | O | 0 | $CF_2CHF_2$ | |
| 32.27 | Me | —$OCH_2$— | 0 | 3-$CF_3$-phenyl | |
| 32.28 | Me | —$OCH_2$— | 0 | 2-$CF_3$-phenyl | |
| 32.29 | Me | —$OCH_2$— | 0 | 4-$CF_3$-phenyl | |
| 32.30 | Me | —$OCH_2$— | 0 | trimethylsilyl | |
| 32.31 | Me | —$OCH_2$— | 0 | $CF_3$ | |
| 32.32 | Me | — | 1 | 4-ethynyl | |
| 32.33 | Me | — | 1 | 4-(3-methyl-isoxazol-5-yl) | |
| 32.34 | Me | — | 1 | 4-phenyl | |
| 32.35 | Me | O | 0 | n-butyl | |
| 32.36 | Me | O | 0 | isobutyl | |
| 32.37 | Me | O | 0 | sec-butyl | |
| 32.38 | Me | O | 0 | tert-butyl | |
| 32.39 | Me | — | 1 | 2-methoxy | |
| 32.40 | Me | — | 1 | 4-trimethylsilyl | |

TABLE 33

(Intermediates)

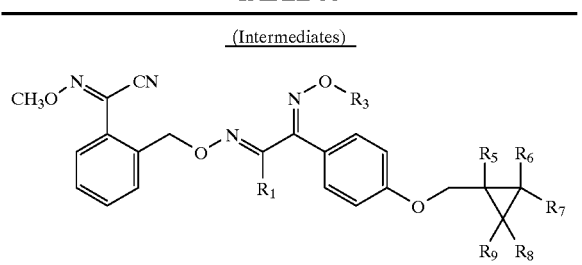

| Ex. No. | $R_1$ | $R_3$ | $R_5$ | $R_6$ | $R_7$ | $R_8$ | $R_9$ | phys. data |
|---|---|---|---|---|---|---|---|---|
| 33.1 | Me | Me | H | H | H | H | H | |
| 33.2 | Me | Me | H | Cl | Cl | H | H | |
| 33.3 | Me | Me | H | Br | Br | H | H | |
| 33.4 | H | Me | H | Br | Br | H | H | |
| 33.5 | Me | Et | H | Br | Br | H | H | |
| 33.6 | Me | Me | Me | F | F | H | H | |
| 33.7 | Me | Me | Me | Cl | Cl | H | H | |
| 33.8 | Me | Me | Me | Br | Br | H | H | |
| 33.9 | Me | Me | H | Cl | Cl | Me | Me | |
| 33.10 | Me | Me | H | Br | Br | Me | Me | |
| 33.11 | Me | Me | H | F | F | H | H | |
| 33.12 | Me | Me | Me | Br | F | H | H | |

FORMULATION EXAMPLES FOR COMPOUNDS OF FORMULA I

Examples F-1.1 to F-1.3: Emulsifiable Concentrates

| constituents | F-1.1 | F-1.2 | F-1.3 |
|---|---|---|---|
| a compound of Tables 1–10 | 25% | 40% | 50% |
| calcium dodecylbenzenesulfonate | 5% | 8% | 6% |
| castor oil polyethylene glycol ether (36 mol of ethyleneoxy units) | 5% | — | — |
| tributylphenol polyethylene glycol ether (30 mol of ethyleneoxy units) | — | 12% | 4% |
| cyclohexanone | — | 15% | 20% |
| xylene mixture | 65% | 25% | 20% |

Emulsions of any desired dilution can be prepared from these emulsifiable concentrates with water.

Example F-2: Emulsifiable Concentrate

| constituents | F-2 |
|---|---|
| a compound of the Tables | 10% |
| octylphenol polyethylene glycol ether (4–5 mol of ethyleneoxy units) | 3% |
| calcium dodecylbenzenesulfonate | 3% |
| castor oil polyglycol ether (36 mol of ethyleneoxy units) | 4% |
| cyclohexanone | 30% |
| xylene mixture | 50% |

Emulsions of any desired dilution can be prepared from this emulsifiable concentrate with water.

Examples F-3.1 to F-3.4: Solutions

| constituents | F-3.1 | F-3.2 | F-3.3 | F-3.4 |
|---|---|---|---|---|
| a compound of the Tables | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| petroleum fraction (boiling range: 160–190°) | — | — | 94% | — |

The solutions are suitable for application in the form of microdrops.

Examples F-4.1 to F-4.4: Granules

| constituents | F-4.1 | F-4.2 | F-4.3 | F-4.4 |
|---|---|---|---|---|
| a compound of the Tables | 5% | 10% | 8% | 21% |
| kaolin | 94% | — | 79% | 54% |
| highly dispersed silicic acid | 1% | — | 13% | 7% |
| attapulgite | — | 90% | — | 18% |

The compound of the invention is dissolved in dichloromethane, the solution is sprayed onto the carrier and the solvent is subsequently evaporated off in vacuo.

Examples F-5.1 and F-5.2: Dusts

| constituents | F-5.1 | F-5.2 |
|---|---|---|
| a compound of the Tables | 2% | 5% |
| highly dispersed silicic acid | 1% | 5% |
| talcum | 97% | — |
| kaolin | — | 90% |

Ready-for-use dusts are obtained by intimately mixing all the constituents.

Examples F-6.1 to F-6.3: Wettable Powders

| constituents | F-6.1 | F-6.2 | F-6.3 |
|---|---|---|---|
| a compound of the Tables | 25% | 50% | 75% |
| sodium lignosulfonate | 5% | 5% | — |
| sodium lauryl sulfate | 3% | — | 5% |
| sodium diisobutyl-naphthalenesulfonate | — | 6% | 10% |
| octylphenol polyethylene glycol ether (7–8 mol of ethyleneoxy units) | — | 2% | — |
| highly dispersed silicic acid | 5% | 10% | 10% |
| kaolin | 62% | 27% | — |

Example F-7: Wettable Powders

| constituents | |
|---|---|
| a compound of the Tables | 25% |
| sodium lignosulfonate | 5% |
| kieselguhr | 25% |
| sodium carbonate | 5% |
| disodium-1-benzyl-2-heptadecylbenzimidazole-X,X'-disulfonic acid (incl. 15–30% $Na_2SO_4$) | 5% |
| Champagne chalk | 35% |

All the constituents are mixed together and the mixture is thoroughly ground in a suitable mill, affording wettable powders which can be diluted with water to give suspensions of any desired concentration.

BIOLOGICAL EXAMPLES: A. MICROBICIDAL ACTION

B-1: Action Against *Puccinia graminis* on Wheat
a) Residual-protective Action:
6 days after sowing, wheat plants are sprayed to drip point with an aqueous spray mixture (0.02% active ingredient) prepared from a wettable powder formulation of the test compound and are infected 24 hours later with a uredospore suspension of the fungus. After an incubation period of 48 hours (conditions: 95 to 100% relative humidity at 20°), the plants are placed in a greenhouse at 22°. Evaluation of fungus infestation is made 12 days after infection.
b) Systemic Action:
5 days after sowing, wheat plants are watered with an aqueous spray mixture (0.006% active ingredient, based on the volume of the soil) prepared from a wettable powder formulation of the test compound. Care is taken that the spray mixture does not come into contact with the parts of the plants above the soil. After 48 hours the plants are infected with a uredospore suspension of the fungus. After an incubation period of 48 hours (conditions: 95 to 100% relative humidity at 20°), the plants are placed in a greenhouse at 22°. Evaluation of fungus infestation is made 12 days after infection.

Compounds of the Tables exhibit good activity.

Example B-2: Action Against *Phytophthora infestans* on Tomato Plants a) Residual Protective Action:
After a cultivation period of 3 weeks, tomato plants are sprayed to drip point with an aqueous spray mixture (0.02% active ingredient) prepared from a wettable powder formulation of the test compound. After 24 hours the treated plants are infected with a sporangia suspension of the fungus. The infected plants are then incubated for 5 days at 90–100% relative humidity and 20° C. and then evaluated for fungus infestation.
b) Systemic Action:
After a cultivation period of 3 weeks, an aqueous spray mixture (0.006% active ingredient, based on the volume of the soil) prepared from a wettable powder formulation of the test compound is used to water tomato plants. Care is taken that the spray mixture does not come into contact with the parts of the plants above the soil. The treated plants are infected 48 hours later with a sporangia suspension of the fungus. The infected plants are then incubated for 5 days at 90–100% relative humidity and 20° C. and then evaluated for fungus infestation.

Compounds of the Tables exhibit good activity.

Example B-3: Residual-protective Action Against *Cercospora arachidicola* on Groundnuts 10 to 15 cm high groundnut plants are sprayed to drip point with an aqueous spray mixture (0.02% active ingredient) prepared from a wettable powder formulation of the test compound and are infected 48 hours later with a conidia suspension of the fungus. The plants are incubated for 72 hours at 21° and high humidity and are then placed in a greenhouse until the typical leaf specks appear. The activity of the test compound is evaluated 12 days after infection and is based on the number and size of the leaf specks.

Compounds of the Tables exhibit good activity.

Example B-4: Action Against *Plasmopara viticola* on Vines

Vine seedlings in the 4–5 leaf stage are sprayed to drip point with an aqueous spray mixture (0.02% active ingredient) prepared from a wettable powder formulation of the test compound. After 24 hours the treated plants are infected with a sporangia suspension of the fungus. The infected plants are incubated for 6 days at 95–100% relative humidity and 20° C. and then evaluated for fungus infestation.

Compounds of the Tables exhibit good activity.

Example B-5: Action Against *Colletotrichum lagenarium* on Cucumbers

After a cultivation period of 2 weeks, cucumber plants are sprayed with a spray mixture (concentration 0.002%) prepared from a wettable powder formulation of the test compound. 2 days later, the plants are infected with a spore suspension ($1.5 \times 10^5$ spores/ml) of the fungus and are incubated for 36 hours at 23° C. and high humidity. Incubation is then continued at normal humidity and about 22° C. The fungus infestation that has occurred is evaluated 8 days after infection.

Compounds of the Tables exhibit good activity.

Example B-6: Residual-protective Action Against *Venturia inaequalis* on Apples Apple cuttings with 10–20 cm long fresh shoots are sprayed to drip point with an aqueous spray mixture (0.02% active ingredient) prepared from a wettable powder formulation of the test compound and are infected 24 hours later with a conidia suspension of the fungus. The plants are incubated for 5 days at 90 to 100% relative humidity and are placed for a further 10 days in a greenhouse at 20 to 24°. Fungus infestation is evaluated 12 days after infection.

Compounds of the Tables exhibit good activity.

Example B-7: Action Against *Erysiphe graminis* on Barley a) Residual-protective Action:
Barley plants about 8 cm in height are sprayed to drip point with an aqueous spray mixture (0.02% active ingredient) prepared from a wettable powder formulation of the test compound and are dusted 3 to 4 hours later with conidia of the fungus. The infected plants are placed in a greenhouse at 22°. Fungus infestation is evaluated 12 days after infection.

Compounds of the Tables exhibit good activity.
b) Systemic Action:
Barley plants about 8 cm in height are watered with an aqueous spray mixture (0.002% active ingredient, based on the volume of the soil) prepared from a wettable powder formulation of the test compound. Care is taken that the spray mixture does not come into contact with the parts of the plants above the soil. The plants are dusted 48 hours later with conidia of the fungus. The infected plants are placed in a greenhouse at 22°. Evaluation of fungus infestation is made 12 days after infection.

Compounds of the Tables exhibit good activity.

Example B-8: Action Against *Podosphaera leucotricha* on Apple Shoots

Apple cuttings with about 15 cm long fresh shoots are sprayed with a spray mixture (0.06% active ingredient). After 24 hours, the treated plants are infected with a conidia suspension of the fungus and are placed in a climatic chamber at 70% relative humidity and 20° C. Fungus infestation is evaluated 12 days after infection.

Compounds of the Tables exhibit good activity.

BIOLOGICAL EXAMPLES: B. INSECTICIDAL ACTION

Example B-9: Action Against *Aphis craccivora*

Pea seedlings are infested with *Aphis craccivora* and then sprayed with a spray mixture comprising 400 ppm of test compound, and incubated at 20° C. The percentage reduction in the population (% activity) is determined 3 and 6 days later by comparing the number of dead aphids on the treated plants with that on untreated plants.

Compounds of the Tables exhibit good activity in this test, i.e. a mortality of more than 80%.

Example B-10: Action Against *Diabrotica balteata*

Maize seedlings are sprayed with an aqueous emulsion comprising 400 ppm of test compound. After the spray coating has dried, the maize seedlings are populated with 10 *Diabrotica balteata* larvae in the second stage and then placed in a plastics container. The percentage reduction in the population (% activity) is determined 6 days later by comparing the number of dead larvae on the treated plants with that on untreated plants.

Compounds of the Tables exhibit good activity in this test.

Example B-11: Action Against *Heliothis virescens*

Young soybean plants are sprayed with an aqueous emulsion comprising 400 ppm of test compound. After the spray coating has dried, the soybean plants are populated with 10 *Heliothis virescens* caterpillars in the first stage and then placed in a plastics container. The percentage reduction in the population and the percentage reduction in feeding damage (% activity) are determined 6 days later by comparing the number of dead caterpillars and the feeding damage on the treated plants with that on untreated plants.

Compounds of the Tables exhibit good activity in this test.

Example B-12: Action Against *Spodoptera littoralis*

Young soybean plants are sprayed with an aqueous emulsion comprising 400 ppm of test compound. After the spray coating has dried, the soybean plants are populated with 10 *Spodoptera littoralis* caterpillars in the third stage and then placed in a plastics container. The percentage reduction in the population and the percentage reduction in feeding damage (% activity) are determined 3 days later by comparing the number of dead caterpillars and the feeding damage on the treated plants with that on untreated plants.

Compounds of the Tables exhibit good activity in this test.

Example B-13: Action Against *Nilaparvata lugens*

Rice plants are sprayed with an aqueous emulsion comprising 400 ppm of test compound. After the spray coating has dried, the rice plants are populated with plant hopper larvae in the 2nd and 3rd stages. Evaluation is made 21 days later. The percentage reduction in the population (% activity) is determined by comparing the number of surviving plant hoppers on the treated plants with that on untreated plants.

The compounds of the Tables are more than 90% effective.

Example B-14: Action Against *Plutella xylostella* Caterpillars

Young cabbage plants are sprayed with an aqueous emulsion comprising 400 ppm of test compound. After the spray coating has dried, the cabbage plants are populated with 10 *Plutella xylostella* caterpillars in the third stage and placed in a plastics container. Evaluation is made 3 days later. The percentage reduction in the population and the percentage reduction in feeding damage (% activity) are determined by comparing the number of dead caterpillars and the feeding damage on the treated plants with that on untreated plants.

Compounds of the Tables exhibit good activity.

Example B-15: Action Against *Musca domestica*

A sugar cube is treated with a solution of the test compound in such a manner that after drying overnight the concentration of test compound in the sugar is 250 ppm. The treated sugar cube, together with a wet cotton wool swab and 10 *Musca domestica* adults of an OP-resistant strain, is placed in an aluminium dish, covered with a glass beaker and incubated at 25° C. After 24 hours the mortality is determined.

Compounds of the Tables exhibit good activity.

BIOLOGICAL EXAMPLES: C. ACARICIDAL ACTION

Example B-16: Action Against *Tetranychus urticae*

Young bean plants are populated with a mixed population of *Tetranychus urticae* and sprayed one day later with an aqueous emulsion comprising 400 ppm of test compound. The plants are then incubated for 6 days at 25° C. and then evaluated. The percentage reduction in the population (% activity) is determined by comparing the number of dead eggs, larvae and adults on the treated plants with that on untreated plants.

Compounds of the Tables exhibit good activity.

Example B-17: Action Against a Mixed Population of *Tetranychus cinnabarinus*

Dilution Series

Dwarf beans in the 2-leaf stage are populated with a mixed population (eggs, larvae/nymphs, adults) of an OP-tolerant strain of *Tetranychus cinnabarinus*. The test compounds are applied to the plants 24 hours after infection in concentrations of 200, 100, 50 mg a.i./l in an automatic spraying chamber. The test compounds are in the form of formulations and are diluted to the corresponding concentrations with water. 2 and 7 days after application the test is evaluated for % mortality in respect of eggs, larvae/nymphs and adults. Compounds of the Tables exhibit over 70% mortality in dilutions down to 50 mg a.i./liter.

Example B-18: Action Against *Boophilus microplus*

Adult female ticks which are replete with blood are affixed to a PVC plate and covered with a cotton wool swab. 10 ml of an aqueous test solution comprising 125 ppm of the test compound are poured over the test insects. The cotton wool swab is removed and the ticks are incubated for 4 weeks until oviposition has taken place. The action manifests itself either as mortality or sterility of the females or as ovidical action in the eggs.

What is claimed is:
1. A compound of formula I

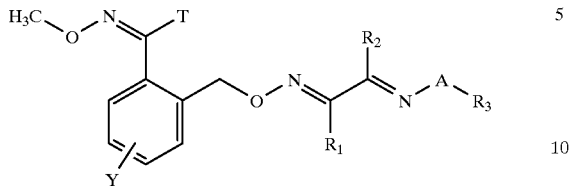

or a possible isomer or isomeric mixture thereof, wherein
Y is hydrogen, $C_1$–$C_4$alkyl, $C_1$–$C_4$alkoxy, OH, CN, $NO_2$, $Si(CH_3)_3$, $CF_3$ or halogen,
T is a group a)

and the remaining substituents are defined as follows:
X is O, S or $NR_{13}$;
A is O or $NR_4$;
$R_1$ is hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano;
$R_2$ is hydrogen, $C_1$–$C_6$alkyl, $C_3$–$C_6$cycloalkyl, cyano, unsubstituted or substituted $C_1$–$C_6$alkoxycarbonyl, unsubstituted or substituted di($C_1$–$C_6$alkyl) aminocarbonyl, unsubstituted or substituted $C_1$–$C_6$alkyl-S(O)$_q$, unsubstituted or substituted aryl-S(O)$_q$, unsubstituted or substituted heteroaryl, unsubstituted or substituted heterocyclyl or unsubstituted or substituted heterocyclylcarbonyl; a group

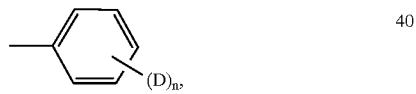

a group

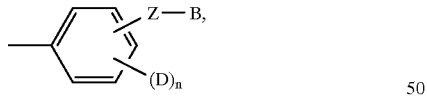

or thienyl;
D is identical or different and is selected from halogen, $C_1$–$C_4$alkyl, $C_1$–$C_4$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, cyano and nitro;
n is 0, 1, 2, 3 or 4;
Z is —O—, —O-($C_1$–$C_4$alkyl)-, -($C_1$–$C_4$alkyl)-O—, —S(O)$_m$—, -($C_1$–$C_4$alkyl)-S(O)$_m$— or —S(O)$_m$-($C_1$–$C_4$alkyl)-,
m is 0, 1 or 2,
B is $C_1$–$C_6$alkyl, halo-$C_1$–$C_6$alkyl, $C_3$–$C_6$cycloalkyl; $C_2$–$C_6$alkenyl or $C_2$–$C_4$alkynyl-$C_1$–$C_2$alkyl each of which is unsubstituted or substituted by from 1 to 3 halogen atoms; aryl, heteroaryl or heterocyclyl, all three of which are unsubstituted or substituted by from one to five substituents selected independently of one another from $C_1$–$C_6$alkyl, halo-$C_1$–$C_6$alkyl, halogen, $C_1$–$C_6$alkoxy and halo-$C_1$–$C_6$alkoxy, or is a group

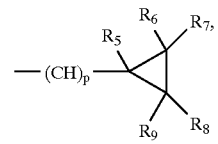

or trimethylsilyl;
$R_5$, $R_6$, $R_7$, $R_8$ and $R_9$ are each independently of the others hydrogen, $C_1$–$C_4$alkyl or halogen and
p is 0, 1, 2 or 3;
q is 1 or 2;
$R_3$ is hydrogen, $C_1$–$C_6$alkyl, $C_1$–$C_6$haloalkyl having from 1 to 5 halogen atoms, $C_1$–$C_4$alkoxy-$C_1$–$C_2$alkyl, $C_2$–$C_4$alkenyl-$C_1$–$C_2$alkyl that is unsubstituted or substituted by from 1 to 3 halogen atoms, $C_2$–$C_4$alkynyl-$C_1$–$C_2$alkyl, $C_3$–$C_6$cycloalkyl that is unsubstituted or substituted by from 1 to 4 halogen atoms, $C_3$–$C_6$cycloalkyl-$C_1$–$C_4$alkyl that is unsubstituted or substituted by from 1 to 4 halogen atoms, cyano-$C_1$–$C_4$alkyl, $C_1$–$C_4$alkoxycarbonyl-$C_1$–$C_2$alkyl, $C_1$–$C_4$alkoxycarbamoyl-$C_1$–$C_2$alkyl, phenyl-$C_1$–$C_3$alkyl that is unsubstituted or substituted by halogen, $C_1$–$C_3$alkyl, $C_1$–$C_4$alkoxy, $C_1$–$C_4$haloalkyl, cyano, nitro or by $C_1$–$C_4$alkylenedioxy, it being possible for the phenyl group to be mono- to tri-substituted by identical or different substituents; phenyl that is unsubstituted or substituted by one or two substituents selected independently of one another from $C_1$–$C_4$alkyl, $C_1$–$C_4$alkoxy, halogen, $C_1$–$C_2$haloalkyl having from 1 to 3 halogen atoms, nitro and cyano, or pyridyl that is unsubstituted or substituted by one or two substituents selected independently of one another from $C_1$–$C_4$alkyl, $C_1$–$C_4$alkoxy, halogen, $C_1$–$C_2$haloalkyl having from 1 to 3 halogen atoms, nitro and cyano;
$R_4$ is $C_1$–$C_4$alkyl or phenyl, or
$R_3$ and $R_4$, together with the nitrogen atom to which they are bonded, form an unsubstituted or $C_1$–$C_4$alkyl-substituted, saturated or unsaturated 5- to 7-membered ring which may contain from 1 to 3 additional hetero atoms selected from N, O and S;
$R_{10}$ is hydrogen, $C_1$–$C_4$alkyl, $C_2$–$C_4$alkenyl, $C_2$–$C_4$alkynyl, $C_3$–$C_6$cycloalkyl, phenyl that is unsubstituted or substituted by a maximum of three substituents selected from halogen, $C_1$–$C_4$alkyl, $C_1$–$C_4$alkoxy and $C_1$–$C_4$alkylthio, or benzyl that is unsubstituted or substituted in the same manner in the aromatic nucleus by a maximum of three substituents; cyclopropylmethyl, $C_1$–$C_4$haloalkyl, $C_2$–$C_4$haloalkenyl, $C_2$–$C_5$alkoxyalkyl, cyanomethyl, CO—$R_{14}$, OH, $NH_2$, $C_1$–$C_6$alkylamine, $C_1$–$C_4$haloalkylamine or $C_1$–$C_4$alkoxycarbonyl-$C_1$–$C_2$alkyl;
$R_{11}$ is hydrogen, $C_1$–$C_4$alkyl, $C_2$–$C_4$alkenyl, $C_2$–$C_4$alkynyl, $C_3$–$C_6$cycloalkyl, C(O)$R_{14}$, OH, $NH_2$, $C_1$–$C_4$alkoxy, $C_2$–$C_4$alkenyloxy, $C_2$–$C_4$alkynyloxy, $C_1$–$C_4$alkylamine or $C_1$–$C_4$haloalkylamine;
$R_{13}$ is hydrogen, $C_1$–$C_4$alkyl, $C_2$–$C_4$alkenyl or $C_2$–$C_4$alkynyl;

R$_{14}$ is hydrogen, C$_1$–C$_4$alkyl, C$_1$–C$_4$haloalkyl, C$_1$–C$_4$alkoxy, C$_3$–C$_6$cycloalkyl, C$_1$–C$_4$alkoxycarbonyl, or phenyl that is unsubstituted or substituted by a maximum of three substituents selected from halogen, C$_1$–C$_4$alkyl and C$_1$–C$_4$alkoxy.

2. A compound of formula I according to claim 1, wherein Y is hydrogen.

3. A compound of formula I according to claim 1, wherein
X is oxygen;
R$_{10}$ is C$_1$–C$_2$alkyl;
R$_{11}$ is hydrogen, C$_1$–C$_2$alkyl, OH or C$_1$–C$_2$alkoxy.

4. A compound of formula I according to claim 1, wherein
X is sulfur;
R$_{10}$ is methyl, ethyl, allyl, benzyl or cyclopropylmethyl; and
R$_{11}$ is hydrogen or C$_1$–C$_2$alkyl.

5. A compound of formula I according to claim 1, wherein
X is NR$_{13}$;
R$_{13}$ is hydrogen or C$_1$–C$_4$alkyl; and
R$_{10}$ and R$_{11}$ are each independently of the other hydrogen, C$_1$–C$_4$alkyl, C$_1$–C$_6$alkylamine or C$_1$–C$_4$haloalkylamine.

6. A compound of formula I according to claim 1, wherein A is oxygen, NCH$_3$ or N—C$_6$H$_5$.

7. A compound of formula I according to claim 1, wherein R$_1$ is hydrogen, methyl, cyclopropyl, methylthio or cyano.

8. A compound of formula I according to claim 1, wherein R$_2$ is C$_1$–C$_4$alkyl or cyclopropyl.

9. A compound of formula I according to claim 1, wherein
R$_2$ is cyano, unsubstituted or substituted C$_1$–C$_6$alkoxycarbonyl, unsubstituted or substituted di(C$_1$–C$_6$alkylamine)carbonyl, unsubstituted or substituted heterocyclylcarbonyl, unsubstituted or substituted C$_1$–C$_6$alkyl-S(O)$_q$, unsubstituted or substituted aryl-S(O)$_q$, unsubstituted or substituted heteroaryl or unsubstituted or substituted heterocyclyl; and
q is 1 or 2.

10. A compound of formula I, wherein
R$_2$ is a group

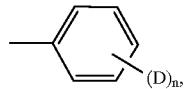

and
D is halogen, C$_1$–C$_4$alkyl, C$_1$–C$_4$alkoxy, C$_1$–C$_2$alkyl substituted by from 1 to 5 halogen atoms, C$_1$–C$_2$haloalkoxy, C$_3$–C$_6$alkenyloxy, C$_3$–C$_6$alkynyloxy, C$_1$–C$_4$alkylenedioxy, cyano, or nitro, or thienyl.

11. A compound of formula I according to claim 1, wherein
R$_2$ is a group

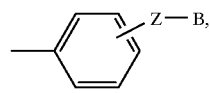

and
Z is —O—, —O-(C$_1$–C$_4$alkyl)-, -(C$_1$–C$_4$alkyl)-O—, —S(O)$_m$—, -(C$_1$–C$_4$alkyl)-S(O)$_m$— or —S(O)$_m$-(C$_1$–C$_4$alkyl)-, and
m is 0, 1 or 2.

12. A compound of formula I according to claim 1, wherein
R$_2$ is a group

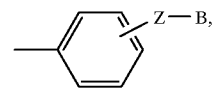

and
B is C$_1$–C$_4$alkyl, halo-C$_1$–C$_4$alkyl; C$_2$–C$_4$alkenyl or C$_2$–C$_4$alkynyl-C$_1$–C$_2$alkyl each of which is unsubstituted or substituted by from 1 to 3 halogen atoms; aryl or aryl that is substituted by one or two substituents selected independently of one another from C$_1$–C$_2$alkyl, halo-C$_1$–C$_2$alkyl, halogen, C$_1$–C$_2$alkoxy and halo-C$_1$–C$_2$alkoxy, or is a group

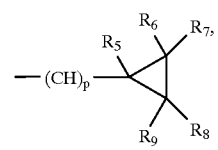

R$_5$, R$_6$, R$_7$, R$_8$ and R$_9$ are each independently of the others hydrogen, C$_1$–C$_2$alkyl or halogen, and
p is 0, 1, 2 or 3.

13. A compound of formula I according to claim 1, wherein
R$_2$ is a phenyl group substituted in the 4-position by Z—B.

14. A compound of formula I according to claim 1, wherein
R$_3$ is hydrogen, C$_1$–C$_6$alkyl, C$_1$–C$_4$haloalkyl having from 1 to 3 halogen atoms, C$_1$–C$_2$alkoxy-C$_1$–C$_2$alkyl, C$_1$–C$_4$alkoxycarbonyl-C$_1$–C$_2$alkyl, propenyl that is unsubstituted or substituted by from 1 to 3 halogen atoms, propargyl, C$_3$–C$_6$cycloalkyl, cyclopropylmethyl that is unsubstituted or substituted by 1 or 2 halogen atoms, cyano-C$_1$–C$_2$alkyl, phenyl-C$_1$–C$_2$alkyl that is unsubstituted or substituted by halogen, methyl, methoxy or by halomethyl having from 1 to 3 halogen atoms, wherein the phenyl group may be substituted by one or two identical or different substituents; phenyl that is unsubstituted or substituted by one or two substituents selected independently of one another from halogen, methyl, methoxy, halomethyl having from 1 to 3 halogen atoms, cyano and nitro; or pyridyl that is unsubstituted or substituted by one or two substituents selected independently of one another from halogen, methyl, methoxy, halomethyl having from 1 to 3 halogen atoms, cyano and nitro; or
R$_3$ and R$_4$, together with the nitrogen atom to which they are bonded, form an unsubstituted or C$_1$–C$_4$alkyl-substituted, saturated or unsaturated 5- to 7-membered ring which may contain from 1 to 3 additional hetero atoms selected from N, O and S.

15. A compound of formula I according to claim 1, wherein $R_4$ is methyl or phenyl.

16. A compound of formula I according to claim 1, wherein $R_3$ is $C_1$–$C_6$alkyl, $C_1$–$C_6$haloalkyl having from 1 to 5 halogen atoms, or $C_3$–$C_6$cycloalkyl-$C_1$–$C_4$alkyl that is unsubstituted or substituted by from 1 to 4 halogen atoms.

17. A compound of formula I according to claim 1, wherein $R_2$ is methyl, cyano, cyclopropyl, unsubstituted or substituted $C_1$–$C_6$alkoxycarbonyl, unsubstituted or substituted heterocyclyl or unsubstituted or substituted heteroaryl and $R_3$ is $C_1$–$C_6$alkyl, $C_1$–$C_6$haloalkyl, or $C_3$–$C_6$cycloalkyl-$C_1$–$C_4$alkyl that is unsubstituted or substituted by from 1 to 4 halogen atoms.

18. A compound of formula I according to claim 1, wherein the $CH_3ON{=}C$ double bond adjacent to has the E-form.

19. A composition for controlling pests, comprising as active ingredient an effective amount of a compound according to claim 1, together with a suitable carrier.

20. A composition according to claim 19, wherein the pests are phytopathogenic fungi.

21. A composition according to claim 19, wherein the pests are insects or Acarina.

22. A method of controlling and preventing infestation by pests, in which method a compound according to claim 1 is applied to the pests or to the habitat thereof.

23. A method according to claim 22, wherein the pests are phytopathogenic fungi.

24. A method according to claim 22, wherein the pests are insects or Acarina.

25. A method according to claim 22, wherein seed is treated.

26. Seed that has been treated in accordance with claim 25.

27. A compound of formula III

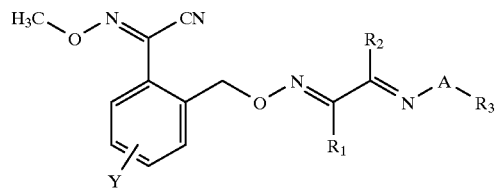

wherein A, $R_1$, $R_2$, $R_3$ and Y are as defined for formula I.

28. A compound according to claim 27, wherein

A is oxygen, and

Y is hydrogen, and $R_1$, $R_2$ and $R_3$ are as defined for formula I.

29. A compound according to claim 28, wherein $R_1$ and $R_3$ are methyl.

30. A compound of claim 10 wherein D is fluorine, chlorine, bromine, $C_{1-4}$alkyl, or —$CF_3$.

* * * * *

UNITED STATES PATENT AND TRADEMARK OFFICE
CERTIFICATE OF CORRECTION

PATENT NO. : 5,977,182
DATED : November 2, 1999
INVENTOR(S) : ZURFLÜH ET AL.

It is certified that error appears in the above-identified patent and that said Letters Patent is hereby corrected as shown below:

Column 95, Claim 18, second line, after the word "to" insert the letter -- T -- .

Signed and Sealed this

First Day of August, 2000

Attest:

Q. TODD DICKINSON

Attesting Officer

Director of Patents and Trademarks